United States Patent [19]
Anderson et al.

[11] Patent Number: 5,837,689
[45] Date of Patent: *Nov. 17, 1998

[54] SIALYL LEWIS-X MIMETICS CONTAINING NAPHTHYL BACKBONES

[75] Inventors: Mark B. Anderson, Orinda; Daniel E. Levy, Oakland; Peng Cho Tang, Moraga; John H. Musser, San Carlos; Narasinga Rao, Alameda, all of Calif.

[73] Assignee: Glycomed Incorporated, Alameda, Calif.

[ * ] Notice: The term of this patent shall not extend beyond the expiration date of Pat. No. 5,658,880.

[21] Appl. No.: 604,160

[22] Filed: Feb. 21, 1996

Related U.S. Application Data

[63] Continuation-in-part of Ser. No. 446,185, May 19, 1995, and Ser. No. 289,715, Aug. 12, 1994, Pat. No. 5,658,880, which is a continuation-in-part of Ser. No. 78,949, Jun. 16, 1993, abandoned.

[51] Int. Cl.$^6$ ............................. A61K 31/70; C07H 15/00
[52] U.S. Cl. ................................ 514/25; 514/24; 514/42; 536/4.1; 536/17.2; 536/17.5; 536/17.9
[58] Field of Search ................................ 514/24, 25, 42; 536/4.1, 17.2, 17.5, 17.9

[56] References Cited

U.S. PATENT DOCUMENTS

| | | | |
|---|---|---|---|
| 4,849,513 | 7/1989 | Smith et al. | 536/27 |
| 5,138,044 | 8/1992 | Dasgupta | 536/18.5 |
| 5,143,712 | 9/1992 | Brandley et al. | 424/1.1 |
| 5,211,937 | 5/1993 | Brandley et al. | 424/1.1 |
| 5,296,594 | 3/1994 | Ratcliffe et al. | 536/53 |
| 5,316,913 | 5/1994 | Butcher et al. | 435/7.24 |
| 5,318,890 | 6/1994 | Rosen et al. | 435/7.25 |
| 5,527,890 | 6/1996 | Rao | 536/5 |

FOREIGN PATENT DOCUMENTS

| | | |
|---|---|---|
| 9013300 | 11/1990 | WIPO . |
| 9107993 | 6/1991 | WIPO . |
| 9119501 | 12/1991 | WIPO . |
| 9119502 | 12/1991 | WIPO . |
| 9207572 | 5/1992 | WIPO . |
| 9209293 | 6/1992 | WIPO . |
| 9214757 | 9/1992 | WIPO . |
| 9216612 | 10/1992 | WIPO . |
| 9218610 | 10/1992 | WIPO . |
| 9300908 | 1/1993 | WIPO . |
| 9300919 | 1/1993 | WIPO . |
| 9408051 | 4/1994 | WIPO . |
| 9411030 | 5/1994 | WIPO . |
| 9503315 | 2/1995 | WIPO . |
| 9505182 | 2/1995 | WIPO . |
| 9605209 | 2/1996 | WIPO . |

OTHER PUBLICATIONS

Dasgupta, F. et al., "Anti–Adhesive Therapeutics: A New Case of Anti–Inflammatory Agents," *Expert Opinion on Investigation Drugs*, vol. 3, No. 7, pp. 709–724 (1994) Month Not Available.

Giannis, Athanassios, "Die Sialyl–Lewis–X–Gruppe und ihre Analoga als Liganden fur Selektine: chemoenzymatische Synthesen und biolgische Funktionen", *Angew. Chem.*, vol. 106, No. 2, pp. 188–191 (1994) Month Not Available.

International Search Report for International Application No. PCT/US97/02951, No Publication Date.

Allanson et al., "A Novel Mimic of the Sialyl Lewis$^x$ Determinant," *Tetrahedron Lett.* 34(24):3945–3948 (1993). Month Not Available.

Arnaout, "Structure and Function of the Leukocyte Adhesion Molecule CD11/CD18," *Blood* 75(5):1307–1050 (1990). Month Not Available.

Aruffo et al., "Molecular cloning of a CD28 cDNA by a high–efficiency COS cell expression system," *Proc. Natl. Acad. Sci. USA* 84:8573–8577 (1987) Month Not Available.

Aruffo et al., "Granule membrane protein 140 (GMP140) binds to carcinomas and carcinoma–derived cell lines," *Proc. Natl. Acad. Sci. USA* 89:2292–2296 (1992). Month Not Available.

Aruffo et al., "CD62/P–Selectin Recognition of Myeloid and Tumor Cell Sulfatides," *Cell* 67:35–44 (1991). Month Not Available.

Ball et al., *ACS* 114(13):5449–5451 (1992).

Berg et al., "A carbohydrate domain common both to Sialyl Le$^x$ is recognized by the Endothelial Cell Leukocyte Adhesion Molecule ELAM–1," *J. Biol. Chem.* 268(23):14869–14872 (1991). Month Not Available.

Bevilacqua et al., "Endothelial Leukocyte Adhesion Molecule 1: An Inducible Receptor for Neutrophils Related to Complement Regulatory Proteins and Lectins," *Science* 243:1160–1161 (1989). Month Not Available.

Blackburn et al., "Gangliosides Support Neural Retina Cell Adhesion,"*J. Biol. Chem.* 261(1):2873–2881 (1966). Month Not Available.

Bohl et al., "Molecular Structure and Biological Activity of Steriods," *CRC Press, Inc.* pp. 453–457 (1992). Month Not Available.

(List continued on next page.)

*Primary Examiner*—Kathleen K. Fonda
*Attorney, Agent, or Firm*—Lyon & Lyon LLP

[57] ABSTRACT

Compounds that possess selectin binding activity are described that have a three-dimensionally stable configuration for sialic acid and fucose, or analogs, derivatives, or mimics of these groups, such that sialic acid and fucose or their mimics are separated by a linker that permits binding between those groups and the selecting, such compounds being represented by the following general structural formula I:

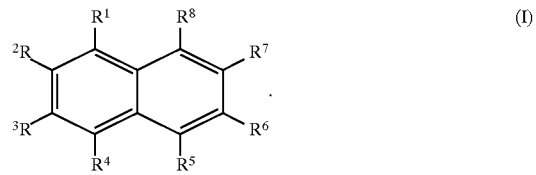

33 Claims, 2 Drawing Sheets

OTHER PUBLICATIONS

Borman, "Race Is On To Develop Sugar–Based Anti–Inflammatory, Anti Tumor Drugs," *C&EN* 25–28 (1992). Month Not Available.

Brenner et al., "Encoded Combinatorial Chemistry," *Proc. Natl. Acad. Sci. USA* 89:5381–5383 (1992). Month Not Available.

Buerke et al., "Sialyl Lewis$^x$ –containing Oligosaccharide Attenutates Myocardial Reperfusion Injury in Cats," *J. Clin. Invest.* 93:1140–1148 (1994). Month Not Available.

"Carbohydrate Chemistry," *Specialist Periodical Reports, Royal Society of Chemistry* pp. 17–57 (1992). Month Not Available.

"Combinatorial Chemistry" *Molecular Connection Special Supplement* 14:1–5 (Mar. 1995).

Chen et al., "Analogous Organic Synthesis of Small–Compound Libraries: Validation of Combinatorial Chemistry in Small–Molecules Synthesis," *J. Am. Chem. Soc.* 116:2661–2662 (1994) Month Not Available.

Chmielewski et al., "Synthesis of Phosphonate Analogs of α–D–glucopyranosyl and α–D–glactopyranosyl Phosphate," *Carb. Res.* C1–C4 (1981). Month Not Available.

Clark et al., "Yeast Oligosaccharyltransferase; Glycosylation of Peptide Substrates and Chemical Characterization of the Glycopeptide Product," *J. Org. Chem.* 55:6275–6285 (1990). Month Not Available.

Dasgupta et al., "Anti–adhesive therapeutics: a new class of anti–inflammatory agents," *Ex. Opin. Invest. Drugs* 3(7):709–724 (1994). Month Not Available.

Daves, "C–Glycoside Synthesis by Palladium–Mediated Glycol–Aglycon Coupling Reaction," *Acc. Chem. Res.* 23:201–206 (1990). Month Not Available.

DeFrees et al., "Ligand Recognition by E–Selectin: Analysis of Conformation and Activity of Synthetic Monomeric and Bivalent Sialyl Lewis X Analogs," *J. Am. Chem. Soc.* 115:7549–7550 (1993). Month Not Available.

Ecker et al., "Combinatorial Drug Discovery: Which Methods Will Produce the Greatest Value?" *Biotechnology* 13:351–360 (1995). Month Not Available.

Erbe et al., "P–and E–Selectin Use Common Sites for Carbohydrate Ligand Recognition and Cell Adhesion," *J. Cell. Biol.* 120(5)1:1227–1235 (1993). Month Not Available.

Frecht, "Synthesis an Applications of Organic Polymers as Suports and Protecting Groups," *Tetrahedron Lett.* 37:663–683 (1981).

Gallop et al., "Applications of Combinatorial Technologies to Drug Discovery. 1. Background and peptide Combinatorial Libraries," *J. of Medicinal Chemistry* 37:1233–1251 (1994) Month Not Available.

Gordon et al., "Applications of Combinatorial Technologies to Drug Discovery. 2 Combinatorial Organic Synthesis, Library Screening Strategies and Future Directions," *J. Med. Chem.* 37:1385–1401 (1994). No Month Available.

Gundel et al, "Endothelial Leukocyte Adhesion Molecule–1 Mediates Antigen–induced Acute Airway Inflammation and Late–phase Airway Obstruction in Monkeys," *J. Clin. Invest.* 1407–1411 (1991). Month Not Available.

Hacksell et al., "The Chemistry and Biochemistry of C–Nucleosides and C–Arylglycosides," *Prog. Med. Chem.* 22:1–65 (1985). Month Not Available.

Handa et al., "Selectin GMP–140 (CD62$_1$ PADGEM) binds to Sialosyl–Le$^a$ and Sialosyl–Le$^x$, and Sulfated Glycans Modulate This Binding," *Biochem. Biophys. Res. Commun.* 181(13):1223–1230 (1991). Month Not Available.

Hession et al., "Endothelial leukocyte adhesion molecule 1: Direct expression cloning and functional interactions," *Proc. Natl. Acad. Sci. USA* 87:1673–1677 (1990)Month Not Available.

Jacobs et al., "Combinatorial Chemistry—Applications of Light–Directed Chemical Synthesis," *Tibtech* 12:19–26 (1994). No Month Available.

Johnston et al., "Cloning of GMP–140, a Granule Membrane Protein of Platelets and Endothelium: Sequence Similarity to Proteins Involved in Cell Adhesion and Inflammation," *Cell* 56:1033–1044 (1989). No Month Available.

Kometani et al., "Boron Trifluoride–Catalyzed Rearrangement of 2–Aryloxytetrahydropyrans: A New Entry to C–Arylglycosidation," *Synthesis* pp. 1005–1007 (Dec. 1988).

Larsen et al., "PADGEM Protein: A Receptor that Mediates the Interaction of Activated Platelets with Neutrophils and Monocytes," *Cell* 59:305–312 (1989). No Month Available.

Lasky et al., "Cloning of a Lymphocyte Homing Receptor Reveals a Lectin Domain," *Cell* 56:1045–1055 (1989). No Month Available.

Lewinsohn et al., "Leukocyte–Endothelial Cell Recognition: Evidence of a Common Molecular Mechanism Shared by Neutrophils, Lymphocytes, and Other Leukocytes," *J. Immunol.* 138(12):4313–4321 (1987). No Month Available.

Lo et al., "Two Leukocyte Receptors (CD11a/CD18 and CD11b/CD18) Mediate Transient Adhesion to Endothelium by Binding to Different Ligands," *J. Immunol.* 143(10):3325–3329 A(1989). No Month Available.

Lowe et al., "ELAM–1–Dependent Cell Adhesion to Vascular Endothelium Determined by a Transfected Human Fucosyltransferase cDNA," *Cell* 63:475–484 (1990). No Month Available.

Ma et al., "Monoclonal Antibody to L–Selectin Attenuates Neutrophil Accumulation and Protects Ishemic Reperfused Cat Myocardium," *Circulation* 88(2):649–658 (1993). No Month Available.

Mulligan et al., "Role of Endothelial–Leukocyte Adhesion Molecule 1 (ELAM–1) in Neutrophil–Mediated Lung Injury in Rats," *J. Clin. Invest.* 88:1396–1406 (1991). No Month Available.

Mulligan et al., "Protective effects of oligosaccharides in P–selectin–dependent lung injury," *Nature* 364:149–151 (1993). No Month Available.

Musser et al., "Carbohyderate–Based Therapeutics," Burger's *Medicinal Chemistry and Drug Discovery* 1:901–947 (1995). Month Not Available.

Nielsen et al., "Synthetic Methods for the Implementation of Encoded Combinatorial Chemistry," *J. Am. Chem. Soc.* 115:9812–9813 (1993). Month Not Available.

Ohlmeyer et al., "Complex Synthetic Chemical Libraries Indexed with Molecular Tags," *Proc. Natl. Acad. Sci. USA* 90:10922–10926 (1993). Month Not Available.

Osborn et al., "Direct Expression of Vascular Cell Adhesion Molecule 1, a Cytokine–Induced Endothelial Protein That Binds to Lymphocytes," *Cell* 59:1203–1211 (1989). Month Not Available.

Otvos et al., "Automated Solid–Phase Synthesis of Glycocpeptides. Incorporation of Unprotected Mono–and Disaccharide Units of N–Glycoprotein Antennae into T Cell Epitopic Peptides," *Tetrahedron Lett.* 31:5889–5892 (1990). Month Not Available.

Palabrica et al., "Leukocyte accumulation promoting fibrin deposition is mediated in vivo by P–selectin on adherent platelets," *Nature* 359:848–851 (1992). Month Not Available.

Panek et al., "Oxygenated Allylic Silans: Useful Homoenolate Equivalents for the Steroselective C–Glycosidation of Pyranoside Derivatives," *J. Org. Chem.* 54:2034–2038 (1989). Month Not Available.

Phillips et al., "ELAM–1 Mediates Cell Adhesion by Recognition of a Carbohydrate Ligand, Sialyl–Le$^x$, " *Science* 250: 1130–1132 (1990). Month Not Available.

Polte et al., "cDNA for endothelial leukocyte adhesion molecule 1 (ELAM 1): sequence differences," *Nucleic Acids Research* 18(4):1803 (1990). Month Not Available.

Postema, "Recent Developments in the Synthesis of C–Glycosides," *Tetrahedron* 48:8545–8599 (1992). Month Not Available.

Taylor et al., "Antithrombin–III Prevents the Lethal Effects of *Escherichia coli* Infusion in Baboons," *Circulatory Shock* 26:227–235 (1988). Month Not Available.

Taylor et al., "Protein C Prevents the Coagulopathic and Lethal Effects of *Escherichia coli* infusion in the Baboon," *J. Clin. Invest.* 79:918–925 (1987). Month Not Available.

Tedder et al., "Isolation and Chromosomal Localization cDNAs Encoding a Novel Human Lymphocyte Cell Surface Molecule, LAM–1," *J. Exp. Med.* 170:123–133 (1989). Month Not Available.

Turunen et al., "Sialyl Lewis$^x$–and L–selectin–dependent site specific lymphocyte extravasation into renal transplants during acute rejection," *Eur. J. Immunol.* 24:1130–1136 (1994). Month Not Available.

Tyrrell et al., "Structural requirements for the carbohydrate ligand of E–selectin," *Proc. Natl. Acad. Sci. USA* 88:10372–10376 (1991). Month Not Available.

Walz et al., "Recognition by Elam–1 of the Sialyl–Le$^x$ Determinant on Myeloid and Tumor Cells," *Science* 250:1132–1135 (1990). Month Not Available.

Watson et al., "neutrophil influx into an inflammatory site inhibited by a soluble homing receptor–IgG chimaera," *Nature* 349:164–167 (1991). Month Not Available.

SIALYL LEWIS-X MIMETICS CONTAINING NAPHTHYL BACKBONES

This application is a continuation-in-part of Ser. No. 08/289,715, filed Aug. 12, 1994, now U.S. Pat. No. 5,658,880, which is a continuation-in-part of Ser. No. 08/078,949, filed Jun. 16, 1993, now abandoned. This application is also a continuation-in-part of Ser. No. 08/446,185, filed May 19, 1995. All of these applications are incorporated herein by reference in their entirety.

FIELD OF THE INVENTION

This invention relates generally to the field of medicinal chemistry, and specifically to medicaments that are characterized by their capacity to bind to one or more of the three known selectins: E, L, and P-selectins. The medicaments consist of substituted pseudo-oligosaccharides wherein three chemical moieties are covalently linked in the following order: sialic acid, or an analogue, derivative, or mimic thereof, a naphthyl spacer, and fucose or an analogue, derivative, or mimic thereof. Such medicaments have significant applications for diagnosis or prophylactic or therapeutic treatment of certain diseases including cancer, autoimmunity, and inflammation.

BACKGROUND OF THE INVENTION

A large body of data has been accumulated that establishes a family of receptors, the selectins (LEC-CAMs) in certain diseases including cancer, autoimmunity, and in the inflammatory response. The three known members of this family, L-Selectin (LECAM-1, LAM-1, gp9OMEL), E-Selectin (LECAM-2, ELAM-1) and P-Selectin (LECAM-3, GMP-140, PADGEM), each contain a domain with homology to the calcium-dependent lectins (C-lectins), an EGF-like domain, and several complement binding protein-like domains (Bevilacqua et al., *Science* (1989) 243:1160–1165; Johnston et al., *Cell* (1989) 56:1033–1044; Lasky et al., *Cell* (1989) 56:1045–1055; Tedder et al., *J. Exp. Med.* (1989) 170:123–133, Dasgupta et al., *Exp. Opin. Invest. Drugs* (1994) 3(7):709). It has been proposed that the selectins bind to particular ligands and that this accounts for their biological activity. Thus, drugs that interfere with or prevent binding of the ligands to the selectins will be useful medicaments for treating a variety of diseases.

For instance, adhesion of circulating neutrophils to stimulated vascular endothelium is a primary event of the inflammatory response. Recently, Buerke et al. have demonstrated the important role of selectins in inflammatory states such as ischemia-reperfusion injury in cats (Buerke, M. et al., *J. Clin. Invest.* (1994) 93:1140). Turunen et al. have demonstrated the role of sLe$^x$ and L-selectin in site-specific lymphocyte extravasation in renal transplants during acute rejection (Turunen, J. P. et al., *Eur. J. Immunol.* (1994) 24:1130). P-selectin has been shown to be centrally involved particularly as related to acute lung injury. Mulligan et al. have reported strong protective effects using anti-P-selectin antibody in a rodent lung injury model. (Mulligan, M. S. et al., *J. Clin. Invest.*, (1991) 90:1600, Mulligan, M. S. et al., *Nature* (1993) 364:149). A central role of P-selectin in inflammation and thrombosis has been demonstrated by Palabrica et al. (Palabrica, T. et al., *Nature* (1992) 359:843).

Of the three selecting, E-selectin is particularly interesting because of its transient expression on endothelial cells in response to IL-1 or TNF (Bevilacqua et al., *Science* (1989) 243:1160). The time course of this induced expression(2–8 h) suggests a role for this receptor in initial neutrophil extravasation in response to infection and injury. Indeed, Gundel et al. have shown that antibody to E-selectin blocks the influx of neutrophils in a primate model of asthma and thus is beneficial for preventing airway obstruction resulting from the inflammatory response. (Gundel R. H. et al., *J. Clin. Invest.* (1991) 88:1407).

Several different groups have published papers regarding E-selectin ligands. Lowe et al., (1990) demonstrated a positive correlation between E-selectin dependent adhesion of HL-60 cell variants and transfected cell lines, with their expression of the sialyl Lewis x (sLe$^x$) oligosaccharide, NeuNAc α-2-3-Gal-β1-4(Fuc α-1-3)-GlcNAc. By transfecting cells with plasmids containing an α-(1,3/1,4) fucosyltransferase, they were able to convert non-myeloid COS or CHO lines into sLe$^x$-positive cells that bind in an E-selectin dependent manner. Walz et al., (1990) were able to inhibit the binding of an E-selectin-IgG chimera to HL-60 cells with a monoclonal antibody directed against sLe$^x$ or by glycoproteins with the sLe$^x$ structure, but could not demonstrate inhibition with CD65 or CD15 antibodies. Both groups concluded that the sLe$^x$ structure is the ligand for E-selectin.

Information regarding the DNA sequences encoding endothelial cell-leukocyte adhesion molecules are disclosed in PCT published application WO90/13300 published Nov. 15, 1990 incorporated herein by reference. The PCT publication cites numerous articles which may be related to endothelial cell-leukocyte adhesion molecules. The PCT publication claims methods of identifying E-selectin ligands, as well as methods of inhibiting adhesion between leukocytes and endothelial cells using such ligands and specifically refers to MILAs which are described as molecules involved in leukocyte adhesion to endothelial cells. Recent publications regarding selectin ligands describe the use of L-selectin as an indicator of neutrophil activation (Butcher et al., U.S. Pat. No. 5,316,913 issued May 31, 1994), and assays for inhibition of leukocyte adhesion (Rosen et al., U.S. Pat. No. 5,318,890 issued Jun. 7, 1994).

As alluded to above, the ligand for E-selectin, sLe$^x$, consists of at least sialic acid, fucose, and N-acetyl lactosamine. Lactosamine consists of galactose and 2-amino-2-deoxyglucose. Sialic acid and fucose are bound to the galactose and glucosamine moieties of lactosamine, respectively. Ligands that bind to the other selectins share similar structural features. Considering the obvious medical importance of selectin ligands, significant effort has been, and continues to be expended to identify the critical physical/chemical parameters associated with selectin ligands that enhance, or that are required for their activity (DeFrees, S. A., et al., *J. Am. Chem, Soc.*, (1993) 115:7549). In no small part this effort is being driven by the need to have selectin ligands that are inexpensive to produce (see U.S. Pat. No. 5,296,594 issued Mar. 22, 1994; Allanson, N. M. et al., *Tetrahedron Lett.*, (1993) 34:3945; Musser, J. H. et al., *Current Pharmaceutical Design* (1995) 221–232). It is generally thought that it will be prohibitively expensive to commercially produce naturally occurring sLe$^x$ by either enzymatic or chemical synthesis because of the number of sophisticated reactions involved.

The selectin family of adhesion molecules participate in acute inflammation by initiating neutrophil rolling on activated endothelial cells. This is particularly evident in studies of ischemia reperfusion injury, where P-selectin appears to be important in neutrophil recruitment to damaged tissue. The presence of L-selectin and E- or P-selectin ligands on mononuclear cells has implicated these receptor-ligand interactions in chronic inflammation. This has been supported by the finding of chronic expression of E-selectin in dermatologic conditions, and P-selectin expression on joint synovial endothelium derived from rheumatoid arthritis patients. L. Lasky *Annu. Rev. Biochem.* 64:113–39 (1995); "Selectin Family of Adhesion Molecules" by Michael Forrest and James C. Paulson in Physiology and Pathophysiology of Leukocyte Adhesion, Ed. by D. Niel Grangier and Deert Schmid-Schönbein, Oxford University Press, New York, N.Y. (1995).

SUMMARY OF THE INVENTION

A first object of the invention is the description of medicaments that are selectin ligand mimetics that bind to certain selectins wherein the mimetics lack the lactose core structure of the natural selectin ligand, sialyl Lewis$^x$ (sLe$^x$), and have substituted in its place a naphthyl moiety, relative to sLe$^x$. Such invention compounds are represented by the following general structural formula I:

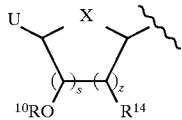

wherein
$R^1$, $R^2$, $R^3$, $R^4$, $R^5$, $R^6$, $R^7$, and $R^8$ are independently selected from the group consisting of
(a) —H, Y—B, alkyl of 1 to 4 carbon atoms optionally substituted with 1 to 2 lower alkyl groups,
—W((CH$_2$)$_n$—B)$_t$, —W((CH$_2$)$_m$—(CHR$^9$)$_q$—(CH$_2$)$_m$—A)$_t$;
—OH, lower alkoxy, lower aryloxy, lower aralkoxy, lower alkoxyaryl, amino,
—W((CH$_2$)$_n$—A)$_t$, —O—CH$_2$—C≡C—B, —N(Ac)—CH$_2$—C≡C—B, —NH—CH$_2$—C≡C—B, —N(CH$_2$—C≡C—B)$_2$, —N(Ac)CH$_2$Ar—B, —NHCH$_2$Ar—B, —N(CH$_2$Ar—B)$_2$, —OCH$_2$Ar—B, —(C=O)(CH$_2$)$_m$—B,
(b) a direct link to A, and a direct link to B; where Y—B is selected from the group consisting of

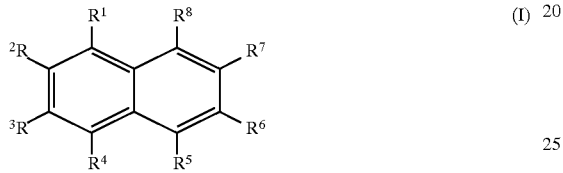

—W(CH$_2$CR$^{11}$(OR$^{11}$)CH$_2$—B)$_t$;

A is selected from the group consisting of —(C=O)R$^{11}$, sialic acid, Kemp's acid, quinic acid, —B, —SO$_3$M, —OSO$_3$M, —SO$_2$NH$_2$, —PO$_3$M'$_2$, —OPO$_3$M'$_2$, —NO$_2$, saturated or unsaturated carboxylic acids of 1 to 4 carbon atoms, optionally substituted with 1 to 2 hydroxyl groups, and esters, and amides thereof;

W is selected from the group consisting of a direct link, —O—, —N<, —S—, —NH—, and —NAc—;
B is wherein
U is selected from the group consisting of -R$^9$, —CH$_2$OR$^{10}$, —CH$_2$O-protecting group, —COOR$^{11}$, —CON(R$^{11}$)$_2$, and —COOM;
R$^9$ is lower alkyl;
each n is independently selected from the group 0, 1, 2, and 3;
each m is independently selected from the group 0, 1, 2, 3, and 4;
each q is independently selected from the group 0, 1, and 2;
each s is independently selected from the group 1, 2, and 3;
each z is independently selected from the group 1 and 2;
each t is independently selected from the group 1 and 2, with the proviso that when W is —N<, then t is 2, and for all other definitions of W, t is 1;
R$^{10}$ is selected from the group consisting of —H, -R$^{11}$, —SO$_3$M, —(C=O)R$^{11}$, —SO$_2$NH$_2$, —PO$_3$M'$_2$, -alk—COOR$^{13}$, alk—CON(R$^{11}$)$_2$ and —O-carbohydrate;
R$^{11}$ is independently selected from the group consisting of —H, lower alkyl, cyclic alkyl of 5 to 6 carbon atoms, heterocyclic alkyl of 4 to 5 carbon atoms and 1 to 2 heteroatoms, lower aryl and lower aralkyl;
R$^{12}$ is selected from the group consisting of —N(R$^{11}$)$_2$, and —SR$^{11}$;
R$^{13}$ is selected from the group consiting of R$^{11}$, and M;
R$^{14}$ is selected from the group consisting of —H, and —OR$^{10}$, with the proviso that when z is 2, then together the two R$^{14}$ groups may form a double bond;
R$^{15}$ is independently selected from the group consisting of -R$^{11}$ and —COOH.
M is selected from the group consisting of Na$^+$, K$^+$, Mg$^{2+}$, and Ca$^{2+}$;
M' is selected from the group consisting of —H, —M, and R$^9$; and
X is selected from the group consisting of —O—, —S—, —C(R$^{11}$)$_2$—, and —N(R$^{11}$)—; and pharmaceutically acceptable salts thereof with the provisos that:
(a) when any of R$^1$, R$^2$, R$^3$, R$^4$, R$^5$, R$^6$, R$^7$, and R$^8$ are —Y—B and W is a direct link, then at least one adjacent position must be —OH or an ether moiety;
(b) no more than two of R$^1$, R$^2$, R$^3$, R$^4$, R$^5$, R$^6$, R$^7$, and R$^8$ may be Y—B when W is a direct link;
(c) no more than three of R$^1$, R$^2$, R$^3$, R$^4$, R$^5$, R$^6$, R$^7$, and R$^8$ may be a direct link to A;
(d) only one of R$^1$, R$^4$, R$^5$, and R$^8$ may be a direct link to B;
(e) when one of R$^1$, R$^4$, R$^5$, or R$^8$ is a direct link to B, then at most two of the other naphthyl substituents can be a direct link to A when A is not B;

(f) at most three of $R^1, R^2, R^3, R^4, R^5, R^6, R^7$, and $R^8$ may be independently selected from the group consisting of —OH and ether moieties;

(g) at least one of $R^1, R^2, R^3, R^4, R^5, R^6, R^7$, and $R^8$ is —H;

(h) when any of $R^1, R^4, R^5$, and $R^8$ is a direct link to B, then the adjacent position must be —OH or an ether moiety;

(i) at least one of $R^1, R^2, R^3, R^4, R^5, R^6, R^7$, and $R^8$ is a substituent containing a B group, and at least one is a substituent containing an A group where A is not B; and (j) only when A is directly linked to the naphthyl structure may A be —(C=O)$R^{11}$, and when A is —(C=O)$R^{11}$, at least one adjacent position must be —OH.

A second object of the invention is a description of certain novel medicaments that incorporate newly discovered physical/chemical properties associated with sLe$^x$, such that the medicaments have a three-dimensionally stable configuration for the presentation of the functional groups of sLe$^x$, sialic acid and fucose, that facilitates binding between those groups and the selectins.

A third object of the invention is to provide a composition comprising selectin ligand medicaments bound to a detectable label and/or bound to a pharmaceutically active drug such as an anti-inflammatory drug.

A fourth object of the invention is to provide a pharmaceutical formulation containing selectin ligand medicaments which is useful in treating certain diseases.

A fifth object of the invention is to provide a description of methods to treat or diagnose disease.

A sixth object of the invention is to provide compositions and methods to determine the site of inflammation by administering labeled formulations of the type referred to above.

Another object of the invention is that the ligands can be labeled and the labeled ligands used in an assay to detect the presence of selectins in a sample.

These and other objects, advantages and features of the present invention will become apparent to those persons skilled in the art upon reading the details of the synthesis, structure, formulation and usage as more fully set forth below.

Definitions

In accordance with the present invention and as used herein, the following terms are defined with the following meanings, unless explicitly stated otherwise.

Sialic acids refer to the family of amino sugars containing 9 or more carbon atoms, N- and O-substituted derivatives of neuraminic acid.

Kemp's acid refers to 1,3,5-trimethyl-1,3,5-cyclohexane-tricarboxylic acid, where each acid is axial. N-acetyl neuraminic acid refers to 5-(acetylamino)-3,5-dideoxy-D-glycero-D-galacto-2-nonulosonic acid:

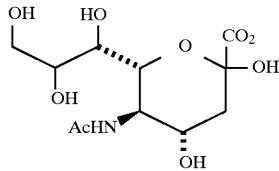

α form refers to standard nomenclature representing the configuration of the anomeric position of an O- or C-glycoside.

β form refers to standard nomenclature representing the configuration of the anomeric position of an O- or C-glycoside.

"Amino" refers to —NR$_2$ where each R is independently selected from —H, lower alkyl, lower aryl, and lower aralkyl.

"Alkyl" refers to saturated hydrocarbons, which may be straight chain, branched, cyclic, or alicyclic. Preferably the alkyl group contains 1 to 10 carbon atoms. Most preferred is 1 to 4 carbon atoms.

"Lower alkyl" refers to branched or straight chain alkyl of 1 to 4 carbon atoms.

"Alkoxy" refers to —OR, where R is an alkyl group. Lower alkoxy refers to —OR where R is lower alkyl.

"Aryl" refers to aromatic groups which have one ring having a conjugated pi electron system and includes carbocyclic aryl, and heterocyclic aryl, both of which may be optionally substituted. Lower aryl refers to an aryl containing up to 6 carbon atoms, and may be optionally substituted.

"Carbocyclic aryl" groups are groups wherein the ring atoms are carbon atoms.

"Heterocyclic aryl" groups are groups having from 1 to 2 heteroatoms in the ring and the remainder of the ring atoms are carbon atoms. Suitable heteroatoms include nitrogen, oxygen, and sulfur. Suitable heterocyclic aryl groups include pyridyl, furanyl, thienyl, pyrrolyl, and the like all optionally substituted. Heteroaryl is the same as heterocyclic aryl.

"Alicyclic" refers to groups which combine the properties of aliphatic and cyclic alkyl groups. For example,

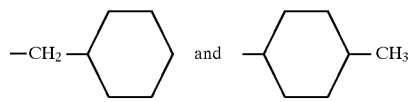

are alicyclic groups.

The term "optionally substituted" aryl groups refers to either no substitution or substitution by one to three substituents independently selected from lower alkyl, halo, carboxylic acids, esters, —NO$_2$, and lower perhaloalkyl.

"Aralkyl" refers to an alkyl group substituted with an aryl group, which may be optionally substituted. Benzyl is a suitable aralkyl group. Lower aralkyl refers to up to and including 8 carbon atoms, and may be optionally substituted. The aralkyl group is attached through the alkyl portion of the group.

"Alkenyl" refers to unsaturated groups which contain at least one carbon-carbon double bond and includes straight-chain, branched chain, and cyclic groups. The double bond may be exo to the chain.

"Alkoxyaryl" refers to aryl substituted with alkoxy group.

"Alkynyl" refers to unsaturated groups which contain at least one carbon triple bond and includes straight-chain, branched chain, and cyclic groups.

"Aryloxy" refers to —O-aryl.

"Aralkoxy" refers to —O-aralkyl.

"Carboxylic acid" refers to —COOH.

"Ester" refers to —COOR where R is lower alkyl, lower aryl, and lower aralkyl;

"Amide" refers to —CONR$_2$ where each R is independently selected from hydrogen, lower alkyl, lower aryl, and lower aralkyl. Preferably at least one R is hydrogen.

"M" refers to a cationic metal selected from Na$^+$, K$^+$, Mg$^{2+}$, and Ca$^{2+}$. Where M is associated with —COO$^-$, it is preferably a plus one cation, and more preferably Na$^+$.

"Protecting group" refers to a group protecting one or several inherent functional groups. Suitable "protecting groups" will depend on the functionality and particular chemistry used to construct the library. Examples of suitable functional protecting groups will be readily apparent to skilled artisans, and are described, for example, in Greene and Wutz, *Protecting Groups in Organic Synthesis*, 2d ed., John Wiley & Sons, NY (1991), which is incorporated herein by reference. Suitable —O-protecting groups can be found in the above book. Preferred such protecting groups include acetate and benzyl.

"Carbohydrate" refers to a chemical moiety comprising the general composition $(C)_n(H_2O)_n$, including, but not limited to glucose, galactose, fucose, fructose, saccharose, mannose, arabinose, xylose, sorbose, lactose, and derivatives thereof, including but not limited to compounds which have other elemental compositions, such as aldonic acids, uronic acids, deoxysugars, or which contain additional elements or moieties, such as amino sugars wherein n is typically 4, 5, 6, 7 atoms and wherein the oxygen atom in the carbohydrate can be replaced by a heteroatom such as nitrogen, sulfur, carbon etc. A carbohydrate as used herein is understood to include chemical structures wherein "H" of any hydroxy group is replaced by any chemically compatible moiety "R", which can be any monomer, oligomer or polymer in the meaning as used herein. Carbohydrates can be saturated or unsaturated. Carbohydrates may be charged or uncharged. Suitable charged carbohydrates include galacturonic acid, glucuronic acid, and sialic acid.

"Carbohydrate unit" is a monomer comprising a monosaccharide.

"Carbon glycoside" is a carbohydrate derivative wherein the anomeric position does not have an oxygen but a carbon substituent.

"Heteroatom glycoside" is a carbohydrate wherein the oxygen at the anomeric position is replaced by an atom other than oxygen, including carbon, nitrogen, sulfur, phosphorous and silicon.

"Identifier tag" is any detectable attribute that provides a means to elucidate the structure of an individual oligomer in a labeled synthetic oligomer library. For example, an identifier tag can be used to identify the resulting products in the synthesis of a labeled synthetic oligomer library.

"Named Reactions" are chemical reactions which are chemical standard reactions known by those of ordinary skill in the art, including but not limited to the Alper Reaction, Barbier Reaction, Claisen-Ireland Reaction, Cope Rearrangement, Delepine Amine synthesis, Gewald Heterocycle Synthesis, Hiyama-Heathcock Stereoselective Allylation, Stork Radical Cyclization, Trost Cyclopentanation, Weidenhagen Imidazole Synthesis. See, in general, Hassner and Stumer, 1994. See, among other places, "Organic Syntheses Based on Named Reactions and Unnamed Reactions", *Tetrahedron Organic Chemistry Series*, edts. Baldwin and Magnus, Pergamon, Great Britain.

"Cope Reaction" or "Cope" refers to the 3, 3 sigmatropic rearrangement and includes the Claisen-Ireland Reaction and all forms of the Cope rearrangement.

"Oligosaccharide" or "polysaccharide" refers to carbohydrates, including carbon glycosides, comprising a plurality of monosaccharides.

"Synthetic chemical library" is a collection of random and semi-random synthetic molecules wherein each member of such library is produced by chemical or enzymatic synthesis.

A "Synthesis support" is a material having a rigid or semi-rigid surface and having functional groups or linkers. A synthesis support may be capable of being derivatized with functional groups or linkers that are suitable for carrying out synthesis reactions.

Such materials will preferably take the form of small beads, pellets, disks, capillaries, hollow fibers, needles, solid fibers, cellulose beads, pore-glass beads, silica gels, polystyrene beads optionally cross-linked with polyethylene glycol divinylbenzene, grafted co-poly beads, polyacrylamide beads, latex beads, dimethylacrylamide beads optionally cross-linked with N,N'-bis-acryloyl ethylene diamine, glass particles coated with a hydrophobic polymer, or other convenient forms.

"Transformation event" or "Reaction" is any event that results in a change of chemical structure of a compound, monomer, an oligomer or polymer. A "transformation event" or "reaction" may be mediated by physical, chemical, enzymatic, biological or other means, or a combination of means, including but not limited to, photo, chemical, enzymatic or biologically mediated isomerization or cleavage, photo, chemical, enzymatic or biologically mediated side group or functional group addition, removal or modification, changes in temperature, changes in pressure, and the like. Thus, "transformation event" or "reaction" includes, but is not limited to, events that result in an increase in molecular weight of a monomer, an oligomer or polymer, such as, for example, addition of one or a plurality of monomers, addition of solvent or gas, or coordination of metal or other inorganic substrates such as, for example, zeolities. A "transformation event" or "reaction" may also result in a decrease in molecular weight of an oligomer or polymer, such as, for example, de-hydrogenation of an alcohol to an alkene or enzymatic hydrolysis of an ester or amide. "Transformation events" or "reaction" also include events that result in no net change in molecular weight of a monomer, an oligomer or polymer, such as, for example, stereochemistry changes at one or a plurality of a chiral centers, Claissen rearrangement, Ireland rearrangement, or Cope rearrangement and other events as will become apparent to those skilled in the art upon review of this disclosure.

"Heterocyclic alkyl" refers to a cyclic alkyl group in which one to three of the ring atoms are a heteroatom and the remaining ring atoms are carbon atoms. Suitable heteroatoms are nitrogen, oxygen, and sulfur. Suitable heterocyclic alkyl groups are morpholine, piperadine, and piperazine.

"Adjacent position" refers to the next carbon atom on the naphthyl ring. For example, $R^3$ and $R^1$ are adjacent to $R^2$, in the naphthyl structure depicted below:

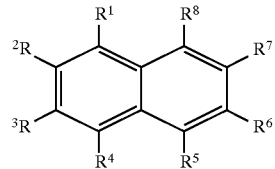

$R^1$ and $R^{11}$ are not considered adjacent positions.

"Naphthyl structure" refers to the bicyclic aromatic group above.

"Ether moiety" refers to any substituent or group linked through an oxygen. For example, $—O(CH_2)_nB$, $—O(CH_2)_nA$, and $—O(CH_2(C=(R^{11})_2)CH_2—B$, and alkoxy are ether moieties.

"—Ar—" refers to a phenyl, optionally substituted.

"—alk—" refers to an alkyl linking group which is selected from lower alkyl, and cycloalkyl. Suitable "—alk—" groups include $—C(CH_3)_2—$, and

"Halo" refers to halogen atoms —F, —Cl, —Br, and —I.

"Cycloalkyl" refers to cyclic alkyl groups and include cyclopropyl, cyclopentyl, cyclohexyl, and cycloheptyl.

The term "pharmaceutically acceptable salt" includes salts of compounds of formula I derived from the combination of a compound of this invention and an organic or inorganic acid or base. The compounds of formula I are useful in both the free acid and salt form.

BRIEF DESCRIPTION OF THE DRAWINGS

This invention may be better understood and its numerous objects, advantages and features will become apparent to those skilled in the art by reference to the accompanying drawings as follows.

DETAILED DESCRIPTION OF THE INVENTION

Figure 1:
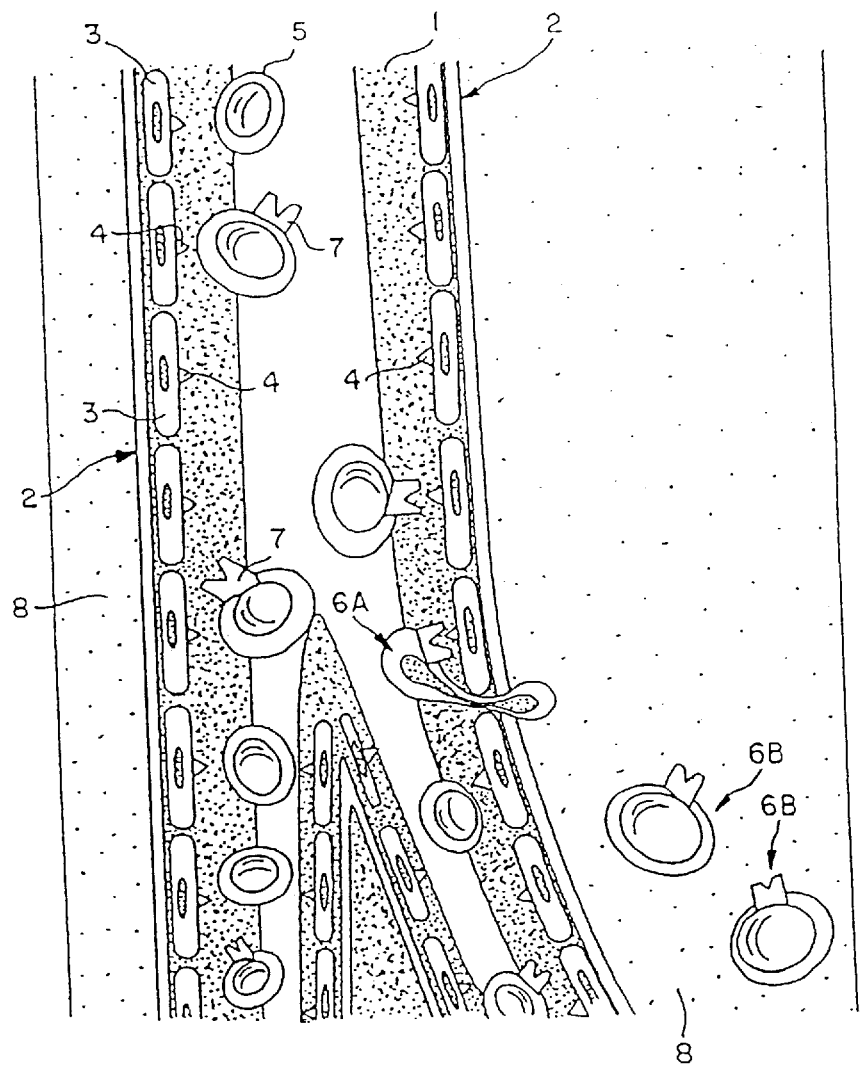
FIG. 1 is a longitudinal schematic view showing the interaction between white blood cells and activated endothelial cells.

Throughout the description of the invention reference is made to certain publications including scientific articles and patents or patent applications. It is the intent that each of these publications be incorporated by reference in their entirety when referred to in the specification.

Before describing the present invention it is to be understood that this invention is not limited to the particular compositions, methods or processes described as such compositions and methods may, of course, vary.

As used in this specification and the appended claims, the singular forms "a", "an" and "the" include the plural unless the context clearly dictates otherwise. Thus, for example, reference to "a tethered compound" includes mixtures of such compounds, reference to "an E-selectin", "a P-selectin", or "an L-selectin" includes reference to respective mixtures of such molecules, reference to "the formulation" or "the method" includes one or more formulations, methods and/or steps of the type described herein and/or which will become apparent to those persons skilled in the art upon reading this disclosure.

Some standard abbreviations used in connection with the present invention include: BSA, bovine serum albumin; DEAE, diethylaminoethyl; DMSO, dimethylsulfoxide; DMF, N,N-dimethylforamide; DCE, dichloroethane; E-selectin or ELAM-1, endothelial/leukocyte adhesion molecule-1; HPTLC, high performance thin layer chromatography; L-selectin or LECAM-1, leukocyte/endothelial cell adhesion molecule-1; MOPS, 3-[N-Morpholino)-propanesulfonic acid; NANA, N-acetylneuraminic acid; PVC, polyvinylchloride; TLC, thin layer chromatography; TFA, trifluoro-acetic acid; Tris, tris (hydroxy-methyl) aminomethane.

Development of the Invention

It is worth noting that while the invention compounds were selected for their capacity to bind to certain selecting, and that therefore this property contributes to their medical activity, it cannot, however, be excluded that they are also exerting their favorable medical effects, either in parallel or in tandem, through additional mechanisms of action. Thus, the skilled practitioner of this art will appreciate that a key aspect of the subject invention is the description of novel medicaments, and that Applicants intend not to be bound by a particular mechanism of action that may account for their prophylactic or therapeutic effects.

E-selectin has a lectin like domain that recognizes the Sialyl Lewis x (sLe$^x$) tetrasaccharide epitope as shown below in Structure III.

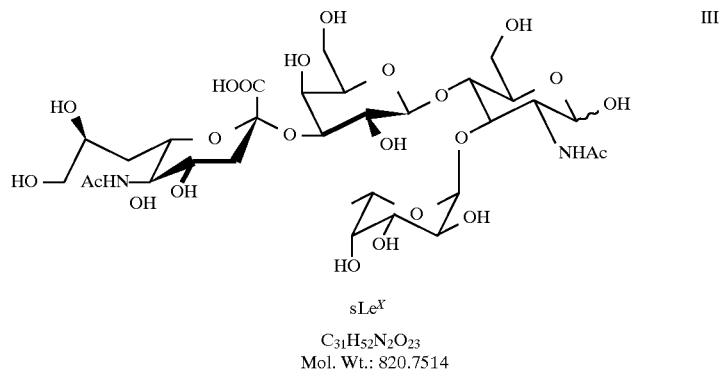

sLe$^x$ $C_{31}H_{52}N_2O_{23}$
Mol. Wt.: 820.7514

The ability of sLe$^x$ to bind E-selectin is described by Lowe et al., Cell (1990) 63:475; Phillips et al., Science (1990) 250–1130; Walz et al., Science (1990) 250:1132; and Tyrrell et al., Proc. Natl. Acad. Sci, USA (1991) 88:10372.

It has also been shown (Berg et al., J. Biol. Chem. (1991) 265:14869; Handa et al., Biochem. Biophys. Res. Commun. (1991) 181:1223) that both E-selectin and P-selectin recognize the isomeric tetrasaccharide sLe$^a$ shown below as Structure IV.

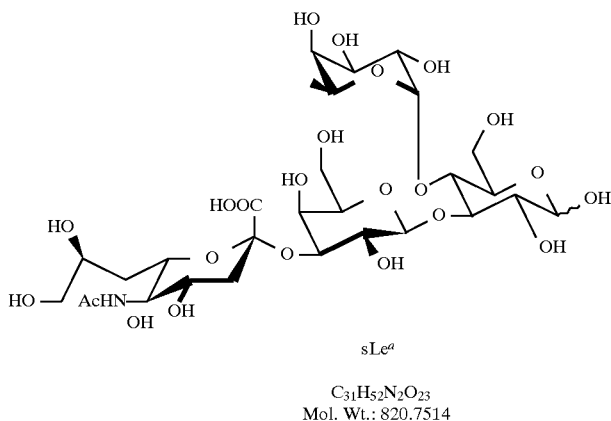

sLe$^a$

C$_{31}$H$_{52}$N$_2$O$_{23}$
Mol. Wt.: 820.7514

L and P-selectin also bind to sLe$^x$ containing ligands, although these selectins have specificity toward a wider variety of natural ligands containing sialylated and sulfated Le$^x$, and Le$^a$ structures as well as other sulfated or charged carbohydrates (Varki et al. *Proc. Nat'l Acad. Sci. USA* 91:7390–7397 (1994).

A key step in developing the compounds of the present invention was the realization that both sLe$^x$ and sLe$^a$ share a structural similarity in their three dimensional arrangements.

Specifically, we observed that sialic acid and fucose, two functional epitopes in these tetrasaccharides, are juxtaposed in space in a way suitable for recognition by the selecting. Most importantly, for both tetrasaccharides we identified 4 to 12 atoms associated with the lactose core of the tetrasaccharides that functionally separate sialic acid from fucose. We postulated that replacement of these atoms would lead to compounds, such as those described and claimed herein, that maintain their selectin binding activity. While 4 to 12 is the preferred number of atoms, most preferred is 6 to 8 atoms as shown in the figure below. The number of atoms refers to the number of atoms between the O-glycoside of sialic acid and the O-glycoside of fucose.

For instance, a close structural examination of sLe$^x$ (shown in III) or a modification thereof wherein R=OH (sLe$^x$Glc) indicates that the epitopes i.e., α-Neu5Ac and L-Fucose, are linked through six atoms (Nos. 1–6) or eight atoms (Nos. i–viii) as shown in Structure III (a) below We have also shown that sLe$^x$ and sLe$^a$ present the fucose and sialic acid functionalities in a special relationship placing them on a single face with a spacing of 10–12 Å measured between the carbonyl carbon of the carboxylic acid on sialic acid and the C-3 of fucose. Rao et al. *J. Bio. Chem.* 269(31):19663 (1994).

The compounds of the present invention possess an acid functionality mimic which is preferably 8–14 Å, and more preferably 9–11 Å from a fucose or fucose mimic. This distance is measured from the carbonyl carbon of the acid mimic to the C-3 carbon of fucose or its equivalent on its mimic.

Additionally, we postulated that replacement of the lactose core with a partially or completely rigid core, while still juxtaposing the two functional epitopes in space in a way suitable for recognition by the selectins, would lead to compounds, such as those described and claimed herein, that maintain their selectin binding activity. The Naphthyl family of compounds offer considerable diversity and facility in terms of attachment of suitable groups to satisfy the spacial requirements for selectin ligand binding.

Using these insights, we then designed certain selectin ligands. This has been done by attaching sialic acid and L-fucose as such, or analogs, suitable derivatives, or mimics thereof, through six or eight atoms to provide a series of compounds shown as structural formula I. This series of compounds is designed to competitively inhibit selectins from binding to their natural ligands. These compounds can be combined with pharmaceutically acceptable excipients to provide pharmaceutical compositions useful in a wide range of treatments.

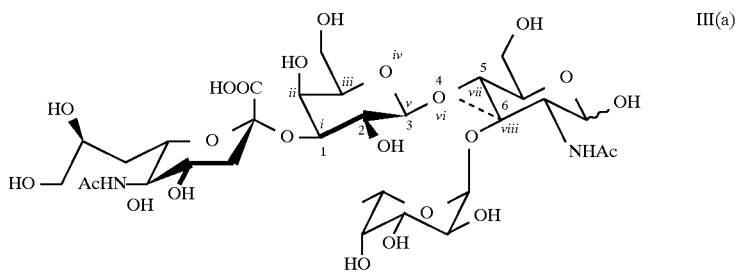

III(a)

wherein R is —NHAc or —OH.

Based on this discovery, we deduced that the corresponding epitopes on the lectin domain of the selectins, are spaced in a similar three-dimensional configuration such that maintenance of the 6 to 8 atoms in the ligand structure would yield active ligands that are markedly different in structure from the naturally occurring ligand.

Applicants believe that the carboxylic acid portion of sialic acid is important for binding. Thus, mimics of sialic acid include moieties containing carboxylic acids, esters and amides. It also includes a vinylagous acid which can mimic the acid functionality, such the group shown below:

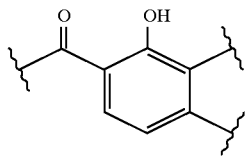

Other sialic acid mimics, also referred to as "A" in the general description, can be in the form of moieties containing sulfates, sulfonates, phosphates, phosphonates, sulfonamides, nitrates, other carboxylic acid equivlanents, and the like. Other acid mimics include B groups, particularly B groups which contain acids and sulfates.

The compounds of the present invention are designed to provide a three-dimensionally stable configuration for functional groups on sialic acid and fucose moieties or their analogues or mimics so as to allow for binding between those functional groups and receptors on natural selectins. The compounds are represented by the following general structural formula I:

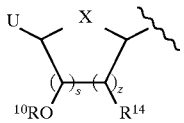

wherein $R^1$, $R^2$, $R^3$, $R^4$, $R^5$, $R^6$, $R^7$, and $R^8$ are independently selected from the group consisting of
(a) —H, Y—B, alkyl of 1 to 4 carbon atoms optionally substituted with 1 to 2 lower alkyl groups, —W((CH$_2$)$_n$—B)$_t$, —W((CH$_2$)$_m$—(CHR$^9$)$_q$—(CH$_2$)$_m$—A)$_t$; —OH, lower alkoxy, lower aryloxy, lower aralkoxy, lower alkoxyaryl, amino, —W((CH$_2$)$_r$—A)$_t$, —O—CH$_2$—C≡C—B, —N(Ac)—CH$_2$—C≡C—B, —NH—CH$_2$—C≡C—B, —N(CH$_2$—C≡C—B)$_2$, —N(Ac)CH$_2$Ar—B, —NHCH$_2$Ar—B, —N(CH$_2$Ar—B)$_2$, —OCH$_2$Ar—B, —(C=O) (CH$_2$)$_m$—B,
(b) a direct link to A, and a direct link to B; where Y—B is selected from the group consisting of

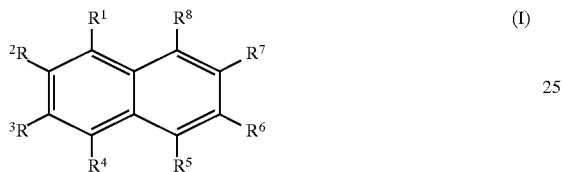

A is selected from the group consisting of —(C=O)R$^{11}$, sialic acid, Kemp's acid, quinic acid, —B, —SO$_3$M, —OSO$_3$M, —SO$_2$NH$_2$, —PO$_3$M'$_2$, —OPO$_3$M'$_2$, —NO$_2$, saturated or unsaturated carboxylic acids of 1 to 4 carbon atoms, optionally substituted with 1 to 2 hydroxyl groups, and esters, and amides thereof;

W is selected from the group consisting of a direct link, —O—, —N<, —S—, —NH—, and —NAc—;

B is

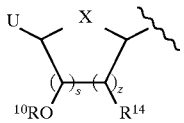

wherein
U is selected from the group consisting of -R$^9$, —CH$_2$OR$^{10}$, —CH$_2$O-protecting group, —COOR$^{11}$, —CON(R$^{11}$)$_2$, and —COOM;
R$^9$ is lower alkyl;
each n is independently selected from the group 0, 1, 2, and 3;
each m is independently selected from the group 0, 1, 2, 3, and 4;
each q is independently selected from the group 0, 1, and 2;
each s is independently selected from the group 1, 2, and 3;
each z is independently selected from the group 1 and 2;
each t is independently selected from the group 1 and 2, with the proviso that when W is —N<, then t is 2, and for all other definitions of W, t is 1;
R$^{10}$ is selected from the group consisting of —H, -R$^{11}$, —SO$_3$M, —(C=O)R$^{11}$, —SO$_2$NH$_2$, —PO$_3$M'$_2$, -alk—COOR$^{13}$, -alk—CON(R$^{11}$)$_2$ and —O-carbohydrate;
R$^{11}$ is independently selected from the group consisting of —H, lower alkyl, cyclic alkyl of 5 to 6 carbon atoms, heterocyclic alkyl of 4 to 5 carbon atoms and 1 to 2 heteroatoms, lower aryl and lower aralkyl;
R$^{12}$ is selected from the group consisting of —N(R$^{11}$)$_2$, and —SR$^{11}$;
R$^{13}$ is selected from the group consiting of R$^{11}$, and M;
R$^{14}$ is selected from the group consisting of —H, and —OR$^{10}$, with the proviso that when z is 2, then together the two R$^{14}$ groups may form a double bond;
R$^{15}$ is independently selected from the group consisting of -R$^{11}$ and —COOH.
M is selected from the group consisting of Na$^+$, K$^+$, Mg$^{2+}$, and Ca$^{2+}$;
M' is selected from the group consisting of —H, —M, and R$^9$; and
X is selected from the group consisting of —O—, —S—, —C(R$^{11}$)$_2$—, and —N(R$^{11}$)—; and pharmaceutically acceptable salts thereof with the provisos that:
(a) when any of $R^1$, $R^2$, $R^3$, $R^4$, $R^5$, $R^6$, $R^7$, and $R^8$ are —Y—B and W is a direct link, then at least one adjacent position must be —OH or an ether moiety;
(b) no more than two of $R^1$, $R^2$, $R^3$, $R^4$, $R^5$, $R^6$, $R^7$, and $R^8$ may be Y—B when W is a direct link;
(c) no more than three of $R^1$, $R^2$, $R^3$, $R^4$, $R^5$, $R^6$, $R^7$, and $R^8$ may be a direct link to A;
(d) only one of $R^1$, $R^4$, $R^5$, and $R^8$ may be a direct link to B;

(e) when one of $R^1$, $R^4$, $R^5$, or $R^8$ is a direct link to B, then at most two of the other naphthyl substituents can be a direct link to A when A is not B;

(f) at most three of $R^1$, $R^2$, $R^3$, $R^4$, $R^5$, $R^6$, $R^7$, and $R^8$ may be independently selected from the group consisting of —OH and ether moieties;

(g) at least one of $R^1$, $R^2$, $R^3$, $R^4$, $R^5$, $R^6$, $R^7$, and $R^8$ is —H;

(h) when any of $R^1$, $R^4$, $R^5$, and $R^8$ is a direct link to B, then the adjacent position must —OH or an ether moiety;

(i) at least one of $R^1$, $R^2$, $R^3$, $R^4$, $R^5$, $R^6$, $R^7$, and $R^8$ is a substituent containing a B group, and at least one is a substituent containing an A group where A is not B; and (j) only when A is directly linked to the naphthyl structure may A be —(C=O)$R^{11}$, and when A is —(C=O)$R^{11}$, at least one adjacent position must be —OH.

The structures that contain the appropriate reactive functions can be reacted with suitably protected hydrophobic carriers like ceramide or a ceramide mimic, steroids, diglycerides or phospholipids to form other medically useful molecules.

The compounds can act as antagonist ligand molecules, i.e. biochemical blocking agents by binding to selectins and preventing circulating leukocytes from binding to endothelial cells, thereby preventing a primary event involved in certain diseases, including cancer, and particularly metastatic cancers, conditions associated with acute inflammation, such as reperfusion injury, septic shock, hypovolemic or traumatic shock, ARDS, and chronic inflammation diseases such as rheumatoid arthritis and asthma. Agonist ligands have the opposite effect.

The compounds of structural formula I can be bound to known drugs, for example anti-inflammatory drugs so as to target the drug-selectin ligand complex to a particular site of disease. Additionally, they can be formulated to provide compositions useful in assaying a sample for the presence of selectins such as E, L and/or P-selectin, or to detect the site of inflammation in a patient, or to treat acute inflammation (or treating the inflammatory symptoms of certain diseases) or other diseases involving the interaction of selectins on appropriate cell types.

Preferred $R^1$, $R^2$, $R^3$, $R^4$, $R^5$, $R^6$, $R^7$, and $R^8$ groups include

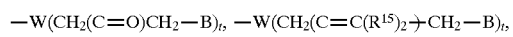

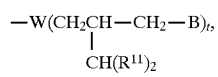

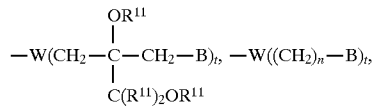

—W(CH$_2$—CR$^{11}$(OR$^{11}$)CH$_2$—B)$_t$, —OH, lower alkoxy, lower aryloxy, lower aryloxy, lower alkoxyaryl, —H, a direct link to A where A is not B, and a direct link to B; where W is a direct link or —O—, and t is 1.

Most preferred are

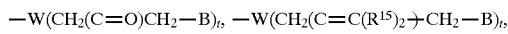

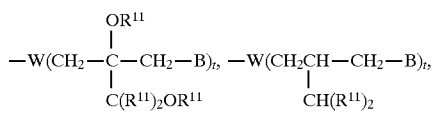

—W(CH$_2$—CR$^{11}$(OR$^{11}$)CH$_2$—B)$_t$, —OH, —H, and a direct link to A where A is not B.

The preferred examples of A and B are shown respectively in formula V and VI. Other examples of A include α or β or other analogues or derivatives of sialic acid other than the N-acetyl neuraminic acid residue shown in formula V, Kemp's acid, quinic acid, R and S forms of mandelic acid, R and S forms of glyceric acid, R and S forms of lactic acid, propionic and acetic acid, and esters and amides thereof, —SO$_3$, —PO$_3$. The synthesis of certain analogues of sialic acid is described in U.S. Pat. No. 5,138,044.

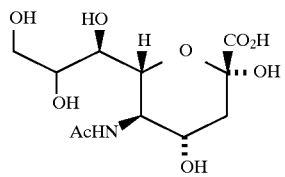

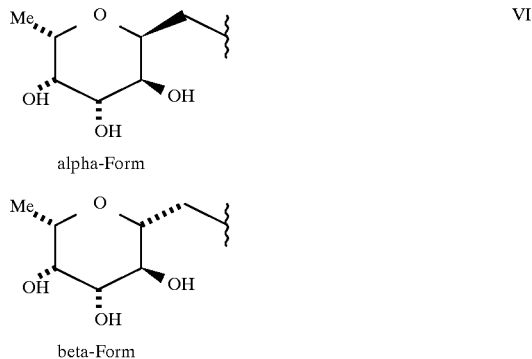

alpha-Form beta-Form

Preferred embodiments of the ligands of the invention are those wherein the substituent represented by A or B is an N-acetylneuramyl residue and B is fucose.

Preferred forms of B are the α and β forms of L-fucose as shown in formula VI. The moiety B also includes substituted forms of the following α and β-fucose structure VI:

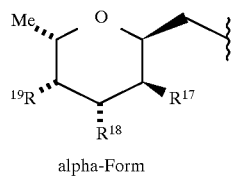

alpha-Form

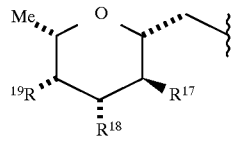

beta-Form wherein Me is a methyl group, $R^{17}$, $R^{18}$ and $R^{19}$ are each independently —OH, —F, —N(R$^9$)$_2$ (wherein R$^9$ is lower alkyl). Other moieties for B include modified fucosides such as corresponding carboxylic analogues of fucose; inositol; substituted inositol; imidazole; substituted imidazole; benzimidazole; substituted benzimidazole; Guanidine; pentaerythritol; substituted pentaerythritol; and substituted butanes of the formula —CH$_2$—CHR$^{17}$—CHR$^{18}$—CH$_2$R$^{19}$ wherein R$^{12}$, R$^{18}$, and R$^{19}$ are independently —OH, —F or —N(R$^9$)$_2$.

Preferred B groups include those where s is 1 or 2, R$^{14}$ is —H or —OH, X is —O—, U is —CH$_2$OR$^{10}$ or -R$^9$, and R$^{10}$ is -alk—COOH, —SO$_3$M, —H, or -alk—COOM. Most preferred are those where s is 2. Particularly preferred B groups include fucose, galactose, mannose, and arabinose.

Preferred s numbers are 1 and 2. Most preferred is 2.
Preferred q numbers are 0 and 1.
Preferred m numbers are 0 and 1.
Preferred n numbers are 0 and 3.
Preferred z numbers are 1.

Preferred R$^{10}$ groups are —H, SO$_3$M, -alk—COOR$^{13}$, and —O-carbohydrate. Most preferred are —H, —SO$_3$M, and -alk—COOR$^{13}$.

Preferred R$^{11}$ groups are —H, lower alkyl, and lower aralkyl. Most preferred is —H.

A preferred R$^{12}$ group is —N(R$^{11}$)$_2$.
Preferred R$^{14}$ groups are —H and —OH.
Preferred R$^{15}$ groups are —COOH, —H, and —CH$_3$.
A preferred M cation is Na$^+$.
Preferred M' groups are —H, Na$^+$, and —CH$_3$.
A preferred X group is —O—.
Preferred U groups are —CH$_2$OR$^{10}$ and -R$^9$.
Preferred —W(CH$_2$(C═C(R$^{15}$)$_2$)—CH$_2$—B)$_t$, groups are those where W is a direct link or —O—, t is 1, and R$^{15}$ is independently —H, —CH$_3$, and —COOH.

In one preferred aspect, R$^3$ and R$^6$ are selected from the group consisting of —SO$_3$M, —OSO$_3$M, —NO$_2$, and —CO$_2$H, and at least one of R$^1$, R$^2$, or R$^7$ is selected from the group OH and —NH$_2$.

In another preferred aspect, R$^1$ is a direct link to B, R$^2$ and R$^3$ are selected from the group consisting of

—OH,

—W(CH$_2$(C═O)CH$_2$—B)$_t$, —W(CH$_2$(C═C(R$^{15}$)$_2$)─CH$_2$—B)$_t$, $$-W(CH_2-\underset{\underset{C(R^{11})_2OR^{11}}{|}}{\overset{\overset{OR_{11}}{|}}{C}}-CH_2-B)_t, \text{ and}$$

—W(CH$_2$CH—CH$_2$—B)$_t$, and
     |
     CH(R$^{11}$)$_2$

—W(CH$_2$—CR$^{11}$(OR$^{11}$)CH$_2$—B)$_t$ where W is a direct link and t is 1, R$^7$ is —H or —OH, and R$^6$ is selected from the group consisting of —H and —(CH$_2$)$_m$—(CHR$^9$)$_q$—(CH$_2$)$_m$—A, where each m and q are independently selected from 0 or 1, and A is a saturated or unsaturated carboxylic acid of 1 to 4 carbon atoms, optionally substituted with 1 to 2 hydroxy groups, and esters and amides thereof. More preferred is where in the B group s is 1 or 2, R$^{14}$ is —H or —OH, X is —O—, U is —CH$_2$OR$^{10}$ or -R$^9$, and R$^{10}$ is -alk—COOH, —SO$_3$M, —H, or -alk—COOM. Also preferred is where R$^{15}$ is —H.

Preferred compounds include those prepared in the Examples and those found in Table 1.

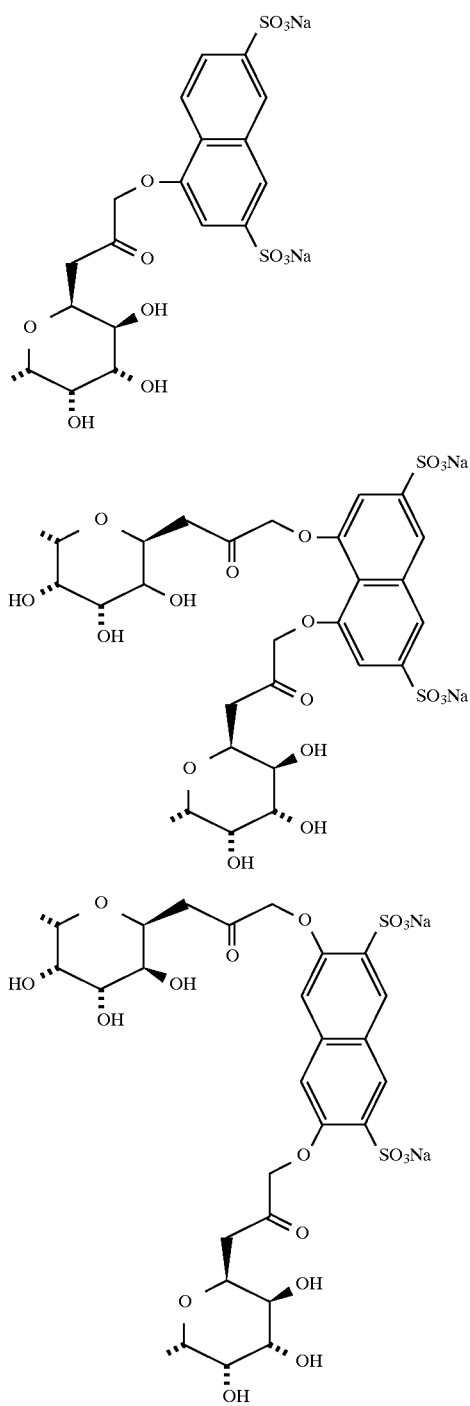

Assaying Compounds of Formula I

The compounds of formula I can be tested for their ability to bind to a selectin receptor and/or block the binding site of the receptor and thereby prevent a natural ligand from binding to the selectin receptor. A generalized procedure for testing the compounds of formula I is given below.

An ELISA assay is preferably used that employs recombinant fusion proteins composed of extracellular portions of the human selectins joined to human immunoglobulin heavy chain CH$_3$, CH$_2$, and hinge regions. See, for example, Walz et al., Science (1990) 250:1132; Aruffo et al., Cell (1991) 67:35; Aruffo et al., Proc. Natl. Acad. Sci. USA (1992) 89:2292. The assay is well known in the art, and generally consists of the following three steps: I. 2,3 sLe$^x$ glycolipid (25 picomole/well) was transferred into microliter wells as solutions and then evaporated off. Excess, which remained unattached, was washed off with water. The wells were then blocked with 5% BSA at room temperature for an hour and then washed with PBS containing 1 mM calcium. II. Preparation of "multivalent" receptor of the Selectin-IgG chimera was carried out by combining the respective chimera (1 μg/mL) with biotin labelled goat F(ab')$_2$ anti-human IgG (Fc specific) and streptavidin-alkaline phosphatase diluted 1:1000 in 1% BSA-PBS (1 mM calcium) and incubating at 37° C. for 15 min. This allowed the soluble multivalent receptor complex to form. III. Potential inhibitors such as the compounds of formula I were allowed to react with the soluble receptor at 37° C. for 45 min. This test assumes that optimal binding, between the soluble phase receptor complex and the inhibitor (non natural ligand), would have occurred within this time frame. This solution was then placed in the microliter wells that were prepared in step I. The plate was incubated at 37° C. for 45 minutes to allow the soluble receptor to bind to its natural ligand. In the presence of a strong inhibitor only a few receptors should be free to bind to the microliter plate coated with the natural ligand.

The positive control is the signal produced by the soluble receptor when it is allowed to react with 2,3 sLe$^x$ glycolipid in the microliter wells in the absence of any inhibitor. This was considered 100% binding. The signal produced by the receptor that had been previously treated with an inhibitor (recorded as O.D.), was divided by the signal produced by the positive control and multiplied by 100 to calculate the % receptor bound to the well in the presence of the inhibitor. The reciprocal of this is the % inhibition.

It is important to note that invention compounds include those having sialic acid and fucose separated by 4–12 atoms, or sialic acid or analogs, derivatives or mimics of sialic acid separated by 4–12 atoms bound to fucose or analogs, derivatives or mimics thereof.

Referring now to FIG. 1, a longitudinal view of a blood vessel 1 is shown. The vessel wall 2 is lined internally with endothelial cells 3. The endothelial cells 3 can be activated causing the cells 3 to synthesize E or P-selectin which is displayed in FIG. 1 as a triangular surface receptor 4. Both red blood cells 5 and white blood cells (6A, 6B) flow in the vessel 1. The white blood cells 6 display carbohydrate ligands 7 which have chemical and physical characteristics which allow the ligands 7 to bind to the receptors 4. Once the ligand 7 binds to the receptor 4, the white blood cell 6 is brought through the vessel wall 2 as is shown with the white blood cell 6A. The white blood cells 6B brought into the surrounding tissue 8 can have positive effects, such as fighting infection, and negative effects, such as inflammation.

Figure 2:
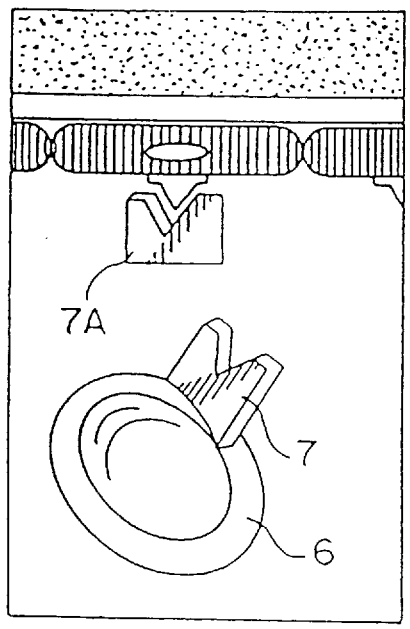
FIG. 2 is a longitudinal schematic view showing how compounds of the invention would be used as pharmaceuticals to block selectin ligand interactions.

An important aspect of the present invention can be described by referring to FIG. 2. The compounds of formula I are shown as 7A and can adhere to a selectin such as E, L and/or P-selectin by themselves and can be formulated into pharmaceutical compositions, which when administered will effectively block the E, L and/or P-selectin and prevent the adhesion of a ligand 7 connected to a white blood cell 6. By administering pharmaceutically effective amounts of the compounds 7A, some, but not all, of the white blood cells will not reach the surrounding tissue. By slowing the rate at which the white blood cells reach the surrounding tissue, inflammation can be prevented and/or alleviated.

The selectin family of adhesion molecules participate in acute inflammation by initiating neutrophil rolling on activated endothelial cells. This is particularly evident in studies of ischemia reperfusion injury, where P-selectin appears to be important in neutrophil recruitment to damaged tissue. The presence of L-selectin and E- or P-selectin ligands on mononuclear cells has implicated these receptor-ligand interactions in chronic inflammation. This has been supported by the finding of chronic expression of E-selectin in dermatologic conditions, and P-selectin expression on joint synovial endothelium derived from rheumatoid arthritis patients. L. Lasky *Annu. Rev. Biochem.* 64:113–39 (1995); "Selectin Family of Adhesion Molecules" by Michael Forrest and James C. Paulson in Physiology and Pathophysiology of Leukocyte Adhesion, Ed. by D. Niel Grangier and Deert Schmid-Schönbein, Oxford University Press, New York, N.Y. (1995).

The compounds of formula I may also be labeled using standard radioactive, fluorescent, enzymic or other labels for analytical or diagnostic purposes.

In order for a ligand of the invention to bind to a selectin receptor such as E, L and/or P-selectin receptor the ligand need not include the identical atoms in the identical configuration as per structural formula I but must have (1) a relatively stable three dimensional conformation as shown in formula I, or (2) a substantially equivalent configuration to that shown in formula I. The equivalency of any other ligand will relate to its physical three dimensional structure and the electron configuration of the molecule, and in particular the charge related characteristics presented by the groups present on the A and B moieties shown in formulae V and VI.

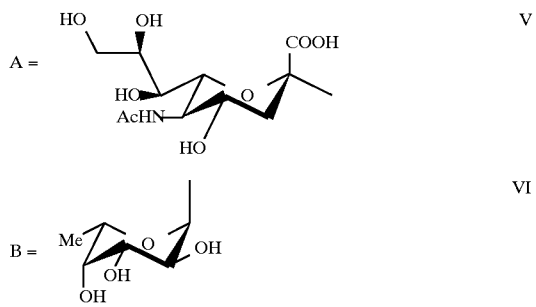

Assay to Identify Ligand (General)

Candidate ligands can be assayed for their ability to adhere to E, L or P-selectin. The method comprises attaching candidate ligands of formula I to a substrate surface and then contacting the substrate surface thereon with recombinant cells, that are genetically engineered to express high levels of E, L or P-selectin, for a sufficient time to allow the cells to adhere to the substrate bearing the candidate ligand. Thereafter, centrifugal force or other appropriate methodology is applied so as to separate away the cells which do not adhere to the substrate. Candidate ligands which adhere to E, L or P-selectin, respectively, are determined via the labels on the cells. Such molecules are isolated, characterized, and their structure specifically identified.

Radiolabeled COS cells expressing cell surface E, L and/or P-selectin can be used as probes to screen compounds of the invention. E, L or P-selectin transfected COS cells will adhere to a subset of compounds of the invention which can be resolved on TLC plates or adsorbed on PVC microliter wells. Adhesion tests are preferably done under physiological conditions. Adhesion to these compounds may require calcium, but will not be inhibited by heparin, chondroitin sulfate, keratin sulfate, or yeast phospho-mannan (PPME). Monosaccharide composition, linkage analysis, and FAB mass spectrometry of 5 of the purified compounds will indicate that the ligands for E, L or P-selectin share common structural characteristics which generally relate to the moieties A and B and the position in which they are held.

Identification of Compounds Which Act as E, L and/or P-selectin Ligands Using Recombinantly Produced Receptor A complete cDNA for the E, L and/or P-selectin receptor was obtained by PCR starting with total RNA isolated from IL-1 stimulated human umbilical vein endothelium. The resulting cDNA was inserted into the CDM8 plasmid (see Aruffo et al., *Proc. Natl Acad. Sci. USA* (1987) 84:8573) and the plasmid amplified in *E. coli*. Plasmid DNA from individual colonies was isolated and used to transfect COS cells. Positive plasmids were selected by their ability to generate COS cells that support HL-60 cell adhesion. DNA sequencing positively identified one of these clones as encoding for E, L and/or P-selectin (Bevilacqua et al., *Science*, (1989) 243:1160; Polte et al., *Nucleic Acids Res* (1990) 18:1083; Hession et al., *Proc. Natl. Acad. Sci. USA* (1990) 87:1673). These publications are incorporated herein by reference for their disclosure of E-selectin and genetic material coding for its production. The complete nucleotide sequence of the E-selectin cDNA and predicted amino acid sequence of the E-selectin protein are given in the above cited article by Bevilacqua et al., which DNA and amino acid sequences are incorporated herein by reference (see also published PCT patent application WO90/13300 which was published Nov. 15, 1990, which is incorporated herein by reference).

COS cells, expressing membrane-bound E, L and/or P-selectin, were metabolically radiolabeled with $T_2PO_4$ (tritiated phosphoric acid). These labeled cells can be used as probes in two assay systems to screen for recognition of the compounds of formula I. More specifically, compounds of formula I may be adsorbed to the bottoms of PVC microliter wells or resolved on TLC plates. In either assay the compounds may be probed for their ability to support adhesion of E, L and/or P-selectin-transfected COS cells, untransfected COS cells, or COS cells transfected with a plasmid containing an irrelevant cDNA, under conditions of controlled detachment force (see Swank-Hill et al., *Anal. Biochem.* (1987) 183:27; and Blackburn et al., *J. Biol. Chem.* (1986) 261:2873 each of which is incorporated herein by reference to disclose the details of such assaying methodology).

NSAID or non-steroidal, anti-inflammatory drugs such as naproxen or ibuprofen which act as anti-inflammatory agents could be administered bound to the modified ligand and could be administered systemically in smaller amounts than usual while obtaining an equivalent effect or even greater anti-inflammatory effect at the site of inflammation. Any other drugs which might be attached include, but are not limited to, antibiotics, vasodilators and analgesics. Such a drug delivery system would reduce any systemic effect normally caused by the drug in that the drugs could be administered in amounts of one-half to one-tenth the normal dose and still obtain the same anti-inflammatory result at the site of inflammation.

UTILITY

The invention compounds have considerable utility for the treatment of certain diseases, as set forth herein. However, this is not their only utility. Another utility is identification of particular chemical moieties that are responsible for, or contribute to ligand binding to the different selecting. Using the selectin binding assays described herein it is readily determined which chemical moieties that make up a selectin ligand contribute to selectin binding.

It is believed that the compounds of the present invention can be used to treat a wide range of diseases, including diseases such as rheumatoid arthritis and ultiple sclerosis. The compositions of the invention hould be applicable to treat any disease state wherein the immune system turns against the body causing the white cells to accumulate in the tissues to the extent that they cause tissue damage, swelling, inflammation and/or pain.

The inflammation of rheumatoid arthritis, for example, is created when large numbers of white blood cells quickly enter the joints in the area of disease and attack the surrounding tissues.

Formulations of the present invention might also be administered to prevent the undesirable after effects of tissue damage resulting from heart attacks. When a heart attack occurs and the patient has been revived, such as by the application of anticoagulants or thrombolytic (e.g., tPA), the endothelial lining where a clot was formed has often suffered damage. When the antithrombotic has removed the clot, the damaged tissue beneath the clot and other damaged tissue in the endothelial lining which has been deprived of oxygen become activated. The activated endothelial cells then synthesize the E-selectin receptors within hours of the cells being damaged. The receptors are extended into the blood vessels where they adhere to glycolipid ligand molecules on the surface of white blood cells. Large numbers of white blood cells are quickly captured and brought into the tissue surrounding the area of activated endothelial cells, resulting in inflammation, swelling, and necrosis which thereby decreases the likelihood of survival of the patient.

In addition to treating patients suffering from the trauma resulting from heart attack, patients suffering from actual physical trauma could be treated with formulations of the invention in order to relieve the amount of inflammation and swelling which normally result after an area of the body is subjected to severe trauma. Other disease states which might be treatable using formulations of the invention include adult respiratory distress syndrome and various types of arthritis and asthma. After reading the present disclosure, those skilled in the art will recognize other disease states and/or symptoms which might be treated and/or mitigated by the administration of formulations of the present invention.

Radiolabeled compounds of the invention may be prepared in a sterile, non-pyrogenic medium and injected into the bloodstream of a patient at a dose to be determined in the usual way by the physician or radiologist. After a sufficient period for a good balance to have been reached between (i) specificity of binding to activated endothelium compared to non-specific distribution and (ii) total amount of compound on activated endothelium, the compound is imaged in a conventional way, according to the nature of the label used. Use of radiolabelled compounds of the invention could be used to diagnose disease, such as the site of inflammation.

The compounds of the invention could also be used as laboratory probes to test for the presence of a selectin receptor such as a receptor of E, L and/or P-selectin in a sample. Such probes are preferably labeled such as with a radioactive label. There are a number of known labels including radioactive labeled atoms, e.g. radioactive C, O, N, P, or S, fluorescent dyes and enzyme labels which can be attached to compounds of the invention using known procedures. Labels as well as methods of attaching labels to sugar moieties are disclosed in U.S. Pat. No. 4,849,513 issued Jul. 18, 1989 to Smith et al. which patent is incorporated herein by reference to disclose labels and methods of attaching labels.

Method of Synthesis (General)

The compound of formula I can be made using the general and specific synthesis schemes and examples described below. However, those skilled in the art will recognize variations thereof which are intended to be encompassed by the present invention. In general, the A and B moieties of formula I are connected and held in a desired three-dimensional configuration. The compounds of the present invention can be prepared in a number of ways. The following schemes show one preferred method of preparing the compounds of the present invention. Scheme 1 shows the attachment of a B group to the naphthyl structure.

Scheme 2 shows further elaboration of the naphthyl structure by attachment of another B group through an ether linker. Class I electrophiles are alkyl halide C-glycosides. Class II electrophiles are allylic halide C-glycosides Class II electrophiles form allylic ethers. "Sugar" refers to C-glycosides below.

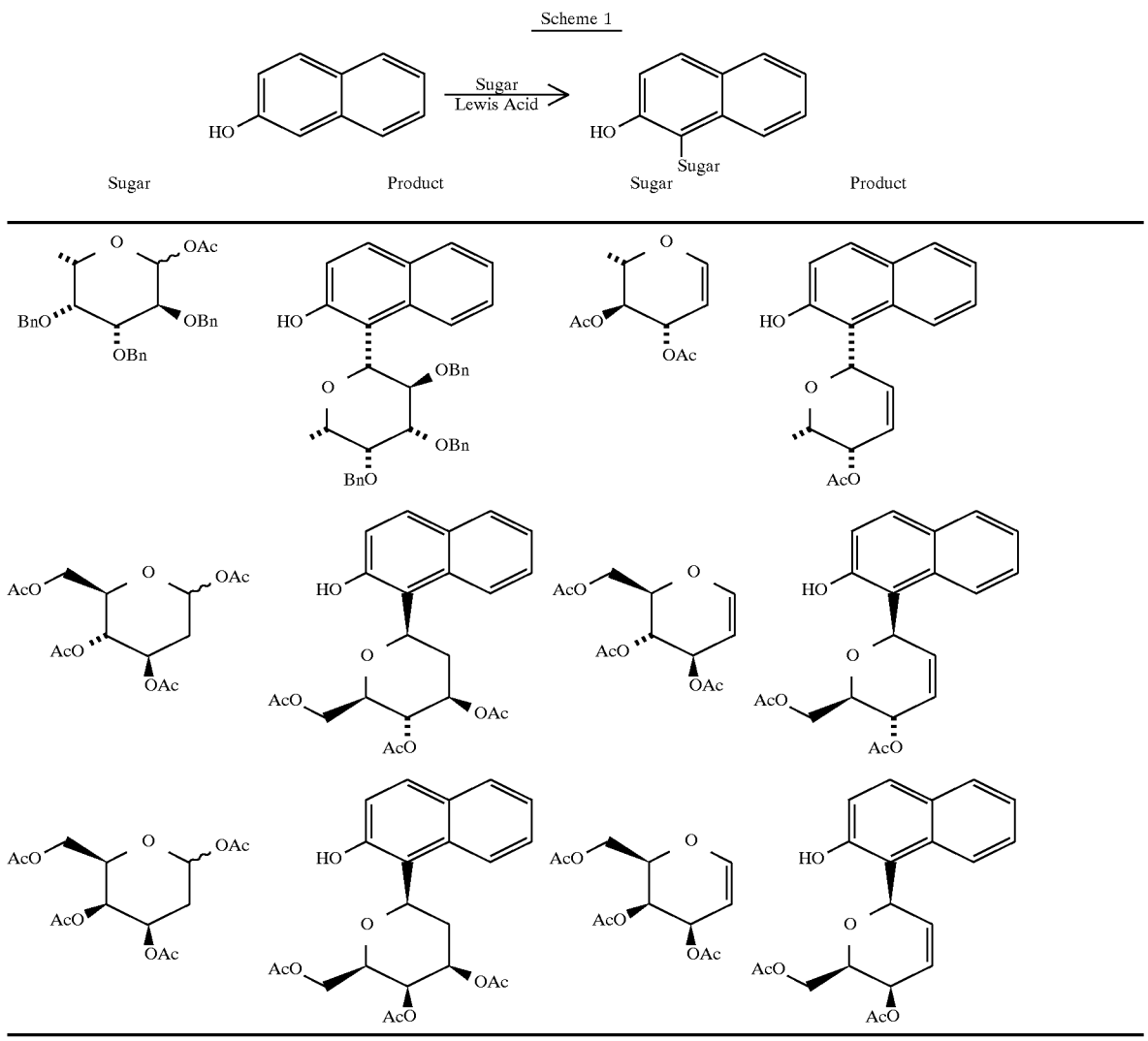

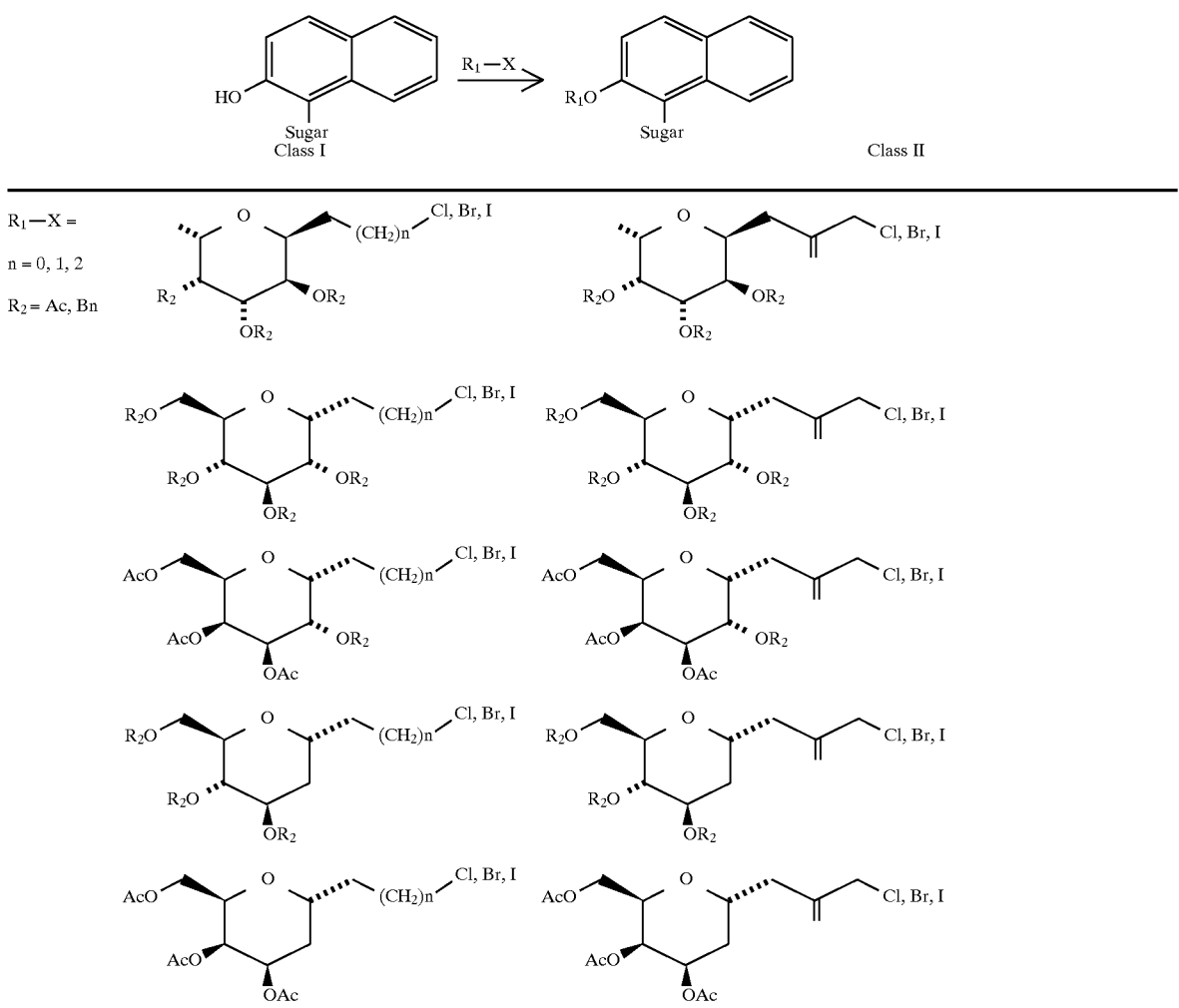

Scheme 3 shows the Claisen Ireland rearrangement of the allylic ether to form a trisubstituted naphthyl structure where the second B group, "sugar$_2$" is attached through an alkene linker.

Scheme 3

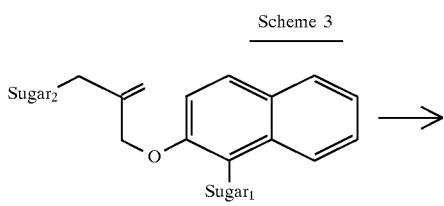

→

-continued

Scheme 3

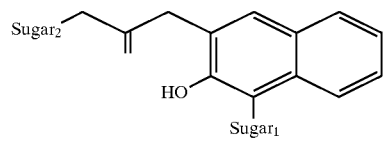

Scheme 4 shows several methods of introducing functionality to a sugar. In all three products, the Sugar, has been functionalized so that this B group acts as an acid moiety.

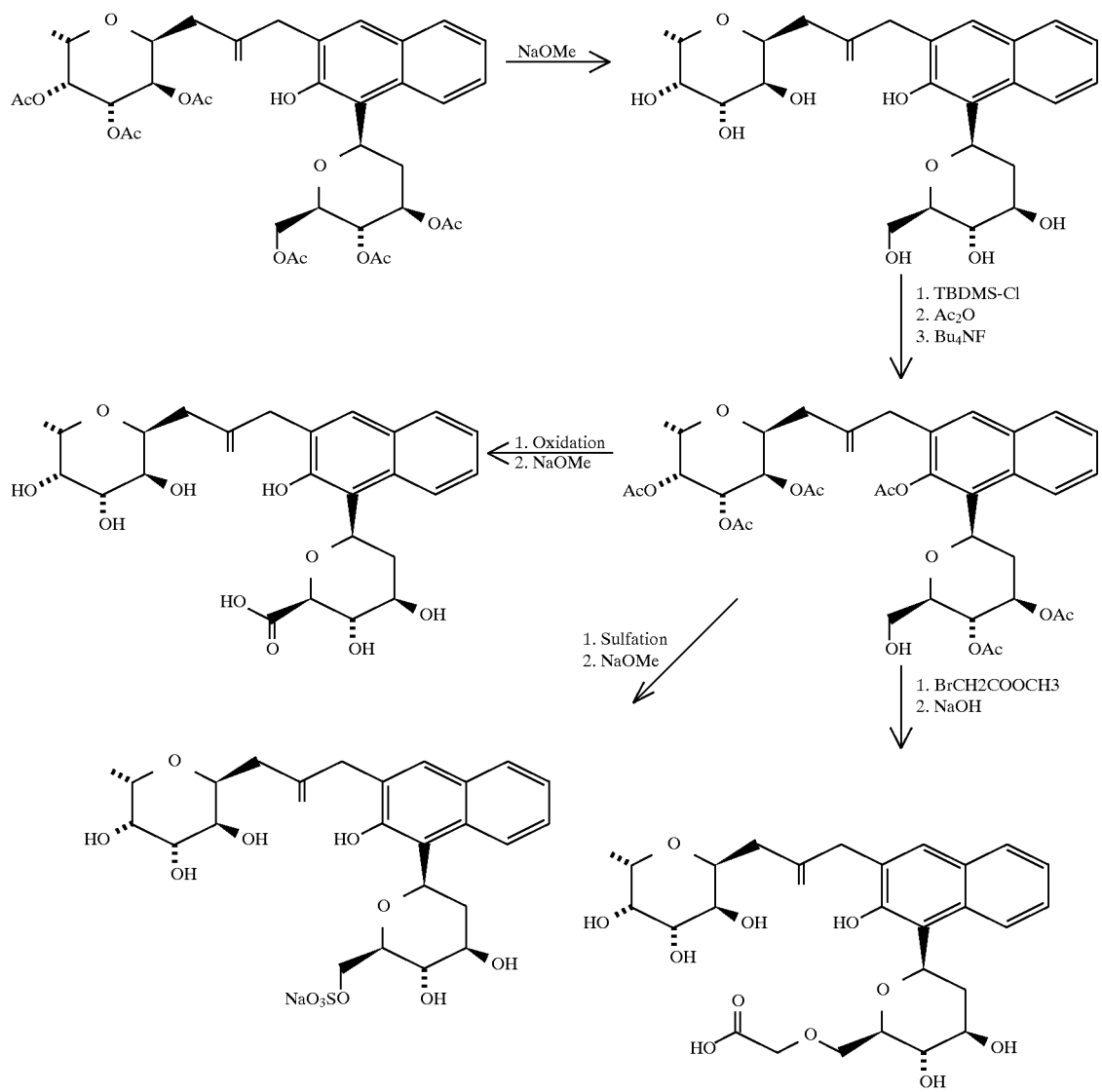
Scheme 5 shows another method of introducing acidic functionality onto a sugar.

Scheme 5

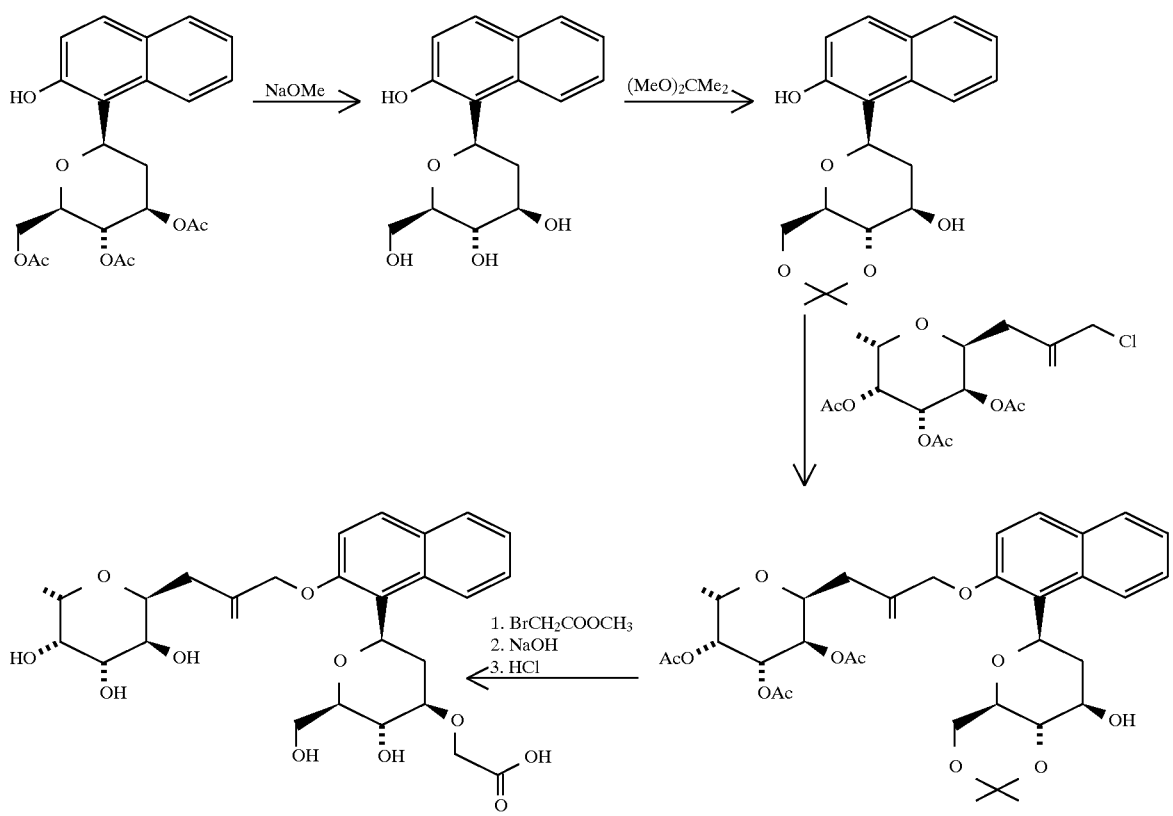

Schemes 1–5 also apply to compounds where the naphthyl is replaced by a phenyl or flavanoid structure.

The compound shown above can then be reacted with a fluorescent probe, a multivalent compound, a ceramide, cholesterol or other lipid components, or a pharmaceutically active drug such as an anti-inflammatory drug.

Synthesis of Carbon Glycosides

A vast array of methods for carbon-carbon bond formation at the anomeric carbon are known in the art, which also can be applied to the formation of other heteroatom glycosides, as carbon-phosphorous, carbon-sulfur, carbon-nitrogen, or carbon-silicon bonds at the anomeric position which are understood to be within the invention. The most common method for carbon-carbon bond formation at the anomeric carbon involves nucleophilic attack on this electrophilic center. A wide variety of electrophilic sugars have been employed, such as reducing sugars (or lactols), alkyl glycosides, anomeric esters, glycosyl halides, imidates, anomeric trichloroacetimidates, glycals, lactones, thioglycosides, as well as oxygen-protected glycosides such as acetates and p-nitrobenzoates. The carbon nucleophiles that have been used include silyl enol ethers, alkenes, allylsilanes, allylstannanes, cyanides, homoenolates, and organometallics such as Grignard reagents, organolithiums, cuprates, and aluminates. Further, procedures to synthesize carbon-glycosides based on metals (palladium, manganese, rhodium, and cobalt) have been developed. Concerted reactions such as [4+2] cycloadditions and sigmatropic rearrangements have also been employed to generate carbon glycosides. Also, the Wittig Reaction has extensively been applied to carbon glycoside synthesis, which can be pursued by reaction of hemiacetals followed by ring closure, reaction of sugar lactones, or reaction of anomeric phosphoranes. Other approaches for the synthesis of carbon glycosides encompass, among others, palladium mediated reactions, free radical reactions, and reactions relying on the electrophilic activity of the anomeric center of sugar molecules. Special merits of free radical methods are mild reaction conditions and tolerance of a wide range of functional groups. The subject of carbon-glycoside synthesis has been reviewed by Hanessian and Pernet, 1976, Adv. Chem. Biochem. 33:111; Postema, 1992, Tetrahedron 48:8545; Postema, C-Glycoside Synthesis, 1995, CRC Press, Ann Arbor, Mich. Suhadoluid, 1970, Nucleoside Antibiotics Wiley-Interscience: New York; Daves and Cheng, 1976, Prog. Med. Chem. 13:303; Inch, 1984, Tetrahedron 40:3161; Hacksell and Daves, 1985, Prog. Med. Chem. 22:1; and Buchanan, 1983, Prog. Chem. Org Natl. Prod. 44:243; and Levy and Tang, 1995 "The Chemistry of C-glycosides, Pergamon Press.

The following scheme shows the general chemical reaction underlying the generation of activated carbon glycosides useful for the generation of novel compounds provided by the present invention:

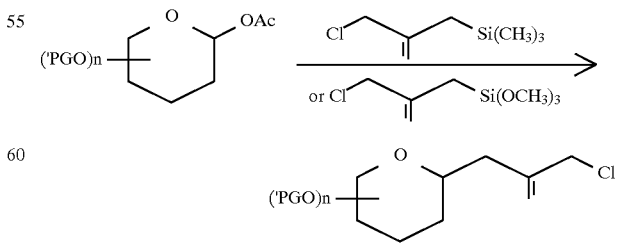

PG denotes a Protecting Group

Reagents effective for the preparation of carbon glycosides include allyltrimethylsilane (Herscovici and Antonakis, 1992, *Nat. Prod. Chem.* 10:337; Postema, 1992, *Tetrahedron* 48:8545; Daves, 1990, *Acc. Chem. Res.* 23:201; Hacksell, 1985, *Progress in Medicinal Chemistry* 22:1; Hanessian and Pernet, 1976, *Adv. Chem. Biochem.* 33:111; *Carbohydrate Chemistry*, Specialist Periodical Reports, Royal Chemical Society, 1968–1990, p. 1–24; preparation of allyl silanes: Anderson and Fuchs, 1987, *Synthetic Commun.* 17:621) and an array of carbon nucleophiles available from commercial sources. Additional examples include, trimethylsilyl enol ethers, allyltrimethylsilane, E- and Z-crotyltrialkylsilanes, organoaluminum reagents, trialkylstannanes, propargylic trialkylstannanes, [1-(acetoxy)-2-propenyl]trimethylsilane, [1-(acetoxy)-2-methyl-2-propenyl]-trimethylsilane, and ethyl-2-propenyltrimethyl-silane-1-carbonate. All are efficient carbon nucleophiles in the field of carbon glycosidation reactions (Panek and Sparks, 1989, *J. Org. Chem.* 54:2034, and references therein). The use of [1-(acetoxy)-2-methyl-2-propenyl]-trimethylsilane reagent provides access to terminally oxygen substituted propenyl groups.

Although carbon glycosides can be produced in a few synthetic transformations, they do not necessarily form suitable carbon glycosides which could easily be used as alkylating agents for the preparation of novel carbohydrate mimics. In one aspect, the present invention provides novel carbohydrate analogues for the preparation of carbohydrate mimetics. Libraries of glycomimetics of complex carbohydrates such as, but not limited, to Sialyl Lewis$^x$ (sLe$^x$) tetrasaccharide can be prepared (Rao et al., 1994, *The Journal of Biological Chemistry* 269:19663; Allanson et al., 1994, *Tetrahedron Asymmetry* 5:2061). One of the advantages of having an allylic halide as an alkylating agent is it would not be prone to E-2 elimination reactions (see, among other places, Lowry and Richardson, Mechanisms and Theory in Organic Chemistry, Second edition, 1981, Harper & Row, New York, p. 530). Among the distinct advantages of this type of novel carbon glycoside is the plethora of new chemical entities created by virtue of the invention.

For example, several terminally substituted halogen carbon glycosides are efficiently obtained from reaction of 2-chloromethyl-3-trimethylsilyl-1-propene or 2-chloromethyl-3-trimethoxysilyl-1-propene with an activated carbohydrate when the reaction is catalyzed by Lewis acid. Thereby, the allylsilanes can undergo a stereochemically controlled axial addition to the pyranose oxonium ions produced by Lewis acid catalysis and anomeric acetates. Benzyl protected carbohydrates result in a stereoselective and efficient route to A-C-glycosides, incorporating an allylic chloride. The use of the per-O-acetylated carbohydrates offers added versatility by avoiding the hydrogenolysis step required for O-benzyl protected sugars. Nashed and Anderson, 1982, *J. Amer Chem. Soc.* 104:7282; Panek and Sparks, 1989, *J. Org. Chem.* 54:2034.

2-Chloromethyl-3-trimethylsilyl-1-propene and 2-chloromethyl-3-trimethoxysilyl-1-propene reagents react with benzyl protected carbohydrates with equal efficiency while per-O-acetylated carbohydrates show better results with the 2-chloromethyl-3-trimethylsilyl-1-propene reagent. Examples for the carbon glycoside synthesis as employed by the subject invention are provided by the instant disclosure, infra. Both the α- and the β- configuration are part of the invention.

Methods for the Generation of Novel Compounds Comprising Carbon Glycosides

The tools and methods of the present invention are focused towards the incorporation of carbohydrates into existing and novel organic compounds, and combinatorial chemical libraries.

The carbohydrate moieties employed for the generation of such naphthyl compounds and libraries include monomers, dimers, trimers, oligomers, branched or unbranched, linked to a suitable functional group of a chemical moiety comprising such functional group. Suitable functional groups include, but are not limited to, phenolic, hydroxyl, carboxyl, thiol, amido, and amino groups. In the case a moiety has more than one such suitable functional group, one or more such functional groups may be protected by suitable protecting groups during the coupling reaction. Such protecting groups include lower methyl-, benzyl-, benzoyl-, acetyl-, MOM, MEM, MPM, tBDMS, or TMS groups. After the coupling reaction, the protecting groups may selectively be removed.

In all cases, every molecule comprising at least one suitable functional group can be employed as substrate to react with the activated carbon glycosides/heteroatom glycosides of the present invention.

Protecting Groups

The monomers of the present invention, i.e., the carbohydrates used for the formation of carbon glycosides, the carbon glycosides, and/or the substrates may have groups protecting part of the functional groups within the monomer. Suitable protecting groups will depend on the functionality and particular chemistry used to generate the novel compound or combinatorial chemical library. Examples for suitable functional protecting groups will be readily apparent to those of ordinary skill in the art, and can be found, among other places, in Greene and Wutz, 1991, *Protecting Groups in Organic Synthesis*, 2d ed., John Wiley & Sons, N.Y. Protecting groups typically used when modifying the anomeric position of carbohydrates are apparent to one of ordinary skill in the art. In addition, a plurality of functional groups may be employed. The C-atom of the carbohydrate used for the formation of the carbon glycosidic bond can be modified by differential protection of functional groups, as it will be apparent to those of ordinary skill in the art. Most preferred protecting groups of the present invention comprise benzyl- and acetyl-groups.

Coupling Reactions

Carbon glycoside reagents can be functionalized to be used in a plethora of chemical reactions in order to form unique compounds. Suitable functionalized carbon glycosides can be attached, for example, to phenolic, hydroxyl, carboxyl, thiol, amino, amido, and/or equivalent functionality under mild conditions. Activated forms of C-glycosides are alkylhalide, alkenyl halide, or some equivalent activated form. The coupling reactions for activated C-glycosides can be performed to form novel compounds under standard conditions typically used for alkyl and alkenyl chlorides, bromides, iodides, acetates, alcohols, Grignards, etc. In addition, the alkenyl C-glycosides offer routes into Cope rearrangements, Claisen rearrangements, and allylic couplings, as they are readily known by those of ordinary skill in the art and as are described in various examples provided hereinbelow to form novel glycomimetics and unique compounds.

Many named standard reaction conditions using allylic halides parallel the use of carbon glycosides containing allylic halide functionality to prepare novel compounds and functional groups, including but not limited to the Alper Reaction, Barbier Reaction, Claisen-Ireland Reaction, Cope Rearrangement, Delepine Amine synthesis, Gewald Heterocycle Synthesis, Hiyama-Heathcock Stereoselective Allylation, Stork Radical Cyclization, Trost Cyclopentanation, Weidenhagen Imidazole Synthesis. See, in general, Hassner and Stumer, 1994, "Organic Syntheses Based on Named Reactions and Unnamed Reactions", *Tetrahedron Organic Chemistry Series*, edts. Baldwin and Magnus, Pergamon, Great Britain.

One of ordinary skill in the art will appreciate that the methods of the present invention can be used to incorporate carbohydrate units or analogues thereof in virtually any naphthyl based structure. In the case where a substrate Naphthyl structure comprises more than one suitable functional group to react with the functionalized C-glycosides of the present invention, these functionalities need not be identical.

Interconversion of Alkenyl Linkers

The alkenyl C-Glycoside compounds described and utilized here are of particular utility due to the reactivity of the activated alkenyl C-glycoside reagent, and the diverse array of transformations and functional group modifications possible around the alkenyl moiety. The scheme below illustrates some of the more common transformations that can be applied to these structures, with the understanding that many additional modifications are possible to one of ordinary skill in the art.

The common transformations described above are generally known to one skilled in the art and the methodologies described, and equivalent methodologies are available in advanced organic chemistry textbooks, and references cited therein. For some general references to these chemistries please see the appropriate Example.

Claisen-Ireland Rearrangement: General Example.

The rearrangement of allyl aromatic ethers to ortho or para allylaromatic alcohols, or the rearrangement to adjacent positions relative to the alkylated phenol moiety, can be accomplished in a two step format. The first step is to alkylate the phenol, which can be done using the procedure herein disclosed or by using the optional procedure used in the following example using sodium methoxide. The result is the o-alkylated napthols.

The alkylated naphthols can then be refluxed in the appropriate solvent such as dimethylaniline or 1,2-dichlorobenzene for 3–12 hours (depending on the substrate) to give the Claisen-Ireland product.

Claisen-Ireland Rearrangement: 2-Naphthol Example.

The rearrangement of allyl naphthol ethers to ortho or para allylphenols can be accomplished in a two step format.

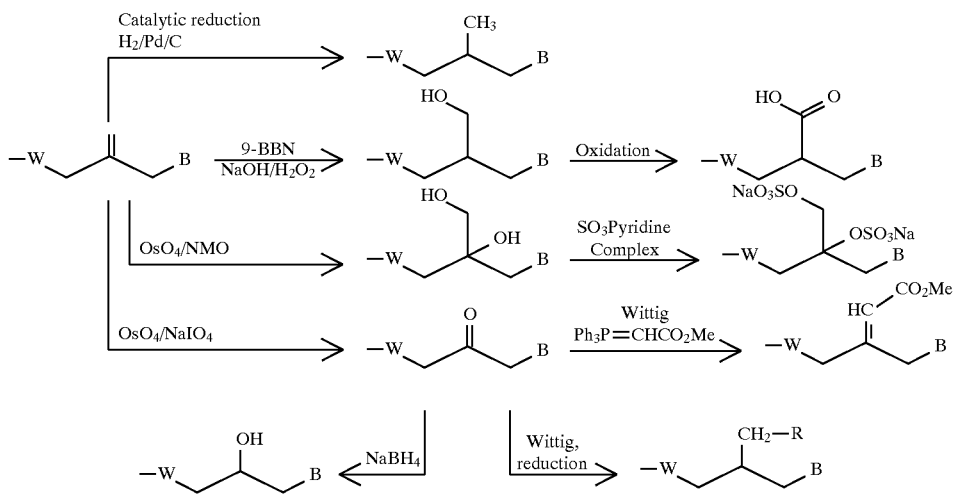

As illustrated in the above scheme, the alkenyl moiety is easily converted to the saturated substituted alkyl form using standard catalytic hydrogenation conditions as found in advanced organic chemistry reference textbooks. Treatment of the alkene with 9-BBN followed by treatment with basic hydrogen peroxide, or equivalent conditions, provided the primary alcohol derivative. Oxidation of the alcohol using known conditions would provide the carboxylic acid analog. The vicinal diol derivative can be prepared by oxidation with osmium tetra oxide and NMO or similar bishydroxylation conditions as described in standard texts on organic chemistry. The ketone derivative can be made from diol by oxidative cleavage reaction conditions including periodate oxidation. Alternately, the ketone can be prepared by direct treatment of the alkene with osmium tetroxide and periodate. The ketone can then provide the secondary alcohol by reduction with reducing agents such as sodium borohydride.

The diol group described above is suited to a variety of O-alkylation and O-acylation reactions, with O-sulfation being a particularly useful method for introducing anionic functionality into the linker. The ketone can undergo subsequent modifications via wittig reactions as described to yield the substituted alkene groups, or following reduction by catalytic hydrogenation, yielding substituted alkyl linker groups.

The first step is to alkylate the phenol, which can be done using the procedures herein disclosed.

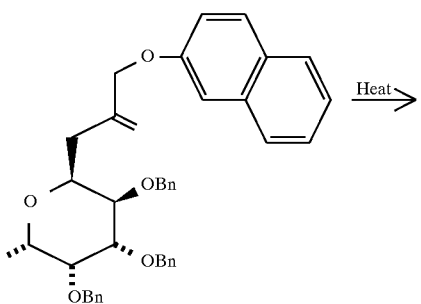

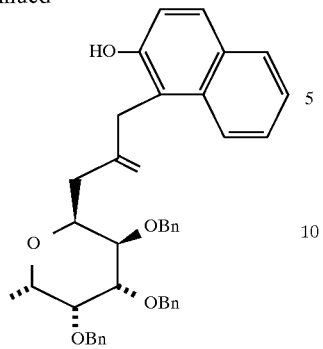

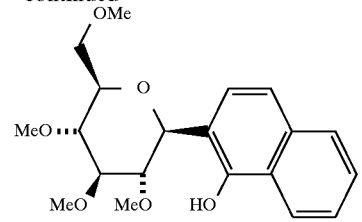

The allylic naphthol is refluxed in dimethylaniline or dichlorobenzene for 3–12 hours to give the 1-(allyl-2,3,4-tri-O-benzyl-alpha-C-Fucoside)-2-naphthol.

Aromatic Nucleophiles: The O-C Migration.

The O to C rearrangement of O-phenyl glycosides has been reported to generate aromatic C-glycosides (M.H.D. Postema, C-Glycoside Synthesis, CRC Press, page 2–42, c1995, CRC Press, Inc., ISBN 0-8493-9150-4, Ann Arbor, Mich., and references therein). Kometani and collaborators (T. Kometani, H. Kondo, Y. Fumimori, Synthesis, 1005, (1988)) have used the O to C migration for the preparation of aromatic C-glycosides. Its use in the preparation of sLex mimics and its use in conjunction with the Claisen-Ireland rearrangement contained in this application is new. When these compounds are exposed to a Lewis acid, the rearrangement takes place to give the beta-aryl-C-glycoside. Typically, beta isomer is the major component. In these reactions, the regioselectivity of 2-naphthols gives the C-glycoside at the 1-position while the 1-naphthols give the C-glycoside at the 2-position. Using this methodology in conjunction with the Claisen-Ireland type of rearrangements gives novel compounds of the invention.

Example (Kometani, et al):

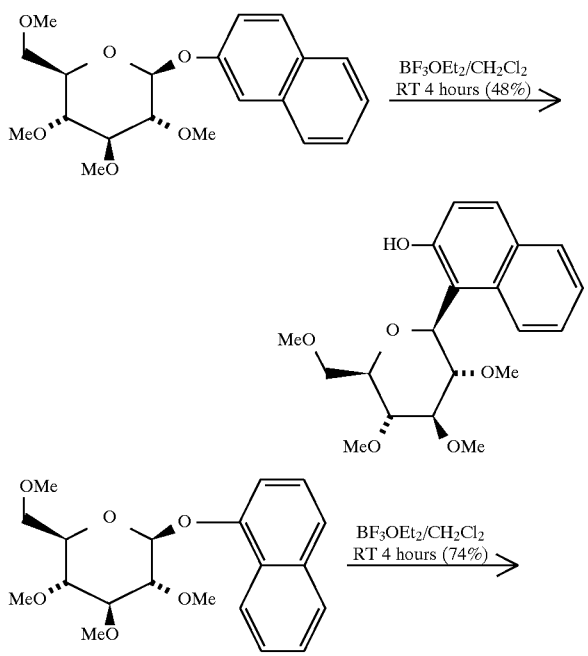

Use and Administration

The compounds of the invention such as various ligands of structural formula I can be administered to a subject in need thereof to treat the subject by either prophylactically preventing inflammation or relieving it after it has begun. The ligands are preferably administered with a pharmaceutically acceptable carrier, the nature of the carrier differing with the mode of administration, for example, oral administration, usually using a solid carrier and I.V. administration a liquid salt solution carrier. The formulation of choice can be accomplished using a variety of excipients including, for example, pharmaceutical grades of mannitol, lactose, starch, magnesium stearate, sodium saccharin cellulose, magnesium carbonate, and the like. Oral compositions may be taken in the form of solutions, suspensions, tablets, pills, capsules, sustained release formulations, or powders. Particularly useful is the administration of the compounds directly in transdermal formulations with permeation enhancers such as DMSO. Other topical formulations can be administered to treat dermal inflammation.

A sufficient amount of compound(s) would be administered to bind to a substantial portion of the selectin expected to cause or actually causing the disease, for example, inflammation so that inflammation can either be prevented or ameliorated. Thus, "treating" as used herein shall mean preventing or ameliorating the appropriate disease. Typically, the compositions of the instant invention will contain from less than 1% to about 95% of the active ingredient, preferably about 10% to about 50%. Preferably, between about 10 mg and 50 mg will be administered to a child and between about 50 mg and 1000 mg will be administered to an adult. The frequency of administration will be determined by the care given based on patient responsiveness.

Other effective dosages can be readily determined by one of ordinary skill in the art through routine trials establishing dose response curves.

When determining the dose of compounds to be administered which block selectin receptors, it must be kept in mind that one may not wish to completely block all of the receptors. In order for a normal healing process to proceed, at least some of the white blood cells or neutrophils must be brought into the tissue in the areas where the wound, infection or disease state is occurring. The amount of the ligands administered as blocking agents must be adjusted carefully based on the particular needs of the patient while taking into consideration a variety of factors such as the type of disease that is being treated.

Other modes of administration will also find use with the subject invention. For instance, the ligand molecules of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

The compounds of the instant invention may also be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Compounds of formula I can be mixed with compatible, pharmaceutically acceptable excipients. Suitable vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those of ordinary skill in the art. See, e.g. Remington's Pharmaceutical Sciences, Mack Publishing Company, Easton, Pa., 17th edition, 1985. The composition or formulation to be administered will, in any event, contain a quantity of the compounds adequate to achieve the desired state in the subject being treated.

The various compounds of the present invention can be used by themselves or in combination with pharmaceutically acceptable excipient materials as described above. However, the compounds of the invention can be made as conjugates wherein they are linked in some manner (e.g., via the $R^1$ moiety) to a label. By forming such conjugates, the compounds can act as biochemical delivery systems for the label so that a site of disease can be detected.

For instance, carbohydrates can be labelled by a variety of procedures, for example: esterification of hydroxyl bonds to form a structure capable of complexing directly with a radioisotope or NMR enhancer; reaction of the carbohydrate with amino diacetic acid (IDA) in organic solvent to form an N-linked glycoside derivative which would be capable of complexing with a radioisotope via the nitrogen and oxygen atoms of the IDA group; or coupling of the carbohydrate to amino acids which may be labelled directly (e.g. cysteine, tyrosine) or labelled via a bifunctional chelating agent (e.g., lysine).

Appropriate radioactive atoms would include, for example, technetium 99m ($^{99m}$Tc), iodine-123 ($^{123}$I) or indium-111 ($^{111}$In) for scintigraphic studies, or for nuclear magnetic resonance (NMR) imaging (also known as magnetic resonance imaging, MRI), a label such as gadolinium, manganese or iron, or a positron-emitting isotope such as iodine-124, fluorine-19, carbon-13, nitrogen-15 or oxygen-17.

EXAMPLES

The compounds of this invention and their preparation can be understood further by the following examples which illustrate some of the processes by which these compounds are prepared. The following examples are provided so as to provide those of ordinary skill in the art with a complete disclosure and description of how to make compounds and compositions of the invention and are not intended to limit the scope of what the inventors regard as their invention. The compounds of the present invention can be prepared by methods now known or later developed. Unless indicated otherwise, parts are parts by weight, temperature is in degrees C, and pressure is at or near atmospheric.

Materials and Methods

Reagents were purchased from commercial suppliers such as Pfanstiehl Laboratories, Aldrich Chemical Company or Lancaster Synthsis Ltd. and were used without further purification unless otherwise indicated. Tetrahydrofuran (THF) and dimethylformamide (DMF) were purchased from Aldrich in sure seal bottles and used as received. All solvents were purified by using standard methods readily known to those of ordinary skill in the art unless otherwise indicated.

General Protocol

The reactions set forth below are done generally under a positive pressure of nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed on glass-backed silica gel 60 F 254 plates Analtech (0.25 mm) and eluted with the appropriate solvent ratios (v/v) which are noted where appropriate. The reactions were assayed by TLC and terminated as judged by the consumption of starting material.

Visualization of the TLC plates were done with a p-anisaldehyde spray reagent or phosphomolybdic acid reagent (Aldrich Chemical 20% wt in ethanol) and activated with heat. Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ prior to filtration and evaporation of the solvents under reduced pressure on a rotary evaporator and noted as solvents removed in vacuo.

Flash column chromatography (Still et al., 1978, A.J. Org. Chem. 43:2923) was done using Baker grade flash silica fel (47–61 mm) and a silica gel: crude material ratio of about 20:1 to 50:1 unless otherwise stated.

Hydrogenolysis can be done at the pressure indicated in the examples, or at ambient pressure.

$^1$H-NMR spectra were recorded on a Varian 300 instrument operating at 300 MHz and $^{13}$C-NMR spectra were recorded on a Varian 300 instrument operating at 75 MHz. NMR spectra were obtained as $CDCl_3$ solutions (reported in ppm), using chloroform as the reference standard (7.25 ppm and 77.00 ppm) or $CD_3OD$ (3.4 and 4.8 ppm and 49.3 ppm) or internally tetramethylsilane (0.00 ppm) when appropriate. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz.

Infrared spectra were recorded on a Perkin-Elmer FT-IR Spectrometer as neat oils, or a $CDCl_3$ solutions, and are reported in wave numbers ($cm^{-1}$).

The mass spectra were obtained using LSIMS. All melting points are uncorrected. Microanalyses were carried out by Galbraith Laboratories, Inc., Knoxville, Tenn.

Catalytic Reduction

Catalytic Hydrogenation for the Reduction of an Alkene or Removal of the Benzyl Group.

For a compound containing an alkene, 1.00 mmole equivalent is dissolved in an appropriate hydrogenation solvent suitable for the compound to be deprotected. Solvents can include but are not restricted to, methanol, ethyl acetate, ethanol, acetic acid or combinations thereof. For example, methanol with a catalytic amount of acetic acid or ethyl acetate and methanol can be used as the hydrogenation solvent. 5% or 10% palladium on carbon (1 g for every 50 grams of starting material with the catalyst wetted with toluene under argon) is evacuated and hydrogen gas is added and the process repeated three times. The reaction is shaken or stirred for several hours until the deprotection is complete. The reaction can be done under ambient pressures or can be performed using a hydrogenation bomb at appropriate pressures (generally 10–50 psig). The reaction is terminated by removal of the excess hydrogen gas, flushing the reaction vessil with an inert atmosphere and then filtering the contents through Celite to remove the catalyst and washing the catalyst with 30% methanol in chloroform or appropriate solvent system. Concentration in vacuo afforded the desired compound. The product can be purified by column chromatography using Baker grade fresh silica gel (47–61 mm) and a suitable solvent system. For example, 10% ethyl acetate in hexanes and then with 30% ethyl acetate in hexanes. The silica gel is eluted with methanol and checked by TLC for any product material. The solvents are removed in vacuo and the product dried under vacuum. The desired product is recovered.

General references on applicable transformations can be found, among other places, in:

R. C. Larock, Comprehensive Organic Transformations, ISBN 0-89573-710-8, 1989, VCH Publishers, Inc. 220 East 23rd Street, Suite 909, New York, N.Y. 10010.

Jerry March, Advanced Organic Chemistry, 3rd Edition, c1985, ISBN 0-471-88841-9, John Wiley & Sons Publishers, New York USA.

H. O. House, Modern Synthetic Reactions, c1972, ISBN 0-8053-4501-9, The Benjamin/Cummings Publishing Company, Menlo Park, Calif., USA.

F. A. Carey and R. J. Sundberg, Advanced Organic Chemistry Parts A & B, 2nd Edition, c1983, ISBN 0-306-41199-7, Plenum Press, a division of Plenum Publishing Corporation, 233 Spring Street, New York, N.Y. 10013, USA.

9-BBN

For a compound containing an alkene, (1.00 mmole equiv.) is dissolved in an appropriate solvent suitable for the compound to be reduced with 9-BBN (9-borabicyclo[3.3.1] nonane) or equivalent. Solvents can include but are not restricted to, tetrahydrofuran (THF), hexanes and diethyl ether, or combinations thereof. To a stirred solution of the olefin, (1.00 mmole equiv.) in THF (0.5M) at 0° C. is added 9-BBN pre-dissolved in THF (1.00 mmole equiv.) is carefully added. The reaction contents are stirred at 0° C. and the cooling bath (water/ice) is allowed to melt. The reaction is allowed to stir at ambient temperature for 8 hours or until the reaction is complete via analysis by TLC. The reaction is terminated by the careful addition acetone and stirred for 1 hour at room temperature. The reaction contents are cooled to 0° C. and then 1.0M NaOH and 30% $H_2O_2$ are added to decompose the alkyl borate. The contents are stirred until the alkyl borate decomposes to the carbonol. An extraction solvent such as chloroform or ethyl acetate is added and the heterogeneous layers are separated and the organic phase is washed with 1.0M hydrochloric acid, water and brine. The washed product is dried over anhydrous sodium sulfate and filtered. The product can be purified by column chromatography using Baker grade flash silica gel (47–61 mm) and a suitable solvent system. For example, 10% ethyl acetate in hexanes and then with 30% ethyl acetate in hexanes or appropriate solvent mixtures dependant upon the particular substrate used. The silica gel is eluted with methanol and checked by TLC for any product material. The solvents are removed in vacuo and the product dried under vacuum the desired product is recovered.

General references on applicable transformations can be found, among other places, in:

R. C. Larock, Comprehensive Organic Transformations, ISBN 0-89573-710-8, 1989, VCH Publishers, Inc. 220 East 23rd Street, Suite 909, New York, N.Y. 10010.

Jerry March, Advanced Organic Chemistry, 3rd Edition, c1985, ISBN 0-471-88841-9, John Wiley & Sons Publishers, New York USA.

H. O. House, Modern Synthetic Reactions, c1972, ISBN 0-8053-4501-9, The Benjamin/Cummings Publishing Company, Menlo Park, Calif., USA.

F. A. Carey and R. J. Sundberg, Advanced Organic Chemistry Parts A & B, 2nd Edition, c1983, ISBN 0-306-41199-7, Plenum Press, a division of Plenum Publishing Corporation, 233 Spring Street, New York, N.Y. 10013, USA.

Oxidation

General references on applicable transformations can be found, among other places in:

M. Hudlicky, Oxidations in Organic Chemistry, ACS Monograph #186, c1990, ISBN 0-8412-1781-5, Published by The American Chemical Society, Washington, D.C.

R. C. Larock, Comprehensive Organic Transformations, ISBN 0-89573-710-8, 1989, VCH Publishers, Inc. 220 East 23rd Street, Suite 909, New York, N.Y. 10010.

Jerry March, Advanced Organic Chemistry, 3rd Edition, c1985, ISBN 0-471-88841-9, John Wiley & Sons Publishers, New York USA.

H. O. House, Modern Synthetic Reactions, c1972, ISBN 0-8053-4501-9, The Benjamin/Cummings Publishing Company, Menlo Park, Calif., USA.

F. A. Carey and R. J. Sundberg, Advanced Organic Chemistry Parts A & B, 2nd Edition, c1983, ISBN 0-306-41199-7, Plenum Press, a division of Plenum Publishing Corporation, 233 Spring Street, New York, N.Y. 10013, USA.

Bis-Hydroxylation

Bishydroxylation of the olefin via Oxidation with osmium tetroxide. To a stirred solution of the olefin, (1.00 mmole equiv.) in 1% water in acetone (0.5M) at 0° C. is added osmium tetroxide pre-dissolved in acetone (0.01 mmole equiv.) and N-methylmorpholine-N-oxide (2.00 mmole equiv.) is carefully added as a solid. The reaction contents are stirred at 0° C. and the cooling bath (water/ice) is allowed to melt. The reaction is allowed to stir at ambient temperature for 18 hours or until the reaction is complete via analysis by TLC. The reaction can be assayed by TLC or an aliquot of the reaction acetate. The aliquot is checked by $^1$H-NMR in $CDCl_3$. The reaction is terminated by the careful addition of sodium bisulfite (contains a mixture of $NaHSO_3$ and $Na_2S_2O_5$), stirred for 1 hour at room temperature and then water. An extraction solvent such as chloroform is added and the heterogeneous layers are separated and the organic phase is washed with 1.0M hydrochloric acid, water and brine. The washed product is dried over anhydrous sodium sulfate and filtered. The product can be purified by column chromatography using Baker grade flash silica gel (47–61 mm) and a suitable solvent system. For example, 10% ethyl acetate in hexanes and then with 30% ethyl acetate in hexanes. The silica gel is eluted with methanol and checked by TLC for any product material. The solvents are removed in vacuo and the product dried under vacuum the desired product is recovered.

General references on applicable transformations can be found, among other places, in:

R. C. Larock, Comprehensive Organic Transformations, ISBN 0-89573-710-8, 1989, VCH Publishers, Inc. 220 East 23rd Street, Suite 909, New York, N.Y. 10010.

Jerry March, Advanced Organic Chemistry, 3rd Edition, c1985, ISBN 0-471-88841-9, John Wiley & Sons Publishers, New York USA.

H. O. House, Modern Synthetic Reactions, c1972, ISBN 0-8053-4501-9, The Benjamin/Cummings Publishing Company, Menlo Park, Calif., USA.

F. A. Carey and R. J. Sundberg, Advanced Organic Chemistry Parts A & B, 2nd Edition, c1983, ISBN 0-306-41199-7, Plenum Press, a division of Plenum Publishing Corporation, 233 Spring Street, New York, N.Y. 10013, USA.

Sulfation

Sulfation of hydroxyl functionalities. In a preferred embodiment, the hydroxy groups of the target molecule are sulfated under standard conditions: For example, to a solution of 0.35 g 3,4-di-C-fucosyl caffeic acid (0.603 mmole, 1 mmole equiv.) in 7.2 mL pyridine was added 1.15 g sulfur trioxide pyridine complex (7.24 mmole, 12 mmole equiv.) and the reaction was stirred at ambient temperature for 12 hours. The reaction was complete as assayed by TLC at $CHCl_3$:MeOH:$H_2O$ 10:10:1 (v/v) as assay conditions. To the mixture was added methanol and the solution was stirred for 1 hour. All of the solvents were evaporated and the residue was chromatographed on Bakerbond Octadecyl (40 $\mu$m) silica gel and eluted with water and 10% methanol in water. The combined fractions were subjected to sodium ion exchange resin for the exchange of residual ionic salts for sodium ions. Lyophilization provided persulfated 3,4-di-C-fucosyl sodium cafeate.

As an additional alternative method: To a solution of the alcohol(s) groups to be sulfated from the products of the invention (1.00 mmole equiv.) in anhydrous pyridine or diemthylformamide (0.2M) at ambient temperature was added sulfur trioxide pyridine complex of the sulfur trioxide pyridine complex polymer bound [Graf, W. chem. Ind. 1987, 232.] (10 mmole equiv.). The reaction contents were stirred at ambient temperature for 8 hours. The reaction was quenched using sodium carbonate and removing the solvents by lyophilization and the resulting material was subjected to sodium ion exchange resin for the exchange of residual ionic salts for sodium ions. Concentration in vacuo affords the sulfated materials.

The experimental procedures described can be applied to make and modify the following exemplified novel products.

General references on applicable transformations can be found, among other places, in:

R. C. Larock, Comprehensive Organic Transformations, ISBN 0-89573-710-8, 1989, VCH Publishers, Inc. 220 East 23rd Street, Suite 909, New York, N.Y. 10010.

G. A. Olah, et al, Synthesis, 59, (1979), G. A. Olah, et al, Synthesis, 984, (1979), Y. Hamada, T. Shiori, Chem. Pharm. Bull. 30, 1921, (1982).

Ketone Formation

Oxidation of the alkene to the ketone via catalytic oxidation with osmium tetroxide sodium periodate. To a stirred solution of the olefin, (1.00 mmole equiv.) in 1% water in acetone (0.5M) at 0° C. is added osmium tetroxide predissolved in acetone (0.01 mmole equiv.) and sodium periodate (2.00 mmole equiv.) is carefully added as a solid. The reaction contents are stirred at 0° C. and the cooling bath (water/ice) is allowed to melt and the reaction allowed to stir at ambient temperature for 18 hours or until the reaction is complete via analysis by TLC. The reaction can be assayed by TLC or an aliquot of the reaction contents is removed, quenched into aqueous sodium metasulfite and extracted with ethyl acetate. The aliquot is checked by $^1$H-NMR. The reaction is terminated by the careful addition of sodium bisulfite (contains a mixture of $NaHSO_3$ and $NA_2S_2O_5$), stirred for 1 hour at room temperature and then water. An extraction solvent such as chloroform is added and the hydrochloric acid, water and brine. The washed product is dried over anhydrous sodium sulfate and filtered. The product can be purified by column chromatography using Baker grade flash silica gel (47–61 mm) and a suitable solvent system. For example, 10% ethyl acetate in hexanes and then with 30% ethyl acetate in hexanes. The silica gel is eluted with methanol and checked by TLC for any product material. The solvents are removed in vacuo and the product dried under vacuum. The desired product is recovered.

General references on applicable transformations can be found, among other places, in:

M. Hudlicky, Oxidations in Organic Chemistry, ACS Monograph #186, c1990, ISBN 0-8412-1781-5, Published by The American Chemical Society, Washington, D.C.

R. Pappo, D. S. Allen Jr., R. U. Lemieux, W. S. Johnson, J. Org. Chem., 21, 478, (1956).

R. C. Larock, Comprehensive Organic Transformations, ISBN 0-89573-710-8, 1989, VCH Publishers, Inc. 220 East 23rd Street, Suite 909, New York, N.Y. 10010.

Jerry March, Advanced Organic Chemistry, 3rd Edition, c1985, ISBN 0-471-88841-9, John Wiley & Sons Publishers, New York USA.

H. O. House, Modern Synthetic Reactions, c1972, ISBN 0-8053-4501-9, The Benjamin/Cummings Publishing Company, Menlo Park, Calif., USA.

F. A. Carey and R. J. Sundberg, Advanced Organic Chemistry Parts A & B, 2nd Edition, c1983, ISBN 0-306-41199-7, Plenum Press, a division of Plenum Publishing Corporation, 233 Spring Street, New York, N.Y. 10013, USA.

Wittig (Ester)

The use of a Wittig reagent for the conversion of a ketone to an alpha, beta unsaturated ester can be found in the additional references:

R. C. Larock, Comprehensive Organic Transformations, ISBN 0-89573-710-8, 1989, VCH Publishers, Inc., 220 East 23rd Street, Suite 909, New York, N.Y. 10010

Jerry March, Advanced Organic Chemistry, 3rd Edition, c1985, ISBN 0-471-88841-9, John Wiley & Sons Publishers, New York, USA.

H. O. House, Modern Synthetic Reactions, c1972, ISBN 0-8053-4501-9, The Benjamin/Cummings Publishing Company, Menlo Park, Calif., USA.

F. A. Carey and R. J. Sundberg, Advanced Organic Chemistry Parts A & B, 2nd Edition, c1983, ISBN 0-306-41199-7, Plenum Press, a division of Plenum Publishing Corporation, 233 Spring Street, New York, N.Y. 10013, USA.

Wittig (Alkene)

The use of a radiolabelled Wittig reagent for the conversion of a ketone to an alkene can be found in Bioorg. Chem. 19, 327, (1991) or J. Amer. Chem Soc. 111, 3740, (1989). Additional references can be found on applicable transformations in:

R. C. Larock, Comprehensive Organic Transformations, ISBN 0-89573-710-8, 1989, VCH Publishers, Inc., 220 East 23rd Street, Suite 909, New York, N.Y. 10010.

Jerry March, Advanced Organic Chemistry, 3rd Edition, c1985, ISBN 0-471-88841-9, John Wiley & Sons Publishers, New York, USA.

H. O. House, Modern Synthetic Reactions, c1972, ISBN 0-8053-4501-9, The Benjamin/Cummings Publishing Company, Menlo Park, Calif., USA.

F. A. Carey and R. J. Sundberg, Advanced Organic Chemistry Parts A & B, 2nd Edition, c1983, ISBN 0-306-41199-7, Plenum Press, a division of Plenum Publishing Corporation, 233 Spring Street, New York, N.Y. 10013, USA.

Sodium Borohydride Reduction

For a compound containing a ketone, (1.00 mmole equiv.) is dissolved in an appropriate solvent suitable for the compound to be reduced with sodium borohydride or equivalent. Solvents can include but not restricted to, tetrahydrofuran (THF), hexanes and diethyl ether, or combinations thereof. To a stirred solution of the ketone, (1.00 mmole equiv.) in THF (0.5M) at 0° C. is added sodium borohydride pre-dissolved/suspended in THF (1.00 mmole equiv.) is carefully added. The reaction contents are stirred at 0° C. and the cooling bath (water/ice) is allowed to melt and the reaction allowed to stir at ambient temperature for 8 hours or until the reaction is complete via analysis by tlc. The reaction is terminated by the careful addition of acetone and stirred for 1 hour at room temperature. Water is carefully added and the reaction contents stirred to decompose the alkyl borate. The contents are stirred until the alkyl borate decomposes to the carbonol. An extraction solvent such as chloroform or ethyl acetate is added and the heterogeneous layers are separated and the organic phase is washed with 1.0M hydrochloric acid, water and brine. The washed product is dried over anhydrous sodium sulfate and filtered. The product can be purified by column chromatography using Baker grade flash silica gel (47–61 mm) and a suitable solvent system. For example, 10% ethyl acetate in hexanes and then with 30% ethyl acetate in hexanes or appropriate solvent mixtures dependent upon the particular substrate used. The silica gel is eluted with methanol and checked by TLC for any product material. The solvents are removed in vacuo and the product dried under vacuum until the desired product is recovered.

General references on applicable transformations can be found, among other places, in:

R. C. Larock, Comprehensive Organic Transformations, ISBN 0-89573-710-8, 1989, VCH Publishers, Inc., 220 East 23rd Street, Suite 909, New York, N.Y. 10010.

Jerry March, Advanced Organic Chemistry, 3rd Edition, c1985, ISBN 0-471-88841-9, John Wiley & Sons Publishers, New York, USA.

H. O. House, Modern Synthetic Reactions, c1972, ISBN 0-8053-4501-9, The Benjamin/Cummings Publishing Company, Menlo Park, Calif., USA.

F. A. Carey and R. J. Sundberg, Advanced Organic Chemistry Parts A & B, 2nd Edition, c1983, ISBN 0-306-41199-7, Plenum Press, a division of Plenum Publishing Corporation, 233 Spring Street, New York, N.Y. 10013, USA.

EXAMPLE 1

Generation of Compounds: General Reaction

General Experimental Procedures:

One of ordinary skill in the art will appreciate and understand the following general experimentals as they are used in the art to prepare novel compounds from the invention. The mmole equivalents refers to the reaction substrate to be functionalized by the reaction with the carbon glycoside reagent per position to be alkylated. Additional functional group transformations can be accomplished by the skilled artisan using standard reaction conditions. For example, the transformation of allylic halides into allylic amines can be via the allylic azide with reduction of the azide to the amine with triphenylphosphine in water. The amine is then available for amide bond formation.

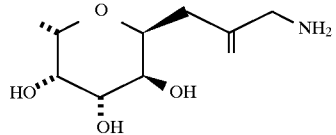

Alkylation conditions using Sodium hydride and an Aliphatic Alcohol. To a mechanically stirred solution of sodium hydride (3.00 mmole equiv. Note: the sodium hydride is washed three times with hexanes prior to use.) in THF (slurry) at ambient temperature is added an aliphatic alcohol (1.00 mmole equiv.) dropwise in a minimum of anhydrous tetrahydrofuran. Tetrabutylammonium iodide (0.10 mmole equiv.) is added and the reaction contents are stirred at room temperature (slight warming to above room temperature is sometimes needed for the initiation of the reaction) for 60 minutes in order to minimize the rate of gas evolution. The reaction contents are warmed for a period of 2 hours; carefully watching for the evolution of hydrogen. The reaction contents are stirred using a mechanical stirrer while being gently refluxed for a period of 1.5 hours. A benzyl protected carbon glycoside reagent to be used (1.50 mmole equiv.) is slowly added dropwise in anhydrous tetrahydrofuran (total reaction concentration of 0.2 to 0.5M) over a period of 1–2 hours and stirred for 4 hours. [An aliquot of the reaction contents is removed and quenched into 1.0M HCl and extracted with ethyl acetate; the TLC conditions used are 5% methanol in chloroform (v/v.] The reaction is then diluted with tolune and terminated by the careful addition of 50% methanol in toluene at 0° C. to consume the residual sodium hydride, followed by acidification of 1.0M hydrochloric acid until the pH is about 2. The reaction contents are diluted with ethyl acetate. The heterogeneous layers are separated and the organic phase is washed twice with portions of 1.0M hydrochloric acid, saturated sodium thiosulfate and brine. The product can be purified by column chromatography using Baker grade flash silica gel (47–61 mm) and a suitable solvent system. For example, 10% ethyl acetate in hexanes and then with 30% ethyl acetate in hexanes. The silica gel is eluted with methanol and checked by TLC for any product material. The solvents are removed in vacuo and the product dried under vacuum. The desired product is recovered.

General alkylation conditions using Cesium Carbonate as a mild base for the alkylation of thiols, amines, carboxylic acids and the like. To a stirred solution of thiols, phenols, amines, carboxylic acids and the like (1.00 mmole equiv.) in DMF or acetone (0.5M) is added cesium carbonate (3.00 mmole equiv.) and the Carbon-glycoside reagent (1.50 mmole equiv.). The reaction is stirred at room temperature for 12 hours. The reaction is assayed by TLC. The TLC conditions are usually 30% ethyl acetate in hexanes (v/v). The reaction contents are diluted with ethyl acetate and then poured into cold water. The organic layer is washed twice with water and then brine. The product is dried over anhydrous sodium sulfate and filtered to remove the drying agent. The solvent is removed in vacuo. The product can be purified by column chromatography using Baker grade flash silica gel (47–61 mm) and a suitable solvent system. For example, 10% ethyl acetate in hexanes and then with 30% ethyl acetate in hexanes. The silical gel is eluted with methanol and checked by TLC for any product material. The solvents are removed in vacuo and the product dried under vacuum. The desired product is recovered.

Removal of the acetyl protecting groups from the acetylated carbon glycosides. To a solution of the acetyl protected compounds (1.00 mmole equiv.) in methanol (0.5M) is added cesium carbonate or sodium methoxide (5.00 mmole equiv.) and water (catalytic) and the contents stirred for 48 hours. The reaction is quenched with 1.0M HCl until the pH is approximately 1. The product is extracted with an appropriate extraction solvent such as chloroform and the organic layer is washed with water. The product is dried over anhydrous sodium sulfate and filtered to remove the drying agent. The product can be purified by column chromatography using Baker grade flash silica gel (47–61 mm) and a suitable solvent system. For example, 10% ethyl acetate in hexanes and then with 30% ethyl acetate in hexanes. The silica gel is eluted with methanol and checked by TLC for any product material. The solvents are removed in vacuo and the product dried under vacuum. The desired product is recovered.

EXAMPLE 2
Preparation of 1-Deoxy-1-α-Iodoethyl-2,3,4-Tri-O-Acetyl-L-Fucose (2)

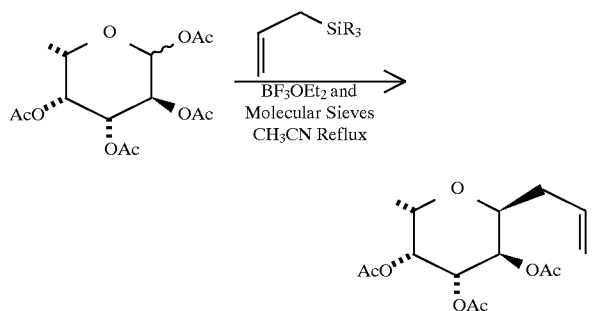

A solution of tetraacetylated L-fucose (9.0 g, 27.1 mmole) in acetonitrile (100 mmole) was stirred with one teaspoon of powdered molecular sieves (4 Å) for 30 minutes. This was mixed with allyltrimethylsilane (17.6 ml) followed by boron-trifluoride etherate (17.6 ml) solution in one portion. This reaction mixture was stirred at room temperature for three days. Most of volatiles were removed in vacuo and diluted with a 1:1 mixture of saturated sodium bicarbonate and brine solutions (100 ml). This was extracted with ethyl acetate (2×200 ml) and the combined organic extracts were washed with saturated sodium bicarbonate and brine solutions, dried over sodium sulfate, filtered and concentrated. The crude product was purified on a silica gel column (hexane: ethyl acetate, 3:1) to provide allylfucose 7.97$_9$, 94%).

A solution of allylfucose (5.1 g, 16.3 mmole) in a mixture of dichloromethane (80 ml) and methanol (20 ml) at −78° C. was bubbled with ozone until the blue color persisted. Excess ozone was removed by passing oxygen through the solution. This was mixed with dimethylsulfide (10 ml) and stirred at −78° C. to room temperature overnight. All the volatiles were removed in vacuo and dissolved in methanol (50 ml). At −78° C., this was mixed with sodium borohydride (620 mg) and warmed up to 0° C. and stirred for one hour. This is poured into water (50 ml) and extracted with ethyl acetate (2×100 ml). The organic extracts were washed with brine, dried over sodium sulfate, filtered and concentrated. The crude product was purified on a silica gel column (hexane: ethyl acetate, 1:1) to provide the alcohol (1.95 g, 38% yield). A much higher yield (90%) of the alcohol is obtained if sodium triacetoxyborohydride is used instead of sodium borohydride.

A solution of the above alcohol in pyridine (10 ml) and p-toluenesulfonylchloride (1.75 g) was stirred at 0° C. for 14 hours. This mixture was quenched with water (20 ml) and stirred for 20 minutes. This mixture was acidified with 6N of hydrochloride solution and extracted with ethyl acetate (2×100 ml). The combined organic extracts were then washed with water (100 ml), saturated sodium bicarbonate (30 ml), brine (30 ml), dried over sodium sulfate, filtered and concentrated to provide the crude tosylate. This crude product was heated with sodium iodide (3 g) in acetone (40 ml) at 450° C. for 2 hours. After cooling, the mixture was evaporated and the residue worked up with water (50 ml) and ethyl acetate (200 ml). The crude mixture was purified on a silica gel column (hexane ethyl acetate, 2:1) to provide the iodide 2 (2.9 g, 76%).

EXAMPLE 3
Synthesis of "Activated" Carbon Glycoside Building Blocks

A preferred method for the synthesis of terminally substituted halogen carbon glycosides comprises a chemical reaction of 2-chloromethyl-3-trimethylsilyl-1-propene (SAF Bulk Chemicals), or 2-chloromethyl-3-trimethoxysilyl-1-propene (SAF Bulk Chemicals), or 2-chloromethyl-3-trimethoxysilyl-1-propene by Gelest Inc. (U.S. Pat. No. 3,696,138), with an activated carbohydrate and a Lewis acid, whereby the allylsilanes undergo addition to the pyranose oxonium ions produced by Lewis acid catalysis for example with anomeric acetates. Nashed and Anderson, 1982, *Amer, Chem. Soc.* 104:7282; Panek and Sparks, 1989, *J. Org. Chem,* 54:2034. Other electrophilic sugars can be employed as stated earlier (Postema, 1995, supra). It will be apparent to those of ordinary skill in the art, that also other functional groups at the C-1 position can be used to convert the anomeric hydroxyl functionality into an appropriate leaving group at the C-1 position which can be used to convert the anomeric hydroxyl functionality into an appropriate leaving group to form the oxonium ion. 2-chloromethyl-3-trimethylsilyl-1-propene and 2-chloromethyl-3-trimethoxysilyl-1-propene exhibit about the same efficiency on the benzyl protected carbohydrates, while at least under the specific reaction conditions employed the per-O-acetylated carbohydrates used the 2-chloromethyl-3-trimethylsilyl-1-propene reagent.

The Carbon glycoside Formation with Benzyl Protected Sugar.

2-Chloromethyl-3-(tri-O-benzylα-L-C-fucopyranoside)-1-propene (3)

To a stirred solution of 500 g of 2,3,4-tri-O-benzyl-L-fucopyranose (1.15 mole) (Pfanstiehl, Inc.) in 500 ml 1,2-dichloroethane or 550 ml THF, 240 ml acetic anhydride, 135 ml pyridine was added, and the mixture stirred at room temperature for 22 hours. Subsequently, the reaction was diluted with ethyl acetate, washed with water, saturated with sodium bicarbonate and again with water. The solvents were moved in vacuo and azeotroped with toluene. The white solid was placed on a vacuum line, which afforded 542 g (99%) of 1-O-Acetyl-2,3,4-tri-O-benzyl-L-fucopyranose as a colorless crystalline solid in a mixture of anomeric acetates, mp=86°–87.5° C. 564.35 g 1-O-Acetyl-2,3,4-tri-O-benzyl-L-fucopyranose (1.19 moles, 1.00 eq.) and 214.6 ml 2-chloromethyl-3-trimethylsilyl-1-propene (1.19 mole, 1.00 eq.) were dissolved in 1.2 l acetonitrile (HPLC grade) and cooled to approximately 0° C. using an ice-water bath. Subsequently, 11.46 ml trimethylsilyltrifluoromethane sulfonate (59.28 mmoles, 0.05 eq.) was carefully added, the ice-water bath was allowed to melt and the reaction slowly warmed to room temperature (18 hours). Completion of the transformation from starting material to product was indicated by TLC. The reaction was terminated by pouring the reaction contents onto 1 l of ice-water, followed by adjustment to room temperature. The resulting mixture was extracted with 1 l ethyl acetate and the organic phase then washed with 1.0N aqueous sodium hydroxide and brine. The organic phase was dried over anhdyrous magnesium sulfate, filtered, and the solvent was removed in vacuo, which afforded 600.5 g of 2-Chloromethyl-3-(tri-O-benzyl-α-L—C-fucopyranoside)-1-propene (1) as light yellow solid. The product was purified either by crystallization in methanol at 0° C., or by column chromatography using Baker grade flash silica gel (47–61 mm) (ratio of 20 to 1), followed by elution with 5 to 10% ethyl acetate in hexanes giving a white solid (98%), mp 47°–49° C. In low scale reactions, the α- to β-ratios of the C-glycosidation reaction, was >10:1 in favor of the α-fucose derivative (Cha, et al., 1982, J. Am. Chem. Soc. 104:4976). The higher the reaction scale, the less β isomer could be observed; at scales in the multi-gram levels, sometimes only trace amounts.

The results of this study are complementary to related C-glycoside formation reactions for pyranosides using an allylic silane and an activated glycal. In another preferred embodiement, the Finkelstein exchange of the chloride for iodide (97% yield) or bromide (95% yield) was performed under standard conditions such as NaI in refluxing acetone or LiBr in refluxing THF. The course of the reaction was monitored by TLC or NMR techniques. Under certain conditions, bromide appears to be more stable than the corresponding iodide and seems to result in higher yielding alkylations.

This preferred method of forming C-glycosides with the benzyl protected sugar, 1-O-acetyl-2,3,4-tri-O-benzyl-L-fucopyranoside is reflected in the following scheme:

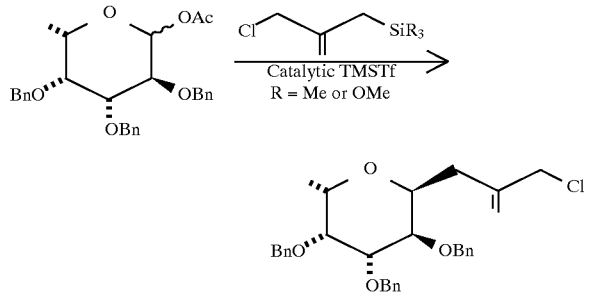

The following are typical scales of this reaction: Starting material Acetate/2-chloromethyl-3-trimethylsilyl-1-propene (310 g/118 ml), Product obtained (331 g); Acetate/2-chloromethyl-3-trimethylsilyl-1-propene(380 g/144 ml), Product obtained (400 g).

An alternate procedure starting from the anomeric hydroxyl can be done as follows: To a solution of 20 g tri-O-benzyl-L-fucopyranose (46.03 mmole, 1.00 mmole equiv.) in 200 ml anhydrous acetonitrile 30.0 g 2-chloromethyl-3-trimethylsilyl-1-propene (184.34 mmole, 4.00 mmole equiv.) at 0° C. 10.24 g trimethylsilane trifluoromethane sulfonic acid (46.03 mmol, 1.00 mmole equiv.) was added dropwise in 30 ml anhydrous acetonitrile (overall reaction concentration 0.2M) and the reaction contents stirred at 0° C. for 30 minutes. After 30 minutes, the reaction was diluted with 230 ml ethyl acetate and terminated by pouring the contents slowly into saturated sodium bicarbonate. The heterogenous layers were separated and the organic phase was washed twice with portions of water, 1.0M hydrochloric acid and brine. The crude product was dried over anhydrous sodium sulfate, filtered and plugged through a small pad of silica gel. The solvent was removed in vacuo which afforded an oil that was chromatographed on Baker grade flash silica gel (47–61 mm; ratio of 50 to 1) and eluted with 5 to 10% ethyl acetate in hexanes. Concentration in vacuo afforded 20.01 g of 2-chloromethyl-3-(tri-O-benzyl-α-L-C-fucopyranoside)-1-propene (85%). MW=507, [α]D: −27.37, C=0.95 in CHCl$_3$. A second product, α-L-2,3,4-tri-O-benzyl-fucopyranose-α-L-2,3,4-tri-O-benzyl-fucopyranose.

The product gave the following analytical data:
Reaction yield: 91%, mp=47°–49° C. $^1$H-NMR (CDCl$_3$) δ 7.20–7.50 (m, 15H, aromatics), 5.2 (d, J=47.9 Hz, 2H, terminal vinyl), 4.50–4.90 (complex multiplet, 6H, benzylic), 4.25 (p, 1H, H-1), 4.10 (s, 2H, —CH$_2$Cl), 3.90 (m, 1H), 3.75 (s, 1H), 2.50 (m, 2H), 1.25 (d, 3H). $^{13}$C-NMR (CDCl$_3$) δ 142.68 alkene (e), 138.62 aromatic (e), 138.29 aromatic (e), 138.11 aromatic (e), 128.17 aromatic (o), 127.86 aromatic (o), 127.45 aromatic (o), 127.34 aromatic (o), 116.28 alkene (e), 76.58 (o), 75.95 (o), 73.24 (e), 72.97 (e), 68.33 (o), 48.23 —CH$_2$Cl (e), 30.30 allylic (e), 15.38 fucose methyl (o). Mass Spec. (LSIMS with mNBA) 505.1/507.3. Analytical Calculated for CH$_{31}$H$_{35}$ClO$_4$: C, 73.43; H, 6.96. Found: C, 73.16; H. 7.12.

EXAMPLE 4
2-Chloromethyl-3-(tetra-O-benzyl-α-L-C-glucopyranocide) 1-propene (4)

In another preferred embodiment, 1-O-acetyl-2,3,4,6-tetra-O-benzyl-D-glucopyranose was subjected to the same reaction conditions as have been described for L-fucopyranoside, resulting in the α-C-glycosides of glucose (91% mp=79°–81° C.), as reflected below:

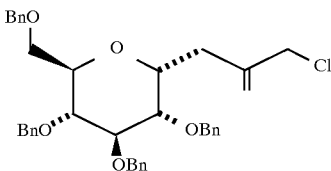

In general, the reagent ratios for the remaining per-O-acetylated carbohydrates were for example: 1,2,3,4,6-penta-O-acetyl-D-galactopyranoside (1.00 mmole equiv.) and 2-chloromethyl-3-trimethylsilyl-1-propene (2.00 mmole equiv.) were dissolved in acetonitrile (1.3M). Boron trifluoride etherate (2.00 mmole equiv.) and trimethylsilyltrifluoromethane sulfonate (0.40 mmole equiv.) were carefully added neat at room temperature. The reaction was refluxed for 6 hours and worked up as described. TLC 30% ethyl acetate in hexanes.

The glucose product (4) gave the following analytical data:
Reaction yield: 91%, mp=79°–81° C. $^1$H-NMR (CDCl$_3$) δ 7.10–7.40 (20H), 5.1 (d, J=41.3 Hz, 2H, terminal vinyl), 4.96 (d, 10.87 Hz, 1H), 4.82 (d, 10.87 Hz, 1H), 4.82, (d, J=10.56 Hz, 1H), 4.63 (d, J=12.15 Hz, 1H), 4.44 (d, J=12.15 Hz, 1H), 4.45 (d, J=1.56 Hz, 1H), 4.67 (q, J=11.6 Hz, 2H), 4.24 (p, J=5.07 Hz, 1H, H-1), 4.12 (s, 2H), 3.68 (m, 6H, ring), 2.65 (m, 2H). $^{13}$C-NMR (CDCl$_3$) δ 142.32 alkene (e), 138.68 (e), 138.08 (e), 137.93 (e), 128.5 (o), 128.0 (o), 127.8 (o), 127.5 (o), 116.95 alkene (e), 82.31 ring (o), 79.85 ring (o), 77.91 ring (o), 75.56 (e), 75.16 (e), 73.46 (e), 73.19 (e), 72.80 ring (o), 71.31 ring (o), 68.79CH$_2$ ring (e), 48.15 CH$_2$Cl allylic (e), 27.98 allylic (e). Mass Spec. (LSIMS with mNBA and NaOAc) 635.2 (MNa$^+$). Analytical Calculated for C$_{38}$H$_{41}$ClO$_5$: C, 74.43; H, 6.74. Found: C, 74.62; H, 6.92.

EXAMPLE 5
2-Chloromethyl-3-(2,3,4,6-tetra-O-benzyl-D-galactopyranoside)-1-propane (5)

In another preferred embodiment, 1-O-acetyl-2,3,4,6-tetra-O-benzyl-D-galactopyranose were subjected to the same reaction conditions as have been described for L-fucopyranoside, resulting in the α-C-glycosides of galactose (5) (84%, oil), as reflected below:

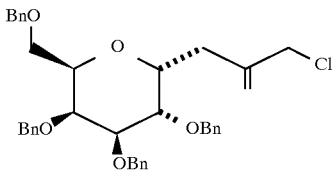

The product gave the following analytical data:
Reaction yield: 84%, and the compound isolated as an oil. $^1$H-NMR (CDCl$_3$) δ, 7.25 (m. 20H), 5.16 (d, J=37.54 Hz, 2H), 4.85–4.50 (overlapping benzylic patterns, 6H), 4.26 (p, 3.85 Hz, 1H, H-1), 4.16 (s, 2H), 4.09 (m, 2H), 3.88 (m, 2H), 3.79 (dd, J=4.88 Hz, 1H), 2.59 (m, 2H). $^{13}$C-NMR (CDCl$_3$) δ 143.32 alkene (e), 139.21 (e), 139.09 (e), 138.90 (e), 138.83 (e), 128.5 (o), 128.0 (o), 127.8 (o), 127.5 (o), 117.22 alkene (e), 77.32 ring (o), 74.89 ring (o), 74.00 (e), 73.88 (e), 73.83 (e), 73.69 (e), 72.72 (o), 68.19 (e), 49.09 (e), 28.98 allylic (e). Mass Spec. (LSIMS with mNBA and NaOAc) 635.3 (MNa$^+$). Analytical Calculated for C$_{38}$H$_{41}$ClO$_5$: C, 74.43; H, 6.74. Found: C, 74.31; H, 6.87.

EXAMPLE 6
2-Iodomethyl-3-(2,3,4,-tri-O-benzyl-α-L—C-fucopyranoside)-1-propene (6)

331 grams of 2-chloromethyl-3-(tri-O-benzyl-α-L-C-fucopyranoside)-1-propene (653 mmole, 1 mmole equiv.) was added to a stirred suspension of 480 g NaI (3222 mmole, 5 mmole equiv.) in 3 l acetone; the reaction was heated to reflux for 3 hours and then allowed to cool to room temperature. Completion of the reaction was monitored by TLC assay. The TLC conditions used were 10% ethyl acetate in hexanes (v/v). The reaction was complete when the product Rf was slightly higher than starting material. The reaction contents were poured into cold water and extracted with EtOAc. The organic layer was washed twice with saturated cold sodium thiosulfate, saturated NaHCO$_3$, and with water. The product was dried over anhydrous sodium sulfate and filtered to remove the drying agent. The solvent was removed in vacuo which afforded a light yellow waxy solid. Then, the product was dissolved in THF and then concentrated in vacuo twice at low temperatures to remove any residual solvents not desired for the next step to afford 380 grams of 2-Iodomethyl-3-(tri-O-benzyl-α-L-C-fucopyranoside)-1-propene (6) (97%). This material should be protected from heat and light, and used immediatly. A typical scale for this reaction is: 331 g starting material, resulting in a yield of 380 g Product.

The product is depicted below:

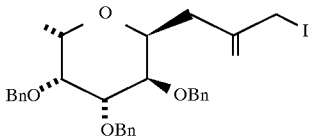

EXAMPLE 7
2,3,4-Tri-O-benzyl-α-L-C-Fucopyranoside allylbromide reagent (7)

To a stirred suspension of 42.72 g LiBr (493 mmole, 5 mmole equiv.) in 197 ml THF 50.0 g 2-chloromethyl-3-(tri-O-benzyl-α-L-C-fucopyranoside)-1-propene (98.6 mmole, 1 mmole equiv.) was added and the reaction was heated to reflux for 3 hours, and then allowed to cool to room temperature. The reaction was complete as assayed by TLC (product Rf slightly higher than starting material). The TLC conditions used were 10% ethyl acetate in hexanes (v/v). The reaction contents were concentrated to half of the original volume of THF, poured into cold water and then extracted with EtOAc. The organic layer was washed twice with water, 1.0M HCl and again with water. The product was dried over anhydrous sodium sulfate and filtered to remove the drying agent. The solvent was removed in vacuo which afforded a light yellow solid. The product was dissolved in methanol and then concentrated in vacuo at low temperatures twice to remove any residual solvents. The product was dissolved in 150 ml warm methanol and cooled to 0° C. overnight. Filtration of the solids results in 40.8 grams as a white crystalline solid. Concentration of the mother liquors to half of the original volume and again cooling to 0° C. overnight gave an additional 10.87 grams of a white crystalline solid. Combined recovery yielded 51.67 g of 2-bromomethyl-3-(2,3,4-tri-O-benzyl-α-L-C-fucopyranoside)-1-propene; mp=51.5°–53° C., (95%).

The product gave the following analytical data:
$^1$H-NMR (CDCl$_3$) δ 7.20–7.50 (m, 15H, aromatics), 5.2 (d, J=61.5 Hz, 2H, terminal vinyl), 4.50–4.90 (complex multiplet, 6H, benzylic, 4.25 (p, J=4.22 Hz, 1H, H-1), 4.04 (d, J=3.1 Hz, 2H, —CH$_2$Br), 3.90 (m, 1H), 3.75 (s, 1H), 2.50 (m, 2H), 1.25 (d, 3H). $^{13}$C-NMR (CDCl$_3$) δ 1423.11 alkene (e), 138.77 aromatic (e), 138.53 aromatic (e), 138.26 aromatic (e), 128.17 aromatic (e), 127.86 aromatic (o), 127.45 aromatic (o), 127.34 aromatic (o), 117.00 alkene (e), 76.69 (o), 76.16 (o), 73.46 (e), 73.11 (e), 69.9 (o), 68.46 (o), 37.03 —CH$_2$Br (e), 30.54 allylic (e), 15.61 fucose methyl (o). Analytical Calculated for C$_{31}$H$_{35}$BrO$_4$: C, 67.51; H, 6.40. Found: C, 67.81; H, 6.56.

In general, the reagent ratios for the remaining per-O-acetylated carbohydrates were for example: 1,2,3,4,6-penta-O-acetyl-D-galactopyranoside (1.00 mmole equiv.) and 2-chloromethyl-3-trimethylsilyl-1-propene (2.00 mmole equiv.) were dissolved in acetonitrile (1.3M). Boron trifluoride etherate (2.00 mmole equiv.) and trimethylsilyltrifluoromethane sulfonate (0.400 mmole equiv.) were carefully added neat at room temperature. The reaction was refluxed for 6 hours and worked up as described. TLC 30% ethyl acetate in hexane.

EXAMPLE 8
The Carbon Glycoside Formation with Acetyl Protected Sugar

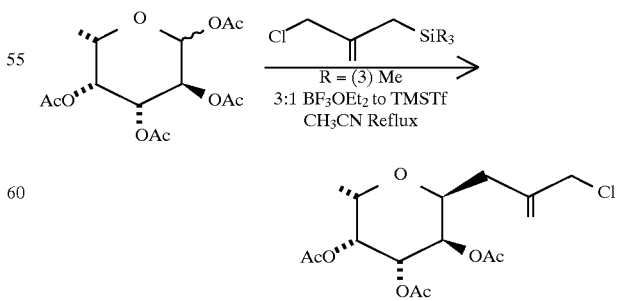

2-Chloromethyl-3-(tri-O-acetyl-α-L-C-fucopyranoside)-1-propene (8)

50.0 g 1,2,3,4-tetra-O-acetyl-L-fucopyranose (5) (150.5 mmole, 1.00 mmole equiv.) and 36.7 g (40.9 ml) 2-chloromethyl-3-trimethylsilyl-1-propene (225.7 mmole, 2.00 mmole equiv.) were dissolved in 116 ml acetonitrile; subsequently, 74.8 g boron trifluoride etherate (526.8 mmole, 3.50 mmole equiv.) and 13.4 g (11.6 ml) trimethylsilyltrifluoromethanesulfonate (60.2 mmoles, 0.40 mmole equiv.) were carefully added after the addition of the Lewis acids (preferentially trimethyltrifluoromethanesulfonate and boron trifluoride etherate), the reaction was slowly warmed to reflux and maintained at reflux for 6 hours. The reaction was terminated by cooling to room temperature, pouring the reaction contents on 100 ml of water, followed by extraction of the crude α-C-glycoside with ethyl acetate. The heterogenous layers were separated and the organic phase was washed with portions of water, saturated sodium bicarbonate, 1.0M hydrochloric acid and brine. The crude extract was dried over anhydrous sodium sulfate, filtered, and the solvent was removed in vacuo to afford an oil that was purified by column chromatography on Baker grade flash silica gel (47–61 mm) (ratio of 20 to 1), eluted with 10% ethyl acetate in hexanes. Concentration in vacuo afforded 46.4 g of 2-chloromethyl-3-(2,3,4-tri-O-acetyl-α-L-C-fucopyranoside)-1-propene (85%, oil).

Under these reaction conditions, the 1,2,3,4-tetra-O-acetyl-L-fucopyranoside reaction mixture turned a dark brown to black color, and TLC monitoring showed the transformation from starting material to the (α-C-glycoside proceeded as expected. Two compounds, distinguishable by TLC, were isolated by column chromatography on silica gel by elution with 10% ethyl acetate in hexane. As determined by NMR analysis, the major compound was the 2,3,4-tri-O-acetyl-α-C-L-fucopyranoside (85%), and a minor compound was a small amount of starting material. The baseline material observed by TLC probably representing a third unidentified molecule.

The product gave the following analytical data:

Reaction yield: 85%, and the compound isolated as an oil. $^1$H-NMR (CDCl$_3$) δ, 5.3 (m, 1H), 5.2 (m, 2H), 5.2(s, 1H), 5.05 (s, 1H), 4.38 (m, J=3.48 Hz, 1H, H-1), 4.09 (s, 2H), 3.95 (dq, J=1.71 Hz and 4.70 Hz, 1H), 2.6 (dd, J=11.39 Hz, 1H), 2.4 (dd, J=3.42 Hz, 1H), 2.15 (s, 3H), 2.05 (s, 3H), 1.98 (s, 3H), 1.09 (d, J=6.41 Hz, 3H). $^{13}$C-NMR (CDCl$_3$) δ 171.03 acetyl (e), 170.66 acetyl (e), 170.38 acetyl (e), 142.06 alkene (e), 117.72 alkene (e), 71.66 ring (o), 71.19 ring (o), 68.94 ring (o), 68.40 ring (o), 66.33 ring (o), 48.51 allylic (chloride side) (e), 29.50 allylic (e), 20.77 (o), 20.71 (o), 20.64 (o), 16.53 L-fucose methyl group (o). IR 2985, 1746, 1646 cm$^{-1}$. Mass Spec. (LSIMS with mNBA and NaOAc) 385.1 (MNa$^+$), 363.2 (MH$^+$). Analytical Calculated for C$_{16}$H$_{23}$ClO$_7$: C, 52.97; H, 6.39. Found: C, 52.66; H, 6.40.

EXAMPLE 9

Deprotection of Fucose:

The deprotection of the fucose reagent was done in methanol with a catalytic amount of sodium metal added to the stirring methanol. The reaction was terminated by the careful addition of 1.0M HCl until the pH was approximately 2. The solvent was removed in vacuo. The deprotected fucose is reflected in the following structure:

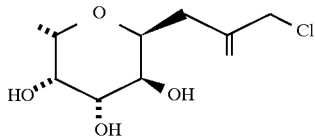

The product gave the following analytical data:

The reaction was quantitative, mp=185°–186.5° C. $^1$H-NMR (CDCl$_3$) δ, 5.02 (d, J=42.8, 2H, terminal vinyl), 4.01 allylic —CH$_2$Cl (s, 2H), 3.89 (p, J=3.91 Hz, 1H, H-1), 3.69 (m, 2H, H-2 & 5), 3.45 (m, 2H, H-3 & 4), 2.36 (m, 2H, allylic), 0.97 (d, J=6.47 Hz, 3H). $^{13}$C-NMR (CD$_3$OD) δ 145.35 alkene (e), 117.18 alkene (e), 75.35 ring (o), 72.84 ring (o), 72.34 ring (o), 69.88 ring (o), 69.15 (o), 49.34 —CH$_2$Cl (e), 29.50 allylic (e), 17.05 L-fucose methyl (o). Mass Spec. (LSIMS with Gly) 237.1 (MH$^+$). Analytical Calculated for C$_{10}$H$_{17}$ClO$_4$: C, 50.74; H, 7.24. Found C, 50.63; H, 7.43.

EXAMPLE 10

2-Chloromethyl-3-(tetra-O-acetyl-α-L-C-glucopyranoside) 1-propene (10)

The reaction conditions used for the α-C-glycosidation of 1,2,3,4-tetra-O-acetyl-L-fucopyranoside were applied to 1,2,3,4,6-penta-O-acetyl-D-glycopyranose, and yielding the expected α-C-glycosides of α-C-glucose (20%). NMR analysis of the α-C-glycoside carbon shifts (CDCl$_3$) for the added C-3 unit in the acetyl protected sugars showed a chemical shift around δ 48 for the —CH$_2$Cl allylic carbon and δ 28 for the allylic carbon which forms the C-glycoside at the C-1 carbohydrate position, and the alkene shifts were around δ 142 and δ 117. The carbon shifts for the allylic chloride side chain in the benzylated sugars and in the acetyl protected sugars were comparable. The α-carbon glycoside derivative of glucose is shown below:

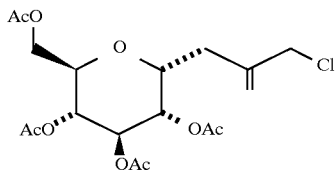

The product gave the following analytical data:

Reaction yield: 20%, and the compound isolated as an oil. $^1$H-NMR (CDCl$_3$) δ, 5.26 (t, J=9.10 Hz, 1H, H-3), 5.10 (d, J=45.12 Hz, 2H, terminal vinyl), 5.02 (m, 1H, H-3), 5.10 (d, J=45.12 Hz, 2H, terminal vinyl), 5.02 (m, 1H, H-2), 4.90 (t, J=8.97 Hz, 1H, H-4), 4.33 (m, 1H, H-1), 4.13 (dd, J=5.44 Hz, 1H, H-6), 3.98 (dd, J=2.62 Hz, 1H, H-6), 4.05 (s, 2H, —CH$_2$Cl), 3.86 (m, 1H, H-5), 2.61 (dd<J=11.54 Hz, 1H), 2.38 (dd, J=3.17 Hz, 1H), 1.99 (s, 3H, acetyl), 1.98 (s, 3H, acetyl), 1.96 (s, 3H, acetyl), 1.95 (s, 3H, acetyl). $^{13}$C-NMR (CDCl$_3$) δ 172.03 acetyl (e), 171.54 acetyl (e), 171.04 acetyl (e), 170.99 acetyl (e), 142.33 alkene (e), 118.96 alkene (e), 72.55 ring (o), 71.57 ring (o), 71.43 ring (o) 70.49 ring (o), 70.13 ring (o), 63.63 C-6 ring (e), 49.29 —CH$_2$Cl (e), 30.15 allylic (e), 22.11 acetyl groups (o), 22.06 acetyl groups. IR 2958, 1729, 1646 cm$^{-1}$.

EXAMPLE 11

2-Chloromethyl-3-(tetra-O-acetyl-α-L—C-galactopyranoside)-1-propene (11)

The reaction conditions used for the α-C-glycosidation of 1,2,3,4-tetra-O-acetyl-L-fucopyranoside were applied to the 1,2,3,4,6-penta-O-acetyl-D-galactopyranose yielding the expected α-C-glycosides of α-C-galactose (74%). 1,2,3,4,6-penta-O-Acetyl-D-galactopyranoside (1.00 mmole equiv.) and 2-chloromethyl-3-trimethylsilyl-1-propene (2.00 mmole equiv.) were dissolved in acetonitrile (1.3 m). Boron trifluoride etherate (2.00 mmole equiv.) and trimethylsilyl-trifluoromethane sulfonate (0.40 mmole equiv.) were carefully added neat at room temperature. The reaction was refluxed for 6 hours and worked up as described; TLC: 30% ethyl acetate in hexanes.

NMR analysis of the α-C-glycoside carbon shifts (CDCl$_3$) for the added C-3 unit in the acetyl protected sugars showed a chemical shift around δ 48 for the —CH$_2$Cl allylic carbon and δ 28 for the allylic carbon which forms the C-glycoside at the C-1 carbohydrate position, and the alkene shifts were around δ 142 and δ 117. The carbon shifts for the allylic chloride side chain in the benzylated sugars in the acetyl protected sugars were comparable. The α-carbon glycoside derivative of galactose is shown below:

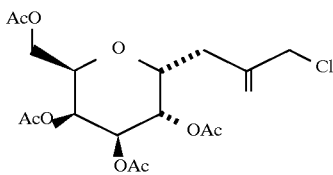

The product gave the following analytical data:

Reaction yield: 74%, mp=80°–82° C. $^1$H-NMR (CDCl$_3$) δ, 5.31 (br, 1H), 5.16 (m, 2H), 5.05 (d, J=47.17 Hz, 2H, terminal vinyl), 4.33 (m, J=3.54, 1H, H-1), 4.1–3.9 (m, 3H), 4.02 (s, 2H), 2.52 (dd, J=11.41, 1H), 2.28 (dd, J=2.75, 1H), 2.01 (s, 3H, acetyl), 1.98 (s, 3H, acetyl), 1.91 (s, 6H, acetyl). $^{13}$C-NMR (CDCl$_3$) δ 170.18 acetyl (e), 169.81 acetyl (e), 169.97 acetyl (e), 169.53 acetyl (e), 141.04 alkene (e), 117.17 alkene (e), 70.64 ring (o), 68.09 ring (o), 67.79 ring (o), 67.55 ring (o), 67.42 ring (o), 62.32 C-6 ring (e), 47.65 —CH2Cl (e), 28.86 allylic (e), 20.53 acetyl group (o), 20.47 acetyl group (o), 20.41 acetyl group (o). IR 2958, 1729, 1646 cm$^{-1}$. Mass Spec. (LSIMS with mNBA and NaOAc) 443.1 (MNa$^+$), 421.2 (MH$^+$). Analytical Calculated for C$_{18}$H$_{25}$ClO$_9$: C, 51.37; H, 5.99. Found: C, 51.47; H, 6.15.

EXAMPLE 12
2-Chloromethyl-3-(tetra-O-acetyl-α-L-C-mannoopyranoside)-1-propene (12)

The reaction conditions used for the α-C-glycosidation of 1,2,3,4-tetra-O-acetyl-L-fucopyranoside were applied to 1,2,3,4,6-penta-O-acetyl-D-mannopyranose yielding the expected α-C-glycoside of α-C-mannose (80%).

NMR analysis of the α-C-glycoside carbon shifts (CDCl$_3$) for the added C-3 unit in the acetyl protected sugars showed a chemical shift around δ 48 for the —CH$_2$Cl allylic carbon and δ 28 for the allylic carbon which forms the C-glycoside at the C-1 carbohydrate position, and the alkene shifts were around δ 142 and δ 117. The carbon shifts for the allylic chloride side chain in the benzylated sugars and in the acetyl protected sugars were comparable. The a-carbon glycoside derivated of mannose is shown in the following scheme:

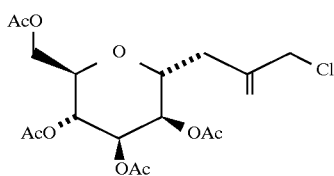

The product gave the following analytical data:

Reaction yield: 80%, (compound isolated as an oil). $^1$H-NMR (CDCl$_3$) δ 5.13 (m, 3H), 5.12 (d, J=41.76 Hz, 2H, terminal vinyl, 4.20 (q, J=6.41 Hz, 1H, H-1), 4.05 (m, 2H), 4.04 (d, J=1.65 Hz, 2H, 3.85 (m, J=269 Hz, 1H), 2.60 (dd, J=10.32 Hz, 1H), 2.39 (dd, J=4.52 Hz, 1H), 2.39 (dd, J=4.52 Hz, 1H), 2.03 (s, 3H, acetyl), 1.98 (s, 3H, acetyl), 1.93 (s, 3H, acetyl). $^{13}$C-NMR (CDCl$_3$) δ 1.70.28 acetyl (e), 169.89 acetyl (e), 169.66 acetyl (e), 169,37 acetyl (e), 140.43 alkene (e), 117.61 alkene (e), 73.06 ring (o), 70.52 ring (o), 70.07 ring (o), 68.47 ring (o), 66.52 ring (o), 62.04 Ch$_2$ (e), 47.47 —CH$_2$Cl (e), 31.95 allylic (e), 20.67 acetyl CH$_3$ (o), 20.50 acetyl CH$_3$ (o), 20.47 acetyl CH$_3$ (o), 20.43 acetyl CH$_3$ (o). IR 2958, 1729, 1646 cm$^{-1}$. Mass Spec. (LSIMS with mNBA and NaOAC) 443.0 (MNA$^+$), 421.3 (MH$^+$).

EXAMPLE 13
Preparation Of 1-Deoxy-1-α-(2-Carboxy-Naphthyl-6-Oxyethyl)-L-Fucose (13)

A solution of ethyl 6-hydroxyl-2-naphthate (49, 89 mg, 0.42 mmole) (6-hydroxy-2-naphthoic acid was obtained from TCI America and converted to the ester using standard esterification methods) and iodide (2, 177 mg, 0.42 mmole) in dimethylforamide (1 ml) was stirred with potassium carbonate (174 mg) for 14 hours. The reaction mixture was worked up with water (30 ml) and ethyl acetate (100 ml). The organic layer was washed with brine (30 ml), dried over sodium sulfate, filtered and concentrated. The crude product was purified on a silica gel column (hexane ethyl acetate, 4:1) to provide the triacetate of 3 (120 mg, 55%).

A solution of the triacetate in methanol (30 ml) was stirred with 1 Normal sodium hydroxide (3 ml) for 4 hours. The mixture was acidified with 6N hydrochloride and solid collected by filtration. This solid was washed with water, ethyl acetate and suction dried to provide naphthoic acid (13) (24 mg).

EXAMPLE 14
Preparation Of 3,7-Di-(1-Deoxy-1-α-Fucosyl-Ethyleneoxy)-2-Naphthoic Acid (14)

A solution of ethyl 3,7-dihydroxy-2-naphthoate (62 mg, 0.26 mmole) (the acid was obtained from Aldrich and it was converted to the ester using standard techniques) 2 mg, and iodide 2 (242 mg) in dimethylforamide (0.5 ml) was heated at 55° C. with potassium carbonate (175 mg) for 4 hours. An additional amount of the iodide 2 (80 mg) was added to the mixture which was heated at 55° C. overnight. The mixture was worked up with water (50 ml) and ethyl acetate (2×75 ml). The ethyl acetate extracts were washed with brine (30 ml), dried over sodium sulfate, filtered and concentrated. The crude product was purified on a silica gel column (hexane:ethyl acetate, 1.5:1) to provide the triacetate of 17 (130 mg, 65% yield).

A solution of the triacetate (120 mg) in methanol (1 ml) was stirred with 2N potassium hydroxide (1.1 ml) at room temperature overnight. This was acidified with 6N hydrochloride solution and concentrated to dryness. The residue was dissolved in methanol (10 ml) and solid removed by filtration. The filtrate was concentrated to provide naphthoic acid (14) (70 mg).

EXAMPLE 15
Preparation Of 3,5-Di-(1-Deoxy-1-α-Fucosyl-Ethyleneoxy)-2-Naphthoic Acid (15)

When ethyl 3,5-dihydtoxy-2-naphthoate (prepared by esterification of the corresponding acid) is substituted for ethyl 3,7-dihydroxy-2-naphthoate in Example 14, the identical process afforded the naphthoic acid (15).

EXAMPLE 16
Preparation Of 6-(1-Deoxy-1-α-Fucosyl-Ethyleneoxy)-α-Methyl-2-Naphthalene Acetic Acid (16)

6-Hydroxy-α-methyl-2-naphthaleneacetic acid methyl ester is prepared from 6-methoxy-α-methyl-2-naphthaleneacetic acid by first converting the methyl ether to a hydroxyl group utilizing refluxing 48% HBr/AcOH (Greene and Wuts) and then preparing the corresponding methyl ester utilizing diazomethane.

The iodide 2 (286.6 mg) and 6-hydroxy-α-methylnaphthaleneacetic acid methyl ester (154.0 mg) were dissolved in dimethylformamide (3 ml) and potassium carbonate (277,6 mg) was added. The reaction was stirred at room temperature for 12 hours, after which it was partitioned between water (10 ml) 15 and ethyl acetate (50 ml). The layers were separated and the organics were washed with water (3×10 ml) and brine (10 ml). The organic layer was dried over magnesium sulfate, filtered and concentrated to dryness. Purification of the residue on silica gel (25% ethyl acetate/hexane) gave the desired triacetate (225.8 mg, 64% yield).

The above triacetate product was dissolved in methanol (1.70 ml) and 2N sodium hydroxide solution (1.70 ml) was added. The reaction was stirred at room temperature for 13 hours, after which it was acidified with 6 N-hydrochloride. After concentrating to dryness, the residue was washed with water and dried under vacuum to give the desired product 19 (167 mg, 100% yield).

EXAMPLE 17
Preparation Of 6-Glyceroxy-α-Methyl-2-Naphthalene Acetic Acid (17)

6-Hydroxy-α-methyl-2-naphthaleneacetic acid methyl ester is prepared from 6-methoxy-α-methyl-2-naphthaleneacetic acid by first converting the methyl ether to a hydroxyl group utilizing refluxing 48% HBr/AcOH (Greene and Wuts) and then preparing the corresponding methyl ester utilizing diazomethane.

Glycidol (2.95 ml) (obtained from Aldrich) and 6-hydroxy-α-methylnaphthaleneacetic acid methyl ester (1.02 g) were dissolved in dimethylformamide (10 ml). Potassium carbonate (3. g) was added and the reaction was stirred at room temperature for 3 days. After diluting with ethyl acetate (100 ml), the reaction was washed with water (5×10 ml). The water layer was wahed with ethyl acetate (20 ml) and the combined ethyl acetate layers were washed with brine (20 ml). After concentrating, the residue was purified on silica gel (70% ethyl acetate/hexane) to give the desired methyl ester glycidol adduct (251.5 mg, 19% yield) and the glycidyl ester glycidol adduct (200.3 mg, 13% yield).

The glycidyl ester glycidol adduct was dissolved in methanol (0.6 ml) and 2N sodium hydroxide (0.6 ml) was added. The reaction was stirred at temperature for 23 hours and acidified with 6N hydrochloride. After concentrating the mixture to dryness, the residue was washed with water and dried under vacuum to give the desired product 17 (125.9 mg, 75% yield).

EXAMPLE 18
1-Deoxy-α-1-Acetylenyl-1,2,4-tri-O-Benzyl-1-Fucose (18)

A solution of 1-O-acetyl-2,3,4-tri-O-benzyl-L-fucose (10 g, 21 mmol) and bistrimethylsilylacetylene (7.16 g, 42 mmol) in dichloromethane (50 ml) was cooled to −20° C. under argon. A solution of tin tetrachloride in dichloromethane (21 mmol, 1M) was added and the mixture was stirred at −20° C. for 1 hour. The reaction was quenched with saturated aqueous sodium bicarbonate (50 ml), extracted with ethyl acetate (3×50 ml) and the combined organic layers were washed with saturated aqueous sodium bicarbonate (2×10 ml) and brine (20 ml), dried (MgSO$_4$), filtered and concentrated, the residue was purified on silica gel (30% ethyl acetate/hexane) to give the silylacetylenyl fucose (8.1 g, 75% yield). Water (10 ml) followed by potassium flouride (9.16 g, 158 mmol) was added to a solution of compound 70 (8.1 g, 15.76 mmol) in DMF (30 ml). The mixture was stirred at room temperature (2 h), diluted with water (100 ml) and extracted with 30% ethyl acetate/hexane (3×50 ml). The combined organic layers were washed with brine (50 ml), dried (MgSO$_4$), filtered and concentrated to give compound 18 (6.97 g, 100% yield).

EXAMPLE 19
Preparation of 1-Deoxy-1-α-(m-Carboxy-Phenylethyl)-L-Fucose-Phenylalanine Amide (19)

Carbonyl diimidazole (2.62 g, 16.14 mmol) was added to a solution of m-iodobenzoic acid (4 g, 16.14 mmol) in tetrahydrofuran (100 ml), the mixture was stirred at room temperature (45 min). Phenylalanine benzyl ester p-toluenesulfonate (6.90 g, 16.14 mmol) was added, the mixture was stirred (18), and concentrated to dryness. The organic phase was washed with 1N aq. HCL (3×20 ml), saturated aqueous sodium bicarbonate (2×20 ml) and brine (20 ml), dried (MgSO$_4$) and concentrated to give the amide (4.79 g, 61% yield).

The amide (1.28 g, 2.63 mmol) and compound 18 (1.16 g, 2.63 mmol) were dissolved in DMF (10 ml). Triethylamine (0.73 ml, 5.26 mmol) was added followed by tetrakistriphenyl-phosphine palladium (100 mg) and copper (1)iodide (40 mg). The reaction was stirred at room temperature (6 h), diluted with water (100 ml), and extracted with ethyl acetate (3×20 ml). The combined organic phases were washed with 1N aq. HCl (40 ml), saturated aqueous sodium bicarbonate (40 ml) and brine (40 ml), dried (MgSO$_4$)and concentrated. The residue was purified on silica gel (20% ethyl acetate/hexane) to give the coupled product (0.6 g, 28% yield).

The coupled product (0.6 g, 0.75 mmo) was dissolved in ethyl acetate (5 ml). 10% Palladium/carbon (0.6 g) was suspended in methanol (40 m) and the ethyl acetate solution was added via cannula. After stirring under hydrogen for 4 days, the mixture was filtered through Celite and the filtrate was concentrated to dryness giving the title compound 22 (0.24 g, 72% yield).

EXAMPLE 20

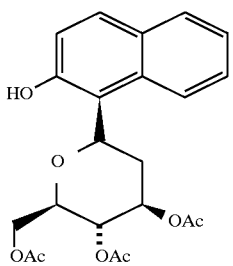

2-Naphthol (6.20 g, 43.01 mmole) and tetra-O-acetyl 2-deoxyglucose (14.28 g, 43.01 mole) were dissolved in acetonitrile (100 mL) and borontrifluoride etherate (10.58 mL) was added. The reaction was stirred at room temperature for 24 hours after which it was quenched with saturated aqueous sodium bicarbonate (100 mL). The resulting mixture was diluted with ethyl acetate (200 mL) and washed with saturated aqueous sodium bicarbonate (2×50 mL) and brine (50 mL). After drying over anhydrous magnesium sulfate, the solution was filtered, concentrated, and purified on silica gel (30% ethyl acetate/hexane) to give the desired product (10.54 g, 59%).

EXAMPLE 21

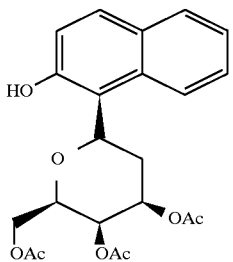

2-Naphthol (8.72 g, 60.48 mmole) and tetra-O-acetyl 2-deoxygalactose (20.08 g, 60.48 mmole) were dissolved in acetonitrile (100 mL) and borontrifluoride etherate (14.88 mL) was added. The reaction and workup were identical to that in example 20 giving the desired product (16.89 g, 67%).

EXAMPLE 22

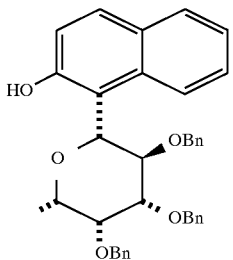

2-Naphthol (1.00 g, 7.01 mmole) and tri-O-benzyl 1-O-acetylfucose (2.22 g, 4.67 mmoles) were dissolved in acetonitrile (15 mL) and 4 Å molecular sieves (2.00 g) were added. After adding borontrifluoride etherate (1.72 mL), the reaction was stirred at room temperature for three days and quenched with 6N HCl (10 mL). After stirring at room temperature for 2 hours, the reaction was neutralized with saturated aqueous sodium bicarbonate. The resulting mixture was washed with ethyl acetate (2×50 mL) and brine (2×25 mL). After drying over anhydrous magnesium sulfate, the solution was filtered, concentrated and the product purified on silica gel (10% ethyl acetate/hexane) to give the desired product (2.05 g, 78%).

EXAMPLE 23

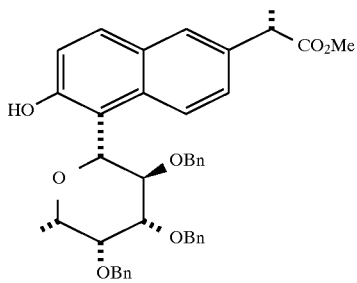

6-O-Demethyl naproxen methyl ester (1.00 g, 4.35 mmole) and tri-O-benzyl 1-O-acetylfucose (1.38 g, 2.90 mmoles) were dissolved in acetonitrile (10 mL) and 4 Å molecular sieves (2.00 g) were added. After adding borontrifluoride etherate (1.07 mL), the reaction was stirred at room temperature for two days and quenched with 6N HCl (10 mL). After stirring at room temperature for 40 minutes, the reaction was neutralized with saturated aqueous sodium bicarbonate. The resulting mixture was washed with ethyl acetate (3×20 mL). After drying over anhydrous magnesium sulfate, the solution was filtered, concentrated and the product purified on silica gel (hexane then 10% acetone/hexane then 15% acetone/hexane) to give the desired product (1.44 g, 77%).

EXAMPLE 24

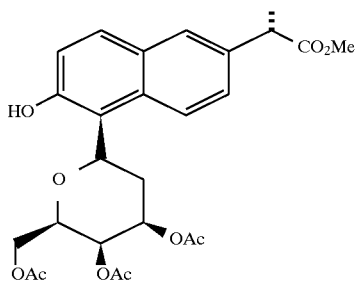

6-O-Demethyl naproxen methyl ester and tetra-O-acetyl 2-deoxygalactose are dissolved in acetonitrile and borontrifluoride etherate is added. The reaction and workup are identical to that in Example 20.

EXAMPLE 25

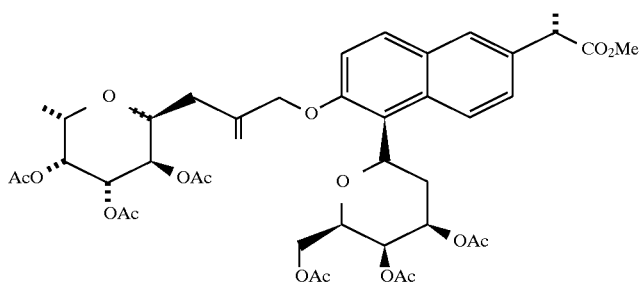

The product from example 24 and 1-deoxy-1-α-3-chloromethallyl)-2,3,4-tri-O-acetylfucose are dissolved in dimethylformamide and potassium carbonate is added followed by tetrabutyl ammoniumiodide. After stirring at room temperature for 2 days, the reaction is diluted with ethyl acetate and washed with saturated aqueous sodium bicarbonate (3×) and brine (2×). The mixture is dried over anhydrous magnesium sulfate, filtered and concentrated. The residue is purified on silica gel to give the desired product.

EXAMPLE 26

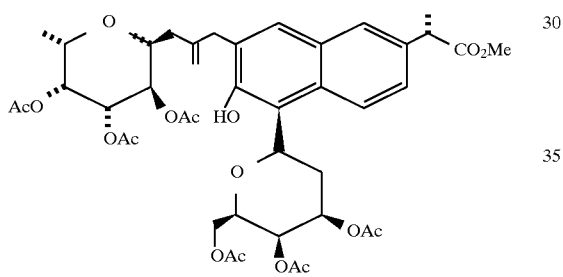

The product from Example 25 is dissolved in 1,2-dichlorobenzene and heated to 190 degrees C for six hours. After cooling to room temperature, reaction mixture is separated on silica gel giving the desired product.

EXAMPLE 26

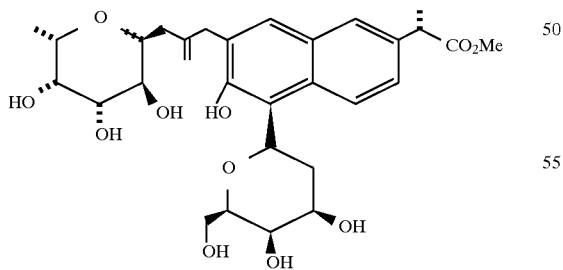

Sodium metal (4 spheres) are washed in hexane and added to anhydrous methanol (20 mL). 0.10 mL of the resulting sodium methoxide solution is added to a solution of the product from Example 25 in anhydrous methanol (10 mL). After stirring at room temperature for 24 hours, the reaction is concentrated to dryness giving the desired product.

EXAMPLE 27

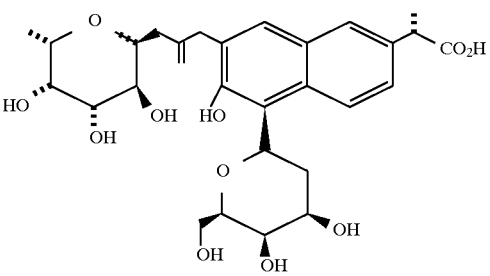

The product from example 26 is dissolved in methanol and an equivalent volume of aqueous 2N NaOH (2 equivalents) is added. The reaction is stirred at room temperature for 24 hours and neutralized methanol washed Amberlyst acidic ion exchange resin. Filtration and concentration of the resulting solution provides the desired product.

EXAMPLE 28

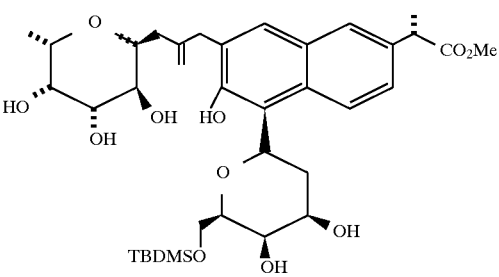

The product from Example 26 is dissolved in methylene chloride/dimethyl formamide (20/1) and TBDMS-Cl (0.53 g, 3.51 mmoles) is added followed by imidazole (0.34 g, 5.02 mmoles). After stirring at room temperature for 20 hours, TBDMS-Cl (0.53 g, 3.51 mmoles) and imidazole (0.34 g, 5.02 mmoles) are added. Stirring is continued for an additional 20 hours after which, the reaction is quenched with methanol (10 mL). After stirring for 30 minutes at room temperature, the reaction is concentrated to dryness and the product is purified on silica gel.

EXAMPLE 29

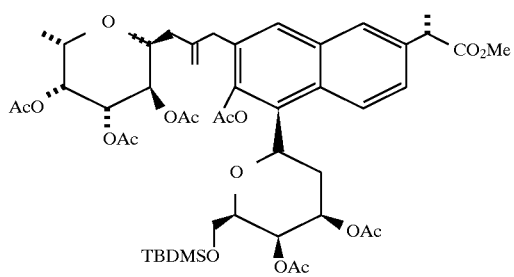

The product from Example 28 is dissolved in pyridine and an equivalent volume of acetic anhydride is added. After stirring at room temperature for three days, the reaction is concentrated to dryness and the residue is dissolved in ethyl acetate. After washing with 1N HCl (3x), saturated aqueous sodium bicarbonate (6x), water, saturated aqueous copper sulfate (2x), and brine (10 mL), the organic phase is dried over anhydrous magnesium sulfate, filtered and concentrated to dryness giving the desired product (1.98 g, 81%).

EXAMPLE 30

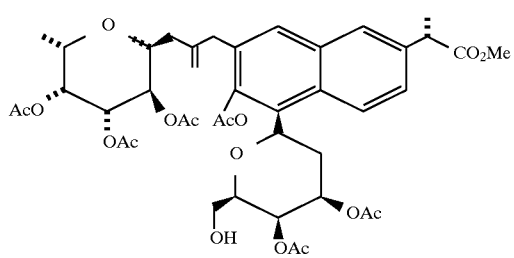

The product described in Example 29 is dissolved in tetrahydrofuran and tetrabutyl ammonium fluoride (1M in THF) is added. After stirring at room temperature for five days, the reaction is concentrated. Purification of the residue on silica gel gives the desired product.

EXAMPLE 31

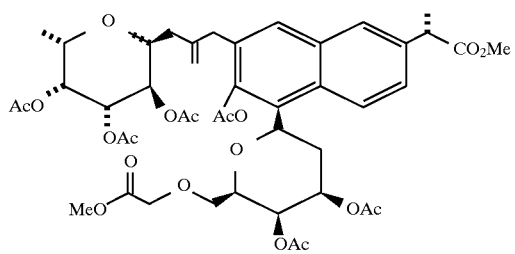

The product described in Example 30 and methyl bromoacetate are dissolved in tetrahydrofuran and sodium hydride (60% in mineral oil) is added. After stirring at room temperature for 2 days, the reaction is quenched with saturated aqueous sodium bicarbonate. The reaction is diluted with ethyl acetate and washed with brine (2x). After drying over anhydrous magnesium sulfate, the organic phase is filtered and concentrated. Purification of the residue on silica gel gives the product.

EXAMPLE 32

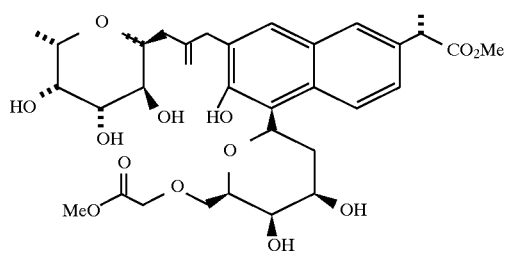

Sodium metal (4 spheres) are washed in hexane and added to anhydrous methanol (20 mL). 0.10 mL of the resulting sodium methoxide solution is added to a solution of the product from Example 31 in anhydrous methanol. After stirring at room temperature for 24 hours, the reaction is concentrated to dryness giving the desired product.

EXAMPLE 33

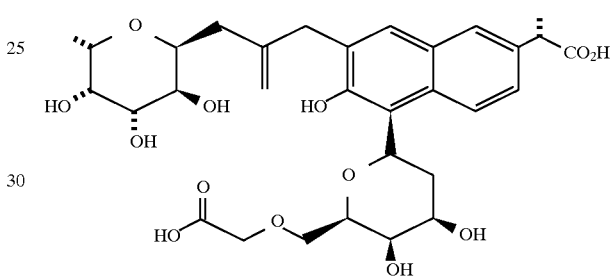

The product described in Example 32 is dissolved in methanol and an equivalent volume of 2N aqueous sodium hydroxide (4 equivalents) is added. The reaction is stirred at room temperature for 20 hours and neutralized with methanol washed Amberlyst acidic ion exchange resin. Filtration and concentration of the resulting solution provides the desired product.

EXAMPLE 34

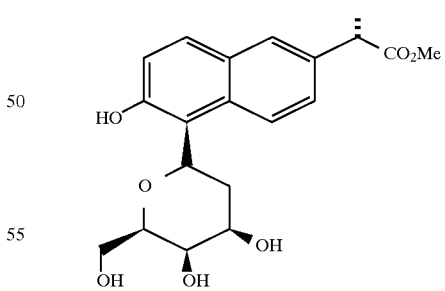

Sodium metal (4 spheres) were washed in hexane and added to anhydrous methanol (20 mL). 0.20 mL of the resulting sodium methoxide solution is added to a solution of the product from Example 28 in anhydrous methanol. After stirring at room temperature for 24 hours, the reaction is neutralized with amberlite acidic ion exchange resin. After removal of the resin by filtration, the filtrate is concentrated to dryness giving the desired product.

EXAMPLE 35

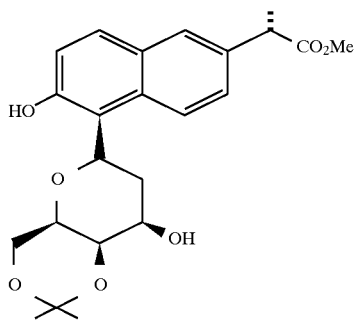

The product from Example 34 is dissolved in 2,2-dimethoxypropane and camphorsulfonic acid is added. After stirring at room temperature for 24 hours, the reaction is concentrated to dryness. The residue is dissolved in ethyl acetate and washed with saturated aqueous sodium bicarbonate (3×) and brine. After drying over anhydrous magnesium sulfate, the organic phase is filtered and concentrated to dryness giving the desired product.

EXAMPLE 36

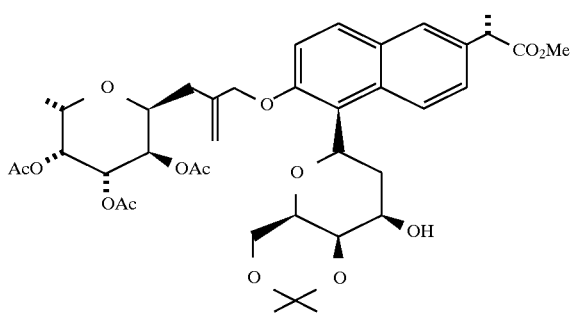

The product described in Example 35 and 1-deoxy-1-α-(3-chloromethallyl)-2,3,4-tri-O-acetylfucose are dissolved in dimethylformamide and potassium carbonate is added followed by tetrabutyl ammoniumiodide. After stirring at room temperature for 6 days, the reaction is diluted with ethyl acetate and washed with saturated aqueous sodium bicarbonate (3×) and brine (2×). The mixture is dried over anhydrous magnesium sulfate, filtered and concentrated. The residue is purified on silica gel to give the desired product.

EXAMPLE 37

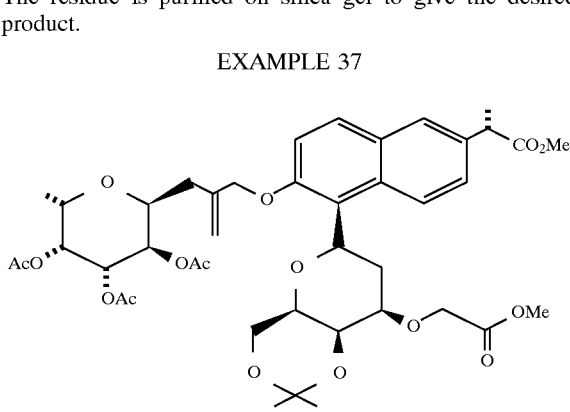

This product is prepared from the product of Example 36 using methodology similar to that used in Example 34.

EXAMPLE 38

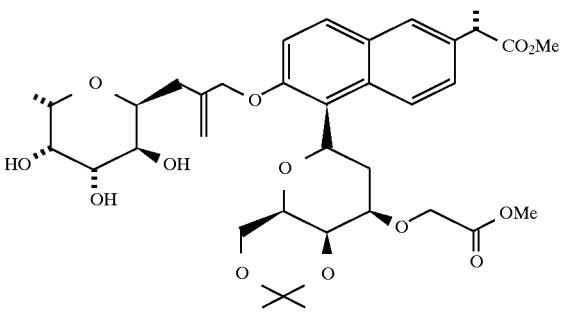

This product is prepared from the product of Example 37 using methodology similar to that used in Example 34.

EXAMPLE 39

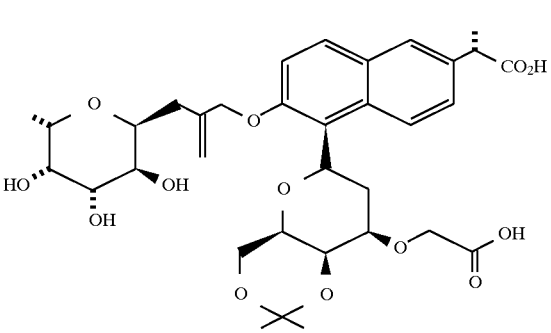

This product is prepared from the product of example 38 using methodology similar to that used in Example 33.

EXAMPLE 40

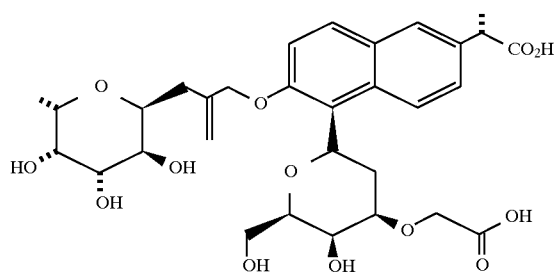

The product from Example 39 is dissolved in tetrahydrofuran and an equivalent volume of 6N hydrochloric acid is added. After stirring at room temperature for 24 hours, the reaction is concentrated to dryness to give the desired product.

EXAMPLE 41

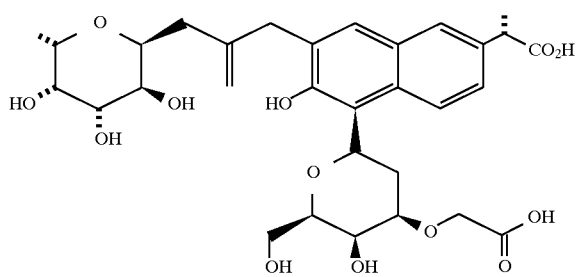

This product is prepared from the product of Example 40 using methodology similar to that used in Example 26.

EXAMPLE 42

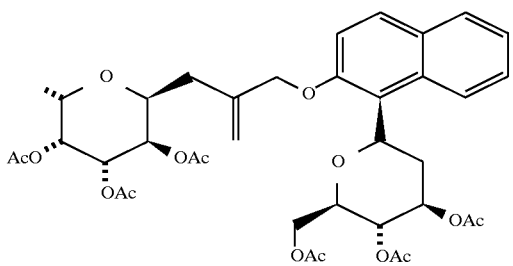

The product from example 20 (10.54 g, 25.34 mmoles) and 1-deoxy-1-α-(3-chloromethallyl)-2,3,4-tri-O-acetylfucose (10.09 g, 27.87 mmoles) were dissolved in dimethylformamide (100 mL) and potassium carbonate (7.00 g, 50.67 mmoles) was added followed by tetrabutyl ammoniumiodide (0.94 g, 2.53 mmoles). After stirring at room temperature for 2 days, the reaction was diluted with ethyl acetate (300 mL) and washed with saturated aqueous sodium bicarbonate (3×50 mL) and brine (2×50 mL). The mixture was dried over anhydrous magnesium sulfate, filtered and concentrated. The residue was purified on silica gel (30% ethyl acetate/hexane) to give the desired product (12.83 g, 68%).

EXAMPLE 43

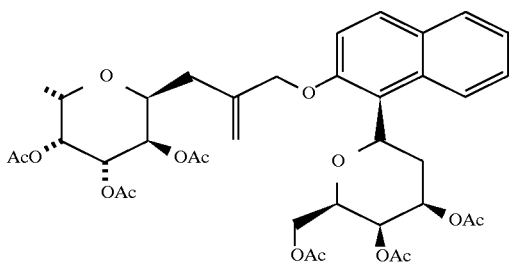

The product from Example 21 (16.89 g, 40.60 mmoles) and 1-deoxy-1-α-(3-chloromethallyl)-2,3,4-tri-O-acetylfucose (15.43 g, 42.63 mmoles) were dissolved in dimethylformamide (100 mL) and potassium carbonate (11.22 g, 81.20 mmoles) was added followed by tetrabutyl ammoniumiodide (1.50 g, 4.06 mmoles). After stirring at room temperature for 2 days, the reaction was diluted with ethyl acetate (300 mL) and washed with saturated aqueous sodium bicarbonate (3×50 mL) and brine (2×50 mL). The mixture was dried over anhydrous magnesium sulfate, filtered and concentrated. The residue was purified on silica gel (30% ethyl acetate/hexane) to give the desired product (27.12 g, 90%).

EXAMPLE 44

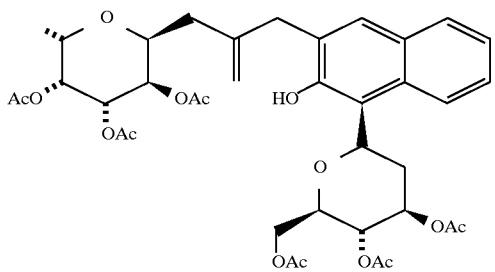

The product from Example 42 (6.13 g, 8.26 mmoles) was dissolved in 1,2-dichlorobenzene (16.60 mL) and heated to 190 degrees C for six hours. After cooling to room temperature, reaction mixture was separated on silica gel giving the desired product (3.23 g, 53%).

EXAMPLE 45

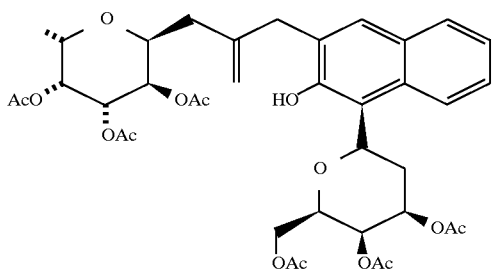

The product from Example 43 (6.38 g, 8.60 mmoles) was dissolved in 1,2-dichlorobenzene (17.00 mL) and heated to 190 degrees C for six hours. After cooling to room temperature, reaction mixture was separated on silica gel giving the desired product (2.28 g, 36%).

EXAMPLE 46

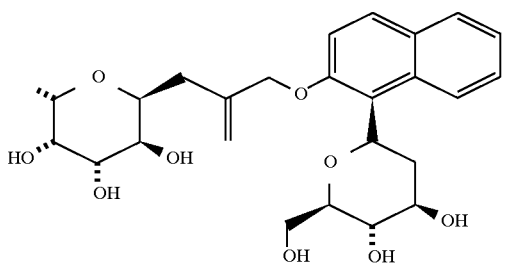

Sodium metal (4 spheres) were washed in hexane and added to anhydrous methanol (20 mL). 0.10 mL of the resulting sodium methoxide solution was added to a solution of the product from Example 42 (3.05 g, 4.11 mmoles) in anhydrous methanol (20 mL). After stirring at room temperature for 24 hours, the reaction was concentrated to dryness giving the desired product (2.10 g, 100%).

EXAMPLE 47

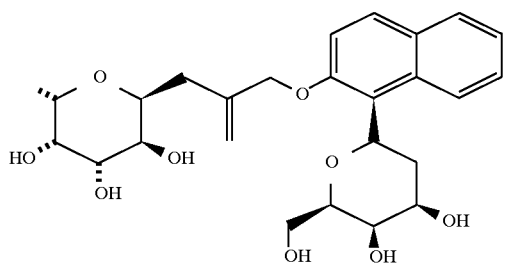

Sodium metal (4 spheres) were washed in hexane and added to anhydrous methanol (20 mL). 0.10 mL of the resulting sodium methoxide solution was added to a solution of the product from Example 43 (4.97 g, 6.70 mmoles) in anhydrous methanol (20 mL). After stirring at room temperature for 24 hours, the reaction was concentrated to dryness giving the desired product (3.45 g, 100%).

EXAMPLE 48

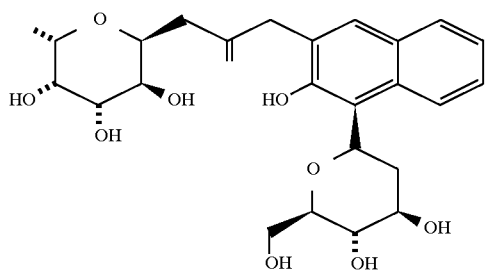

Sodium metal (4 spheres) were washed in hexane and added to anhydrous methanol (20 mL). 0.10 mL of the resulting sodium methoxide solution was added to a solution of the product from Example 44 (3.23 g, 4.35 mmoles) in anhydrous methanol (10 mL). After stirring at room temperature for 24 hours, the reaction was concentrated to dryness giving the desired product (2.14 g, 100%).

EXAMPLE 49

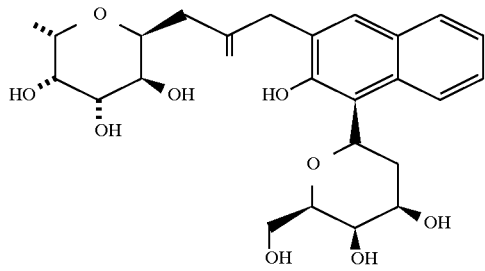

Sodium metal (4 spheres) were washed in hexane and added to anhydrous methanol (20 mL). 0.10 mL of the resulting sodium methoxide solution was added to a solution of the product from Example 45 (2.28 g, 3.07 mmoles) in anhydrous methanol (10 mL). After stirring at room temperature for 24 hours, the reaction was concentrated to dryness giving the desired product (1.55 g, 100%).

EXAMPLE 50

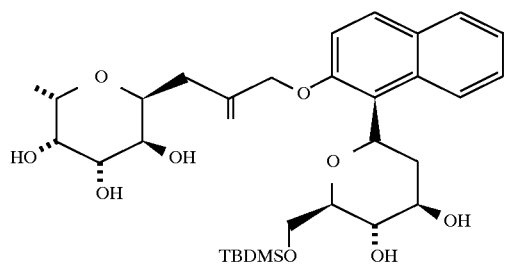

The product from Example 46 (1.64 g, 3.35 mmoles) was dissolved in methylene chloride (20 mL) and dimethyl formamide (1 mL) and TBDMS-Cl (0.53 g, 3.51 mmoles) was added followed by imidazole (0.34 g, 5.02 mmoles). After stirring at room temperature for 20 hours, TBDMS-Cl (0.53 g, 3.51 mmoles) and imidazole (0.34 g, 5.02 mmoles) were added. Stirring was continued for an additional 20 hours after which, the reaction was quenched with methanol (10 mL). After stirring for 30 minutes at room temperature, the reaction was concentrated to dryness and the product was purified on silica gel (10% methanol/chloroform, 1.81 g, 90%).

EXAMPLE 51

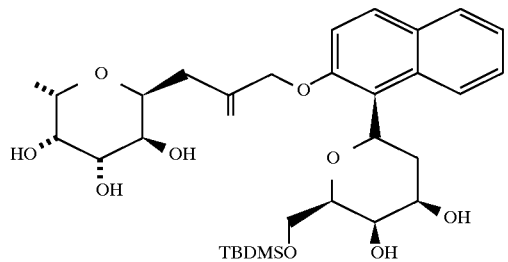

This product (1.65 g, 46%) was prepared from the compound described in Example 47 using similar conditions to those described in Example 50.

EXAMPLE 52

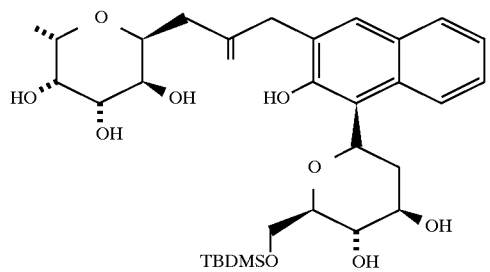

This product (1.76 g, 80%) was prepared from the compound described in Example 48 using similar conditions to those described in Example 50.

EXAMPLE 53

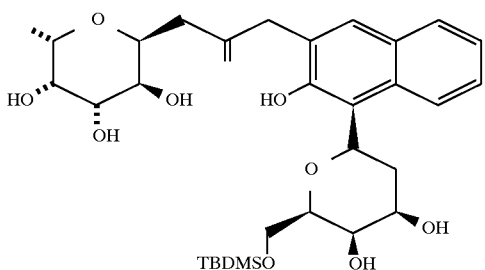

This product (1.02 g, 64%) was prepared from the compound described in Example 49 using similar conditions to those described in Example 50.

EXAMPLE 54

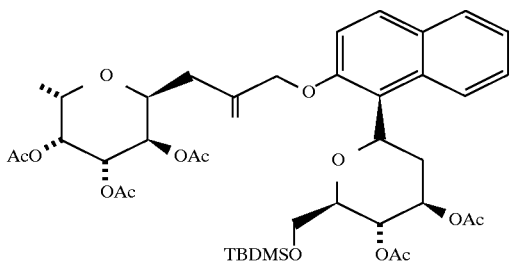

The product from Example 50 (1.81 g, 3.00 mmoles) was dissolved in pyridine (5.00 mL) and acetic anhydride (5.00 mL) was added. After stirring at room temperature for three days, the reaction was concentrated to dryness and the residue was dissolved in ethyl acetate (50 mL). After washing with 1N HCl (3×10 mL), saturated aqueous sodium bicarbonate (6×10 mL), water (10 mL), saturated aqueous copper sulfate (2×10 mL), and brine (10 mL), the organic phase was dried over anhydrous magnesium sulfate, filtered and concentrated to dryness giving the desired product (1.98 g, 81%).

EXAMPLE 55

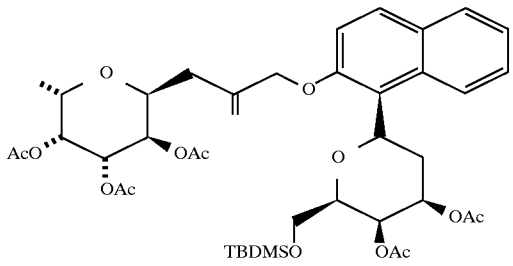

This product (3.04 g, 70%) was prepared from the compound described in Example 51 using similar conditions to those described in Example 54.

EXAMPLE 56

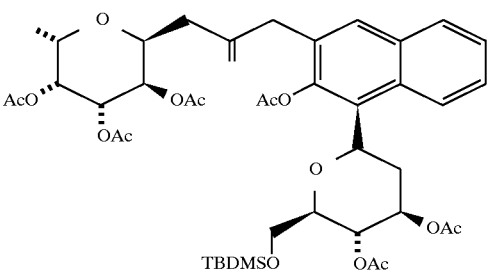

This product (2.07 g, 83%) was prepared from the compound described in Example 52 using similar conditions to those described in Example 54.

EXAMPLE 57

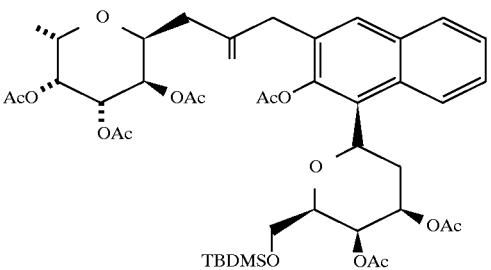

This product (1.24 g, 86%) was prepared from the compound described in Example 53 using similar conditions to those described in Example 54.

EXAMPLE 58

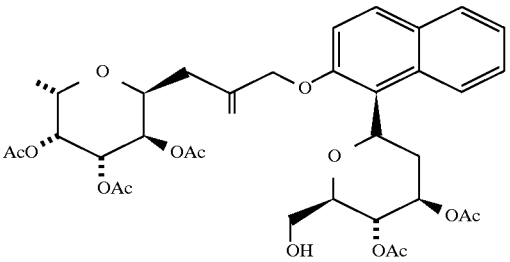

The product described in Example 54 (1.98 g, 2.43 mmoles) was dissolved in tetrahydrofuran (10 mL) and tetrabutyl ammoniumfluoride (1M in THF, 2.68 mL, 2.68 mmoles) was added. After stirring at room temperature for five days, the reaction was concentrated. Purification of the residue on silica gel (50% ethyl acetate/hexane) gave the desired product (1.29 g, 76%).

EXAMPLE 59

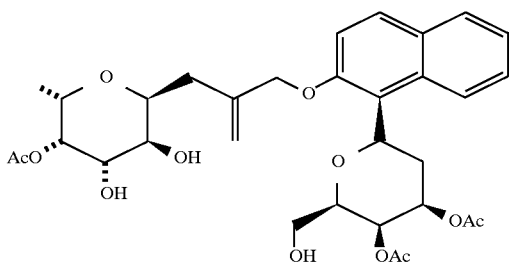

This product (0.87 g, 69%) was prepared from the compound described in Example 55 using similar conditions to those described in Example 58.

EXAMPLE 60

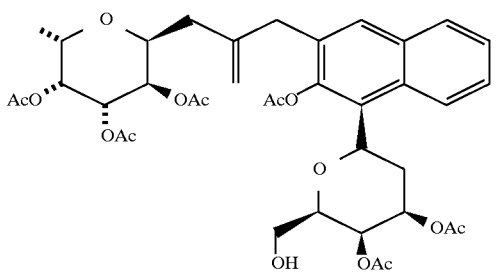

This product (0.96 g, 63%) was prepared from the compounds described in Example 56 using similar conditions to those described in Example 58.

EXAMPLE 61

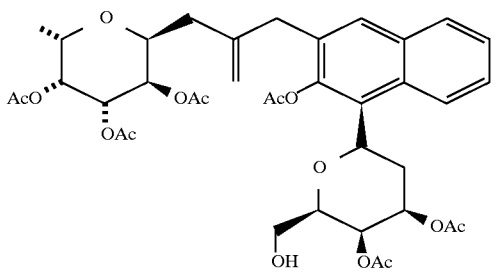

This product (0.83 g, 94%) was prepared from the compound described in Example 57 using similar conditions to those described in Example 58.

EXAMPLE 62

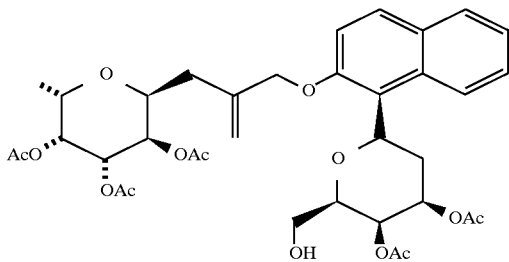

The compound described in Example 58 (1.29 g, 1.84 mmoles) was dissolved in carbon tetrachloride (4 mL), acetonitrile (4 mL), and water (6 mL). After adding sodium periodate (1.58 g, 7.37 mmoles), the reaction was cooled to zero degrees C. Ruthenium trichloride hydrate (8.4 mg, 0.41 mmoles) was added and the reaction was vigorously stirred for four hours while warming to room temperature. The reaction was then diluted with ethyl acetate (100 mL) and washed with water (2×20 mL), saturated aqueous sodium bicarbonate (3×20 mL), and brine (20 mL). After drying over anhydrous magnesium sulfate, organic phase was filtered, concentrated, and purified on silica gel (70% ethyl acetate/hexane) giving the product (0.86 g, 65%).

EXAMPLE 63

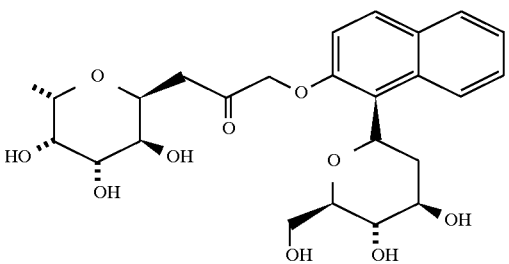

The product described in Example 62 (0.86 g, 120 mmoles) was dissolved in methanol (7.23 mL) and 2N aqueous sodium hydroxide (7.23 mL) was added. After stirring at room temperature for 24 hours, the methanol was evaporated and the aqueous residue was acidified with 6N HCl to pH=2. The water was then removed on a lyophilizer. The salt components of the residue were removed by washing with minimal amounts of methanol and removing the solids by filtration. Concentration of the filtrate provided the product (0.62 g, 100%).

EXAMPLE 64

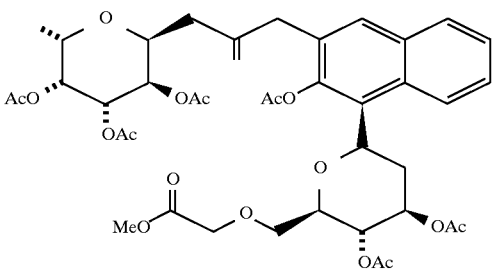

The product described in Example 60 (0.96 g, 1.29 mmoles) and methyl bromoacetate (0.18 mL, 1.94 mmoles) were dissolved in tetrahydrofuran (2.00 mL) and sodium hydride (60% in mineral oil, 62 mg, 1.55 mmoles) was added. After stirring at room temperature for 2 days, the reaction was quenched with saturated aqueous sodium bicarbonate (10 mL). The reaction was diluted with ethyl acetate (50 mL) and washed with brine (2×25 mL). After drying over anhydrous magnesium sulfate, the organic phase was filtered and concentrated. Purification of the residue on silica gel (50% ethyl acetate/hexane) gave the product (0.53 g, 50%).

EXAMPLE 65

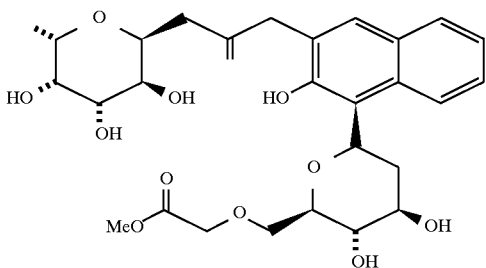

Sodium metal (4 spheres) were washed in hexane and added to anhydrous methanol (20 mL). 0.10 mL of the resulting sodium methoxide solution was added to a solution of the product from Example 64 (0.53 g, 0.65 mmoles) in anhydrousmethanol (10 mL). After stirring at room temperature for 24 hours, the reaction was concentrated to dryness giving the desired product (0.36 g, 99%).

EXAMPLE 66

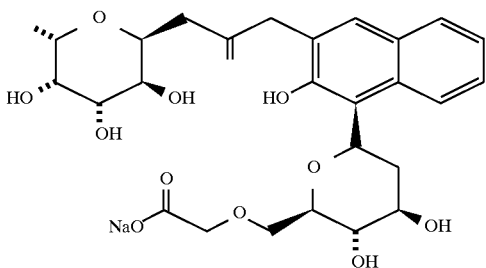

The product described in Example 65 (0.36 g, 0.64 mmoles) was dissolved in methanol (0.64 mL) and 2N aqueous sodium hydroxide (0.64 mL, 1.28 mmoles) was added. The reaction was stirred at room temperature for 20 hours and the methanol was removed under reduced pressure. The residue was dissolved in water (20 mL) and the water was removed on a lyophilizer giving the desired product (0.39 g, 100%).

EXAMPLE 67

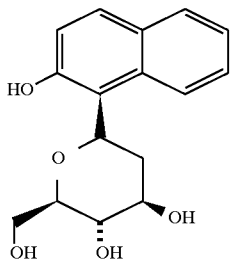

Sodium metal (4 spheres) were washed in hexane and added to anhydrous methanol (20 mL). 0.20 mL of the resulting sodium methoxide solution was added to a solution of the product from Example 20 (12.29 g) in anhydrous methanol (20 mL). After stirring at room temperature for 24 hours, the reaction was neutralized with amberlite acidic ion exchange resin. After removal of the resin by filtration, the filtrate was concentrated to dryness giving the desired product (7.90 g, 92%).

EXAMPLE 68

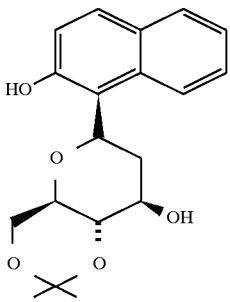

The product from Example 67 (7.90 g, 27.24 mmoles) was dissolved in 2,2-dimethoxypropane (100 mL) and camphorsulfonic acid (0.32 g, 1.36 mmoles) was added. After stirring at room temperature for 24 hours, the reaction was concentrated to dryness. The residue was dissolved in ethyl acetate (300 mL) and washed with saturated aqueous sodium bicarbonate (3×50 mL) and brine (50 mL). After drying over anhydrous magnesium sulfate, the organic phase was filtered and concentrated to dryness giving the desired product (8.44 g, 94%).

EXAMPLE 69

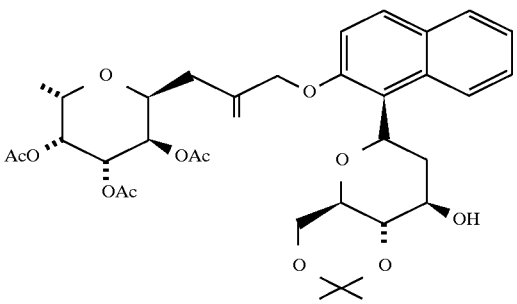

The product described in Example 68 (8.44 g, 25.58 mmoles) and 1-deoxy-1-α-(3-chloromethallyl)-2,3,4-tri-O-acetylfucose (10.18 g, 28.13 mmoles) were dissolved in dimethylformamide (100 mL) and potassium carbonate (7.07 g, 51.15 mmoles) was added followed by tetrabutyl ammoniumiodide (0.94 g, 2.53 mmoles). After stirring at room temperature for 6 days, the reaction was diluted with ethyl acetate (300 mL) and washed with saturated aqueous sodium bicarbonate (3×50 mL) and brine (2×50 mL). The mixture was dried over anhydrous magnesium sulfate, filtered and concentrated. The residue was purified on silica gel (50%. ethyl acetate/hexane) to give the desired product (14.04 g, 84%).

Example A

Selectin Binding

An ELISA assay was employed that uses recombinant fusion proteins composed of extracellular portions of the human selectins joined to human immunoglobulin heavy chain $CH_3$, $CH_2$, and hinge regions. See, for example, Walz et al., Science (1990) 250:1132; Aruffo et al., Cell (1991) 67:35; Aruffo et al., Proc. Natl. Acad. Sci. USA (1992) 89:2292. The assay is well known in the art, and generally consists of the following three steps:

I. 2,3 sLe$^x$ glycolipid (25 picomole/well) was transferred into microliter well as solutions and then evaporated off. Excess, which remained unattached, was washed off with water. The wells were then blocked with 5% BSA at room temperature for an hour and then washed with PBS containing 1 mM calcium.

II. Preparation of "multivalent" receptor of the Selectin-IgG chimera was carried out by combining the respective chimera 1 μg/ml) with biotin labelled goat F(ab')2 anti-human IgG (Fc specific) and streptavidin-alkaline phosphatase diluted 1:1000 in 1% BSPBS (1 mM calcium) and incubating at 37° C. for 15 min. This allowed the soluble multivalent receptor complex to form.

III. Potential inhibitors such as compounds of formula I were allowed to react with the soluble receptor at 37° C. for 45 min. This test assumes that optimal binding, between the soluble phase receptor complex and the inhibitor (non-natural ligand), would have occurred within this time frame. This solution was then placed in the microliter wells that were prepared in step I. The plate was incubated at 37° C. for 45 minutes to allow the soluble receptor to bind to its natural ligand. In the presence of a strong inhibitor only a few receptors should be free to bind to the microliter plate coated with the natural ligand.

The positive control is the signal produced by the soluble receptor when it is allowed to react with 2,3 sLe$^x$ glycolipid in the microliter wells in the absence of any inhibitor. This was considered 100% binding. The signal produced by the receptor that had been previously treated with an inhibitor (recorded as O.D.), was divided by the signal produced by the positive control and multiplied by 100 to calculate the % receptor bound to the well, or the percent of control binding. Several of the compounds described herein were tested using this assay. Tables 2 and 3 list the extent to which the invention compounds inhibit binding of E, L and P-selectin to 2,3 sLe$^x$ glycolipid in terms of $IC_{50}$ values.

TABLE 2

Naphthoic Acid C-Glycosides

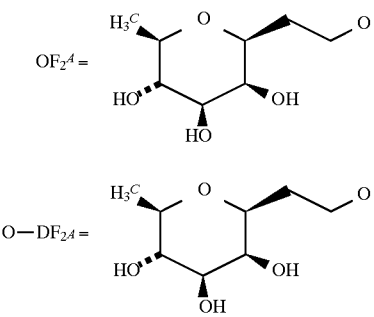 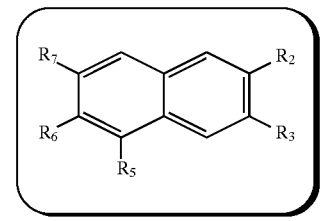

| $R_2$ | $R_3$ | $R_5$ | $R_6$ | $R_7$ | E ($IC_{50}$, mM) | L ($IC_{50}$, mM) | P ($IC_{50}$, mM) |
|---|---|---|---|---|---|---|---|
| $CO_2H$ | H | H | $OF_2^A$ | H | <0.5 >1.5 | <1.0 >1.5 | <0.5 >1.5 |
| $CH(CH_3)CO_2H$ | H | H | $OF_2^A$ | H | >4.0 | >2.0 | >2.0 |
| $CO_2H$ | $OF_2^A$ | H | H | $OF_2^A$ | >4.0 >1.5 | <2.0 >1.5 | <0.5 >1.5 |
| $CO_2H$ | $OF_2^A$ | $OF_2^A$ | H | H | >4.0 | <4.0 | <2.0 |
| $CO_2H$ | H | H | $O\text{-}DF_2^A$ | H | >1.5 | >1.5 | >1.5 |
| $CO_2H$ | $OF_2^A$ | H | H | $O\text{-}DF_2^A$ | >1.5 | >1.5 | >1.5 |
| $CH(CH_3)CO_2H$ | H | H | $OF_1^A$ | H | >1.0 | >1.0 | >1.0 |

TABLE 3

Naphthol-C-Glycosides

| EXAMPLE | R" | R$_5$ | R$_6$ | R$_7$ | E (IC$_{50}$, mM) | L (IC$_{50}$, mM) | P (IC$_{50}$, mM) |
|---------|-----|-------|-------|-------|-------------------|-------------------|-------------------|
| | H | OR' (structure) | H | F$_1^A$ | Ins | Ins | Ins |
| | H | OR' (structure) | F$_1^A$ | H | Ins | Ins | Ins |
| | H | OR' (structure) | F$_1^A$ | H | >4.0 | >4.0 | >4.0 |
| | H | OR' (structure) | H | F$_1^A$ | >1.5 | >1.5 | >1.5 |
| | H | OR' (structure) | F$_1^C$ | H | >1.5 | >1.5 | >1.5 |
| | CH$_2$CO$_2$OH | OR' (structure) | H | F$_1^A$ | >2.0 | >2.0 | >2.0 |

In addition to the ligands described above, other ligands could be obtained by selecting more rigid spacers in order to maintain the appropriate statistical average distance between the sialic acid and fucose moieties in space thereby improving the inhibitory property of such structures towards the selecting. Further modifications of these compounds e.g., attaching them through chemical linkages on appropriate molecular supports and use of analogs or derivatives of sialic acid and L-fucose are also considered to be within the scope of the present invention.

Example B

Flow Cytometric Assay for P-selectin Ligand

The interaction of P-selectin and its cellular ligand was studied using a flow cytometric assay (Erbe, D. V. et al., J. Cell Biol. (1993) 120:1227). HL60 cells (maintained in high glucose DME plus 10% Hyclone FBS) were used in this assay. Before staining with P-selectin-IgG the cells were preincubated in Dulbecco's PBS/1% BSA/0.1% sodium azide/1% normal rabbit serum (staining medium) for 30–60 mins on ice. After this initial incubation, 1 µg of P-selectin-IgG was added to 100 µl aliquots of 106 cells and incubated for 30–60 mins on ice. The cells were then washed with staining medium and resuspended in 100 µl of staining medium to which was added 2 µl of a phycoerythrin-conjugated F(ab')$^2$ goat anti-human IgG (Fc specific). The cells were incubated for 15–30 mins on ice, washed twice with staining medium, and resuspended in 0.5 ml of staining medium before flow cytometric analysis on a FACScan (Becton Dickinson & Co., Mountain View, Calif.). To determine that the staining was an interaction of P-selectin with its ligand, the staining was also done in the presence of 10 mM EGTA. To determine the protease sensitivity and the requirement for sialic acid of this interaction, HL-60 cells in D-PBS and 1% BSA were incubated with either trypsin or Arthrobacter or Clostridium sialidases at 37° C. before resuspending in staining medium. To examine the ability of various carbohydrates to inhibit staining, 50 μg/ml fucoidin (Sigma Immunochemicals, St. Louis, Mo.), 50 μg/ml dextran sulfate (Pharmacia Fine Chemicals, Piscataway, N.J.), 10 mg/ml mannose-1-phosphate (Sigma Immunochemicals), or 10 mg/ml mannose-6-phosphate (Sigma Immunochemicals) was added to cells immediately before the addition of the P-selectin chimera. Each carbohydrate was then present until the cells were washed before the addition of the second stage antibody. A potential complication of this FACS assay arose from the use of selectin-IgG chimeras to stain cells which bear human IgG Fc receptors (FcYR; Fanger, M. W., et al., *Immunol.* (1989) 10:92). Adding rabbit IgG (in the form of normal rabbit serum) to the assay medium blocked this binding in most cases. Table 4 shows the results (in terms of % inhibition) of the ability of compounds C and D, 6-O-sulfo-hexanyl-α-L-furopyranoside, to inhibit P-selectin-IgG binding to HL-60 cells lines. The structure of compound C is shown below:

TABLE 4

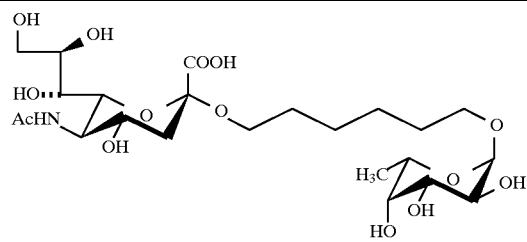

| Compound # | Concentration (mg/ml) | Inhibition (%) |
|---|---|---|
| C | 10 | 60 |
|   | 50 | 80 |
|   | 100 | 80 |
| D | 10 | 50 |
|   | 100 | 50 |
|   | 200 | 60 |

Example C

Treatment of Sepsis

A number of the complications associated with sepsis arise from unwanted neutrophil extravasation and adhesion of the neutrophils to the endothelium. The invention compounds would be used to prevent or treat sepsis.

The effectiveness of these compounds would be shown in a baboon sepsis model system as described by Taylor et al., *J. of Clinical Inv.*, (1987), 79:918, and by Taylor, et al., *Circulatory Shock*, (1988), 26:227. Briefly this model would consist of determining if the compounds are effective in treating sepsis by preventing the death, or prolonging the lives of septic animals to either a letal or sublethal dose of *E. coli*. A lethal or sublethal dose of *E. coli* consists of approximately $4 \times 10^{10}$ and $0.4 \times 10^{10}$ organisms, respectively. Baboons that receive a lethal dose of *E. coli* invariably die within 16–32 hours. Taylor, et al., *J. of Clinical Inv.* (1987), 79:918, and Taylor et al., *Circulatory Shock*, (1988), 26:227.

Thus, the procedure would consist of using two administration routines for each of the compounds tested wherein they are delivered in physiological saline. In the first, between 1 and 10 mg of compound per kg of body weight is administered in three separate doses at 24, 22, and 21 hours before a lethal challenge of bacteria. Alternatively, compound can be administered in a single dose simultaneously with the bacterial challenge. In both instances the compounds would considerably extend the lifetime of the baboons that receive the multiple or single dose treatment and they would survive well beyond 48 hours.

Example D

Reperfusion Injury Assay

Experiments were done to determine the effectiveness of compound C in decreasing adhesion of human neutrophils in the rabbit isolated heart. Addition of the human plasma to the rabbit isolated heart results in activation of the complement components found within the plasma, which in turn promotes an increase in the neutrophil accumulation. This model is used to determine the effect of $sLe^x$ analogues on inhibiting complement-induced neutrophil adhesion.

Hearts from New Zealand White rabbits were excised, mounted on a modified Langendorff apparatus and perfused with Krebs-Heinseleit buffer. Cardiac functional parameters were monitored upon a Grass Model 79D polygraph machine. 4% normal human plasma (NHP) was added to the recirculating buffer. Ten minutes after the addition of the plasma, Compound C (0.1 20 mg/ml) was added to the perfusate. After 15 minutes of perfusion with the plasma, 51-chromium labelled human neutrophils ($1 \times 10^5$/ml) were added to the perfusate and allowed to recirculate for an additional 15 minutes. At the end of this time the hearts were washed with fresh buffer to remove non-specifically bound neutrophils, dried and counted in a well-type gamma-counter. A concentration response curve was generated using concentrations of 0.001, 0.01 and 0.1 mg/ml. Six hearts were used for each of these concentrations. 30 Percent inhibition of neutrophil accumulation was found. These results are expressed as the number of radiolabelled human neutrophils/mg of dry weight of the heart.

It should also be noted that the greatest degree of inhibition seen using pharmacological agents, including a number of peptides derived form P-selectin and antibodies directed against P-selectin and the CD1 1b/CD18 complex (Ma, Xin-liang, et al., *Circulation* (1993) 88-2:649), has been 40%. Compound C provides a degree of inhibition (30%) similar to any of the pharmacological agents tested thus far.

Based on the above results, it is apparent that the compounds of the invention are useful for treating diseases, preferably diseases that have an inflammatory component-Adult Respiratory Distress Syndrome (ARDS), ischemia and reperfusion injury, including strokes, mesenteric and peripheral disease, organ transplantation, and circulatory shock (in this case one or many organs might be damage following restoration of blood flow).

What is claimed:

1. A compound of the formula I:

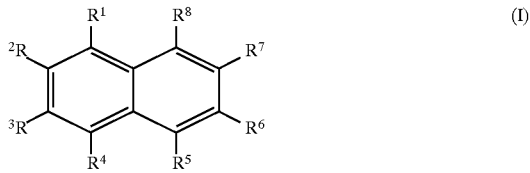

wherein
$R^1$, $R^2$, $R^3$, $R^4$, $R^5$, $R^6$, $R^7$, and $R^8$ are independently selected from the group consisting of
(a) —H, Y—B, alkyl of 1 to 4 carbon atoms optionally substituted with 1 to 2 lower alkyl groups, —W((CH$_2$)$_n$—B)$_t$, —W((CH$_2$)$_m$—(CHR$^9$)$_q$—(CH$_2$)$_m$—A)$_t$;

—OH, lower alkoxy, lower aryloxy, lower aralkoxy, lower alkoxyaryl, amino, —W((CH$_2$)$_n$—A)$_t$, —O—CH$_2$—C≡C—B, —N(Ac)—CH$_2$—C≡C—B, —NH—CH$_2$—C≡C—B, —N(CH$_2$—C≡C—B)$_2$, —N(Ac)CH$_2$Ar—B, —NHCH$_2$Ar—B, —N(CH$_2$Ar—B)$_2$, —OCH$_2$Ar—B, —(C=O) (CH$_2$)$_m$—B, and (b) A and B; wherein:

Y—B is selected from the group consisting of

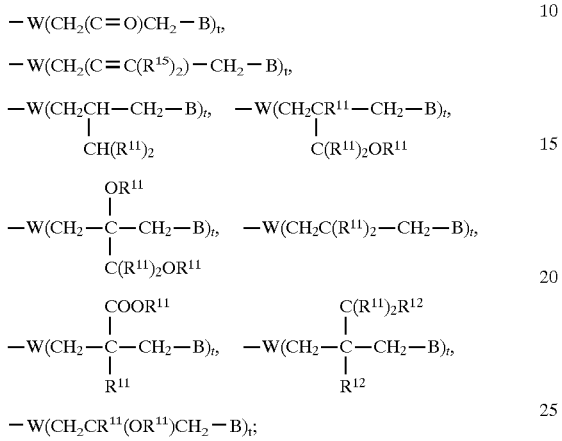

—W(CH$_2$CR$^{11}$(OR$^{11}$)CH$_2$—B)$_t$;

A is selected from the group consisting of —(C=O)R$^{11}$, sialic acid, Kemp's acid, quinic acid, —B, —SO$_3$M, —OSO$_3$M, —SO$_2$NH$_2$, —PO$_3$M'$_2$, —OPO$_3$M'$_2$, —NO$_2$, saturated or unsaturated carboxylic acids of 1 to 4 carbon atoms, optionally substituted with 1 to 2 hydroxyl groups, and esters, and amides of the carboxylic acid substitutents;

W is selected from the group consisting of a covalent bond, —O—, —N, —S—, —NH—, and —NAc—;

B is

wherein

U is selected from the group consisting of -R$^9$, —CH$_2$OR$^{10}$, —CH$_2$O-protecting group, —COOR$^{11}$, —CON(R$^{11}$)$_2$, and —COOM;

R$^9$ is lower alkyl;

each n is independently selected from the group 0, 1, 2, and 3;

each m is independently selected from the group 0, 1, 2, 3, and 4;

each q is independently selected from the group 0, 1, and 2;

each s is independently selected from the group 1, 2, and 3;

each z is independently selected from the group 1 and 2;

each t is independently selected from the group 1 and 2, with the proviso that when W is —N<, then t is 2, and for all other definitions of W, t is 1;

R$^{10}$ is selected from the group consisting of —H, —R$^{11}$, —SO$_3$M, —(C=O)R$^{11}$, —SO$_2$NH$_2$, —PO$_3$M'$_2$, -alk—COOR$^{13}$, alk—CON(R$^{11}$)$_2$ and —O-carbohydrate;

R$^{11}$ is independently selected from the group consisting of —H, lower alkyl, cyclic alkyl of 5 to 6 carbon atoms, heterocyclic alkyl of 4 to 5 carbon atoms and 1 to 2 heteroatoms, lower aryl and lower aralkyl;

R$^{12}$ is selected from the group consisting of —N(R$^{11}$)$_2$, and —SR$^{11}$;

R$^{13}$ is selected from the group consisting of R$^{11}$, and M;

R$^{14}$ is selected from the group consisting of —H, and —OR$^{10}$, with the proviso that when z is 2, then the two R$^{14}$ groups taken together with the carbon atoms to which each R$^{14}$ group is attached may form a double bond;

R$^{15}$ is independently selected from the group consisting of —R$^{11}$ and —COOH;

M is selected from the group consisting of Na$^+$, K$^+$, Mg$^{2+}$, and Ca$^{2+}$;

M' is selected from the group consisting of —H, —M, and R$^9$; and

X is selected from the group consisting of —O—, —S—, —C(R$^{11}$)$_2$—, and —N(R$^{11}$)—; and pharmaceutically acceptable salts thereof with the provisos that:

(a) when any of R$^1$, R$^2$, R$^3$, R$^4$, R$^5$, R$^6$, R$^7$, and R$^8$ are —Y—B and W is a covalent bond, then at least one adjacent position must be —OH or an ether moiety;

(b) no more than two of R$^1$, R$^2$, R$^3$, R$^4$, R$^5$, R$^6$, R$^7$, and R$^8$ may be Y—B when W is a covalent bond;

(c) no more than three of R$^1$, R$^2$, R$^3$, R$^4$, R$^5$, R$^6$, R$^7$, and R$^8$ may be a covalent bond to A;

(d) only one of R$^1$, R$^4$, R$^5$, and R$^8$ may be a covalent bond to B;

(e) when one of R$^1$, R$^4$, R$^5$, or R$^8$ is a covalent bond to B, then no more than two other naphthyl substituents can be a covalent bond to A when A is not B;

(f) at most three of R$^1$, R$^2$, R$^3$, R$^4$, R$^5$, R$^6$, R$^7$, and R$^8$ may be independently selected from the group consisting of —OH and ether moieties;

(g) at least one of R$^1$, R$^2$, R$^3$, R$^4$, R$^5$, R$^6$, R$^7$, and R$^8$ is —H;

(h) when any of R$^1$, R$^4$, R$^5$, and R$^8$ is a covalent bond to B, then the adjacent position must be —OH or an ether moiety;

(i) at least one of R$^1$, R$^2$, R$^3$, R$^4$, R$^5$, R$^6$, R$^7$, and R$^8$ is a substituent containing a B group, and at least one is a substituent containing an A group where A is not B; and (j) only when A is covalent bound to the naphthyl structure may A be —(C=O)R$^{11}$, and when A is —(C=O)R$^{11}$, at least one adjacent position must be —OH.

2. The compounds of claim 1 wherein at least one of R$^1$, R$^2$, R$^3$, R$^4$, R$^5$, R$^6$, R$^7$, and R$^8$ are independently selected from the group consisting of —W(CH$_2$(C=O)CH$_2$—B)$_t$, —W(CH$_2$(C=C(R$^{15}$)$_2$)—CH$_2$—B)$_t$, —W(CH$_2$CH—CH$_2$—B)$_t$, —W((CH$_2$)$_n$—B)$_t$
   |
   CH(R$^{11}$)$_2$ -continued

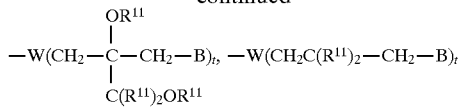

—W(CH$_2$—CR$_{11}$(OR$^{11}$)CH$_2$—B)$_t$, —OH, lower alkoxy, lower aryloxy, lower aryloxy, lower alkoxyaryl, A and B; wherein W is a covalent bond or —O—, and t is 1.

3. The compounds of claim 2 wherein at least one of R$^1$, R$^2$, R$^3$, R$^4$, R$^5$, R$^6$, R$^7$, and R$^8$ are selected from the group consisting of

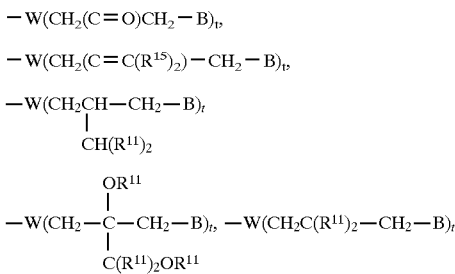

—W(CH$_2$—CR$_{11}$(OR$^{11}$)CH$_2$—B)$_t$, —OH, and A where A is not B.

4. The compounds of claim 1 wherein A and B are each selected from the group consisting of sialic acid and fucose.

5. The compounds of claim 1 wherein A is selected from the group consisting of Kemp's acid, quinic acid, R and S forms of mandelic acid, R and S forms of glyceric acid, R and S forms of lactic acid, propionic and acetic acid, and esters and amides any of the preceding acids —SO$_3$, and —PO$_3$:

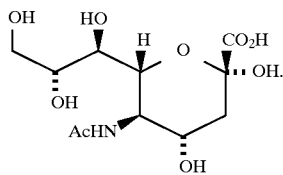

6. The compounds of claim 5 wherein B is selected from the group consisting of structure VI:

Structure VI

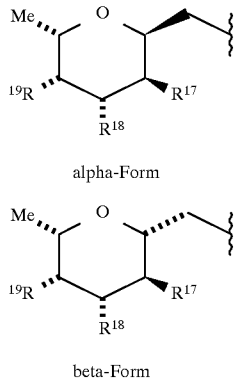

alpha-Form beta-Form wherein Me is a methyl group, R$^{17}$, R$^{18}$ and R$^{19}$ are each independently —OH, —F, —N(R$^9$)$_2$, wherein R$^9$ is lower alkyl; inositol; substituted inositol; imidazole; substituted imidazole; benzimidazole; substituted benzimidazole; guanidine; pentaerythritol; substituted pentaerythritol; and substituted butane of the formula —CH$_2$—CHR$^{17}$—CHR$^{18}$CH$_2$R$^{19}$ wherein R$^{17}$, R$^{18}$ and R$^{19}$ are independently OH, F or —N(R$^9$)$_2$.

7. The compounds of claim 1 wherein s is 1 or 2, R$^{14}$ is —H or —OH, X is —O—, U is —CH$_2$OR$^{10}$ or -R$^9$, and R$^{10}$ is -alk—COOH, —SO$_3$M, —H, or -alk—COOM.

8. The compounds of claim 7 wherein s is 2.

9. The compounds of claim 8 wherein B is selected from the group consisting of fucose, galactose, mannose, and arabinose.

10. The compounds of claim 1 wherein s numbers are 1 and 2.

11. The compounds of claim 10 wherein s is 2.

12. The compounds of claim 1 wherein q numbers are 0 and 1.

13. The compounds of claim 1 wherein m numbers are 0 and 1.

14. The compounds of claim 1 wherein n numbers are 0 and 3.

15. The compounds of claim 1 wherein R$^{10}$ is selected from the group consisting of —H, SO$_3$M, -alk—COOR$^{13}$, and —O—carbohydrate.

16. The compounds of claim 15 wherein R$^{10}$ is selected from the group consisting of —H, —SO$_3$M, and -alk—COOR$^{13}$.

17. The compounds of claim 1 wherein R$^{11}$ is selected from the group consisting of —H, lower alkyl, and lower aralkyl.

18. The compounds of claim 17 wherein R$^{11}$ is —H.

19. The compounds of claim 1 wherein R$^{12}$ is —N(R$^{11}$)$_2$.

20. The compounds of claim 1 wherein R$^{14}$ is selected from the group consisting of —H and —OH.

21. The compounds of claim 1 wherein R$^{15}$ is selected from the group consisting of —COOH, —H, and —CH$_3$.

22. The compounds of claim 1 wherein M is Na$^+$.

23. The compounds of claim 1 wherein M' is selected from the group consisting of —H, Na$^+$, and —CH$_3$.

24. The compounds of claim 1 wherein X is —O—.

25. The compounds of claim 1 wherein U is selected from the group consisting of —CH$_2$OR$^{10}$ and -R$^9$.

26. The compounds of claim 1 wherein W is selected from the group consisting of a covalent bond and —O—, and t is 1.

27. The compounds of claim 3 wherein at least one of R$^1$, R$^2$, R$^3$, R$^4$, R$^5$, R$^6$, R$^7$, and R$^8$ are independently selected from the group consisting of —W(CH$_2$(C=C(R$^{15}$)$_2$)—CH$_2$—B$_t$ where W is a covalent bond or —OH, t is 1, and R$^{15}$ is independently —H, —CH$_3$, and COOH.

28. The compounds of claim 1 wherein R$^3$ and R$^6$ are selected from the group consisting of —SO$_3$M, —OSO$_3$M, —NO$_2$, and —CO$_2$H, and at least one of R$^1$, R$^2$, or R$^7$ is selected from the group OH and —NH$_2$.

29. The compounds of claim 1 wherein R$^1$ is a covalent bond to B, R$^2$ and R$^3$ are selected from the group consisting of —OH,

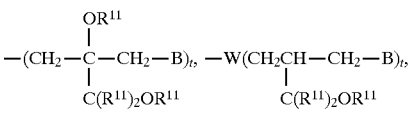

-continued and $-W(CH_2C(R^{11})_2-CH_2-B)_t$ where W is a covalent bond and t is 1, $R^7$ is selected from the group consisting of —H or —OH, and $R^6$ is selected from the group consisting of —H and —(CH$_2$)$_m$—(CHR$^9$)$_q$—(CH$_2$)$_m$—A, where each m and q are independently selected from 0 or 1, and A is a saturated or unsaturated carboxylic acid of 1 to 4 carbon atoms, optionally substituted with 1 to 2 hydroxy groups, and esters and amides thereof.

30. The compounds of claim 29 wherein s is 1 or 2, $R^{14}$ is —H or —OH, X is —O—, U is —CH$_2$OR$^{10}$ or -R$^9$, and $R^{10}$ is -alk—COOH, —SO$_3$M, —H, or -alk—COOM.

31. The compounds of claim 29 wherein $R^{15}$ is —H.

32. A method of treating a selectin-mediated disorder selected from the group consisting of cancer, auto-immune disorders, and inflammation, comprising the step of:
    administering to a patient in need thereof a therapeutically effective amount of a compound of claim 1.

33. A pharmaceutical composition comprising at least one compound of claim 1 and a pharmaceutically acceptable carrier, wherein at least one compound of claim 1 is bound to a pharmaceutically active drug.

* * * * *